United States Patent [19]
Garret et al.

[11] Patent Number: 5,049,669
[45] Date of Patent: Sep. 17, 1991

[54] ANALGESIC PHENOTHIAZINE DERIVATIVES

[75] Inventors: Claude Garret, Fontenay sous Bois; Claude Guyon, Saint Maur des Fosses; Bernard Plau, Fresnes; Gerard Taurand, Creteil, all of France

[73] Assignee: Rhone-Poulenc Sante, Antony, France

[21] Appl. No.: 364,155

[22] Filed: Jun. 12, 1989

[30] Foreign Application Priority Data

Jun. 10, 1988 [FR] France ................ 88 07770

[51] Int. Cl.$^5$ .................. A61K 31/54; C07D 279/24; C07D 417/06
[52] U.S. Cl. ................ 514/226.2; 514/224.8; 540/599; 544/41; 544/42
[58] Field of Search ............... 544/41, 42; 540/599; 514/224.8, 226.2

[56] References Cited

U.S. PATENT DOCUMENTS

| | | | |
|---|---|---|---|
| 2,956,996 | 10/1960 | Craig et al. | 544/44 |
| 3,112,310 | 11/1963 | Cusic et al. | 544/44 |
| 3,375,248 | 3/1968 | Antoni et al. | 544/39 |

OTHER PUBLICATIONS

Kuromi et al., "Central actions of methotrimeprazine ..", CA 77: 122258a (1972).
French Search Report, Feb. 23, 1989.

*Primary Examiner*—Alan L. Rotman
*Assistant Examiner*—Celia Chang
*Attorney, Agent, or Firm*—Morgan & Finnegan

[57] ABSTRACT

Phenothiazine derivatives of general formula (I), in which R is a linear or branched (1 to 6 C) alkyl radical and $R_1$ and $R_2$, which may be identical or different, are linear or branched (1 to 4 C) alkyl radicals or form, with the nitrogen atom to which they are attached, a 4- to 7-membered heterocycle, their isomeric forms and mixtures thereof as well as their addition salts with acids, possess analgesic and diuretic activity.

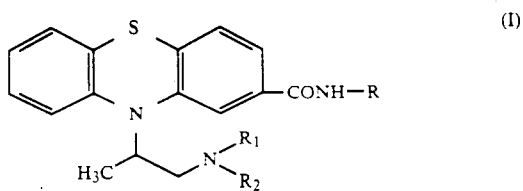

(I)

20 Claims, No Drawings

ANALGESIC PHENOTHIAZINE DERIVATIVES

FIELD OF THE INVENTION

In the analgesic field, recent progress in the study of receptors has enabled several types of opiate receptors to be demonstrated.

BACKGROUND OF THE INVENTION

Traditional compounds of the morphine type act at the level of the Mu receptors, but have the drawback of causing troublesome side effects (phenomena of physical and mental dependence, respiratory depression, etc.), in consequence of which it is hazardous to use such products in some subjects.

Products which are more specific for the Kappa receptors exhibit a potent analgesic activity without causing the side effects of traditional morphine type compounds.

Amides derived from phenothiazine of general formula:

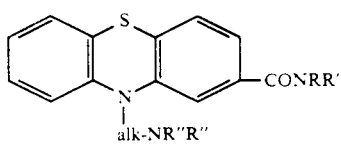

in which R is, in particular, a hydrogen atom, had been described in U.S. Pat. No. 3,112,310 in connection with their activity with respect to the central nervous system.

DETAILED DESCRIPTION OF THE INVENTION

It has now been found that a particular class of amides derived from phenothiazine, not studied hitherto and defined by the general formula:

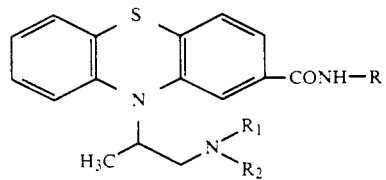

as well as their addition salts with acids, exhibits a potent analgesic activity linked to a preferential affinity for the Kappa receptors, which is not observed with the already known amides derived from phenothiazine.

In the general formula (I), the symbol R is an alkyl radical containing 1 to 6 carbon atoms in a straight or branched chain, and the symbols $R_1$ and $R_2$, which may be identical or different, are linear or branched alkyl radicals containing 1 to 4 carbon atoms or form, together with the nitrogen atom to which they are attached, a 4- to 7-membered heterocycle.

It is understood that the products of general formula (I) exist in the form of isomers, and that these isomeric forms as well as the mixtures thereof fall within the scop of the present invention.

The phenothiazine derivatives of general formula (I) may be obtained by transthioamidation of a primary thioamide of general formula:

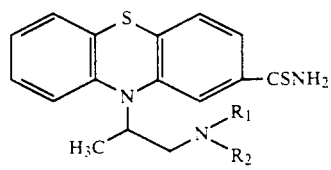

in which $R_1$ and $R_2$ are as defined as above, by the action of an amine of general formula:

$$R-NH_2 \qquad (III)$$

in which R is defined as above, followed by oxidation of the substituted thioamide obtained, of general formula:

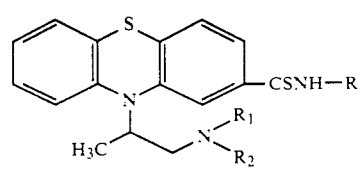

in which R, $R_1$ and $R_2$ are defined as above.

In practice, it is not essential to isolate the thioamide of general formula (IV) in order to prepare the amide of general formula (I).

The reaction is advantageously performed in an organic solvent such as an alcohol (for example ethanol, methanol or isopropanol) or without a solvent, at a temperature of between 100 and 250° C.

Where it is desired to isolate the amide of general formula (I), without prior isolation of the thioamide of general formula (IV), chromatography or crystallization is employed directly When it is desired to isolate the substituted thioamide of general formula (IV), it is preferable to work in the presence of hydrogen sulphide, and the secondary thioamide obtained, or its salt, is then oxidized by any known method for obtaining an amide from the corresponding thioamide without affecting the remainder of the molecule.

The oxidation is advantageously accomplished by means of a mercuric salt (e.g. mercuric acetate) or a cuprous salt, in an organic solvent such as ketone (e.g. acetone), an alcohol, an ester or a carboxylic acid such as, e.g. acetic acid, at a temperature of between 0 and 100° C.

It is also possible to perform the oxidation using methods similar to those described by:

H. J. Kim et al., Synthesis, 11, 970 (1986);

M. T. M. El-Wassimy, Tetrahedron 39 (10), 1729 (1983),

K. A. Jorgensen et al., Tetrahedron 38 (9), 1163 (1982),

A. G. Samuelson et al., Tetrahedron Letters, 27 (33), (1986).

The products of general formula (I) may also be obtained from a nitrile of general formula:

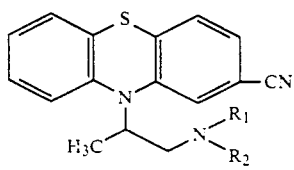

(V)

in which $R_1$ and $R_2$ are as defined above, by any known method for obtaining a substituted amide from a nitrile without affecting the remainder of the molecule.

In particular, an intermediate imidate is prepared in situ and reacted with a halogenated derivative of general formula:

R—Hal  (VI)

in which R is defined as above and Hal denotes an iodine or bromine atom.

Preferably, the reaction is performed in an alcohol-/alcoholate or alcohol/potassium hydroxide mixture, e.g. tert-butanol/potassium tert-butylate., tert-butanol/potassium hydroxide or isobutanol/potassium isobutylate, at a temperature of between 50 and 150° C.

It is also possible to work in the presence of a large excess of an amine of general formula (III), with or without a solvent, at a temperature of between 150 and 250° C.

Where appropriate, the solvents are advantageously chosen from alcohols (e.g. ethanol, methanol), ethers having a high boiling point, polyethers and aromatic hydrocarbons (e.g. toluene, xylene, chlorobenzene).

It is also possible to work according to the method described by S. LINKE, Synthesis, 4, 303 (1978) or according to the method described by G.W. CANNON et al., J. Org. Chem., 18, 516 (1953).

The amides of general formula (I) may also be obtained from an acid of general formula:

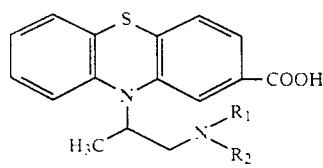

(VII)

in which $R_1$ and $R_2$ are defined as above, by any known method for obtaining a substituted amide from an acid without affecting the remainder of the molecule.

The procedure used employs, in particular, the action of an amine of general formula (III) on a reactive derivative of the acid, e.g. the acid chloride, an activated ester or a mixed anhydride, in an organic solvent such as an ether or a chlorinated solvent (e.g. methylene chloride, chloroform, dichloroethane) or in an amide (dimethylformamide) in the presence of an acceptor for acid such as a nitrogenous organic base such as, e.g., a trialkylamine (triethylamine in particular), at a temperature of between $-40$ and $+40°$ C.

It is also possible to react the amine of general formula (III) directly with the acid, working in the presence of a condensing agent such as a carbodiimide (dicyclohexylcarbodiimide), of N,N'-carbonyldiimidazole or of N-hydroxybenzotriazole in an organic solvent as mentioned above, and at a temperature as defined above.

The thioamide of general formula (II) may be obtained from a nitrile of general formula (V) by any known method for obtaining a thioamide from a nitrile without affecting the remainder of the molecule.

The procedure is generally performed in an anhydrous basic medium, in the presence of hydrogen sulphide at a temperature of between 0 and 100° C. The reaction is advantageously performed in the presence of a nitrogenous organic base such as triethylamine, in an organic solvent such as pyridine.

The acid of general formula (VII) may be obtained from a nitrile of general formula (V) by any known method for obtaining an acid from a nitrile without affecting the remainder of the molecule. The procedure used employs, in particular, hydrolysis in an acid or basic medium in an organic solvent at a temperature between 50° C. and the refluxing temperature of the reaction mixture. The reaction is advantageously performed in glycol in the presence of potassium hydroxide.

The nitrile of general formula (V) may be obtained according to the following scheme:

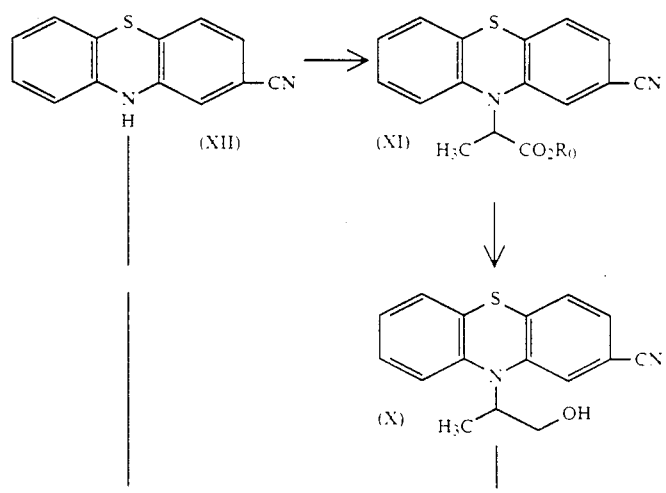

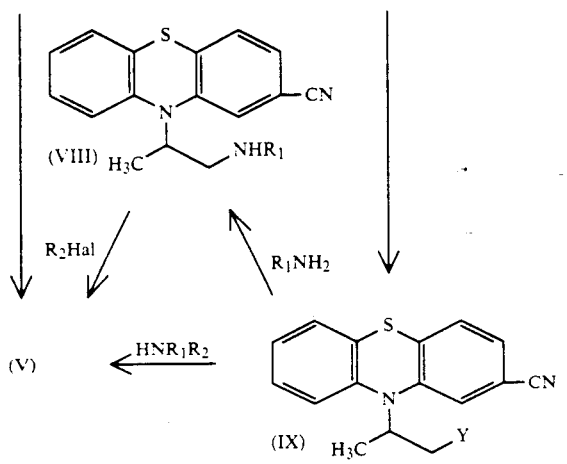

in which $R_1$ and $R_2$ are defined as above, Hal is a halogen atom, Y is a p-toluenesulphonyloxy, methylsulphonyloxy or diaryloxyphosphoryloxy residue and $R_o$ is an alkyl radical (e.g. ethyl), and the working conditions of which are defined in greater detail below in Examples 1, 5, 6, 8, 21, 22, 26 to 28 and 32.

The nitrile of general formula (XII) may be obtained as described in U.S. Pat. No. 2,877,224.

The isomers of the products of general formula (I) may be obtained according to known methods.

The procedure used employs, in particular, the preparation of the isomer of the phenothiazine derivative of general formula (X), which is converted to the amide derived from phenothiazine of general formula (I) by the methods described above.

The optically active derivative of the product of general formula (X) is obtained, in particular, by the preparation of a diacid ester, formation of an optically active salt, separation of the isomers by crystallization and saponification of the isomer obtained.

More especially, the ester is obtained by means of a diacid anhydride such as, e.g., phthalic anhydride or maleic or succinic anhydride. The salt is formed by the addition of an optically active amine, e.g. (+)-1-phenylethylamine or (−)-1-phenylethylamine.

In the examples which follow, the phenothiazine derivatives prepared from the alcohol of general formula (X) for which the optical rotation in chloroform solution is positive are referred to as the D series; the phenothiazine derivatives prepared from the alcohol of general formula (X) for which the optical rotation in chloroform solution is negative are referred to as the L series.

The products of general formula (I) may be purified by chromatography or crystallization.

The phenothiazine derivatives of general formula (I) may be converted to addition salts with acids, by the action of an acid in an organic solvent such as an alcohol, a ketone, an ester, an ether or a chlorinated solvent. The salt precipitates, where appropriate after concentration of its solution; it is separated by filtration or decantation.

As pharmaceutically acceptable salts, there may be mentioned the addition salts with inorganic acids such as hydrochlorides, hydrobromides, sulphates, nitrates or phosphates, or organic acids such as acetates, propionates, succinates, maleates, fumarates, methanesulphonates, p-toluenesulphonates, isethionates or substitution derivatives of these compounds.

The phenothiazine derivatives of general formula (I) exhibit an especially advantageous analgesic and diuretic activity on account of their preferential affinity for the Kappa receptors and their low toxicity.

They have been shown, in effect, to be active at concentrations of between 1 and 100 nM in the method of tritiated ethylketocyclazocine binding in guinea pig cerebellum homogenates, based on the technique of L.E. Robson et al., Opioid binding sites of the Kappa type in guinea pig cerebellum, Neuroscience, 12, 621 (1984).

They have also been shown to be active in the technique of inhibition of the contractions induced b electrical stimulation on isolated guinea pig ileum (based on W.D.M. Paton, Brit. J. Pharmacol., 11, 119 (1957)) at concentrations of between 1 and 100 nM.

Products having an affinity for the Kappa receptors manifest a diuretic effect [J. D. Leander, The Journal of Pharmacology and Experimental Therapeutics, 224 (1), 89 (1983) and G. R. Slizgi et al., The Journal of Pharmacology and Experimental Therapeutics, 230 (3), 641 (1984)]. It has also been demonstrated, by studying several products, that the products of general formula (I) manifest significant diuretic effect in rats, at doses of between 1 and 20 mg/kg administered subcutaneously, in the technique described by J.D. Leander (reference above).

Moreover, the acute toxicity ($LD_{50}$) of the products of formula (I) in mice is between 30 and 100 mg/kg p.o. and doses markedly greater than 100 mg/kg p.o.

Of special importance are the products of general formula (I) in which the symbol R is an alkyl radical containing 2 to 6 carbon atoms in a straight or branched chain, and the symbols $R_1$ and $R_2$, which may be identical or different, are linear or branched alkyl radicals containing 1 to 3 carbon atoms or form, together with the nitrogen atom to which they are attached, a 5- to 7-membered heterocycle.

Among these more especially active products are the products of general formula (I) in which the symbol R is an alkyl radical containing 3 to 6 carbon atoms in a straight or branched chain and the symbols $R_1$ and $R_2$, which may be identical or different, are linear or branched alkyl radicals containing 2 or 3 carbon atoms or form, together with the nitrogen atom to which they are attached, a 5- to 7-membered heterocycle, in the form of a mixture of isomers or in the form of the isomers of the L series, and in particular the following products:

N-propyl-10-[1-(1-pyrrolidinyl)-2-propyl]-2-phenothiazinecarboxamide in its isomeric forms or mixtures thereof, N-(3-methylbutyl)-10-[1-(1-pyrrolidinyl)-2-propyl]-2-phenothiazinecarboxamide in its isomeric forms or mixtures thereof, N-(2-methylpropyl)-10-[1-(1-pyrrolidinyl)-2-propyl]-2-phenothiazinecarboxamide in its isomeric forms or mixtures thereof, N-butyl-10-[1-(1-pyrrolidinyl)-2-propyl]-2-phenothiazinecarboxamide in its isomeric forms or mixtures thereof, N-(3-methylbutyl)-10-[1-piperidino-2-propyl]-2-phenothiazinecarboxamide in its isomeric forms or mixtures thereof.

EXAMPLES

The examples which follow, given without implied limitation, illustrate the present invention.

EXAMPLE 1

Propylamine (4.85 cc) is added to a solution of 10-[(2RS)-1-diethylamino-2-propyl]-2-phenothiazinecarbothioamide (4.38 g) in absolute ethanol (60 cc). The mixture is brought to 150° C. for 16.5 hours. The reaction mixture is diluted with ethyl acetate (200 cc) and then washed with distilled water (3×100 cc). The organic phase is dried over magnesium sulphate, filtered and then concentrated to dryness under reduced pressure (30 mm Hg; 4 kPa) at 40° C. The residue is purified by chromatography on a column (height: 24.0 cm; diameter: 4 cm) of silica gel (0.04-0.06 mm) with a slight excess pressure of nitrogen (40 kPa), eluting with mixtures of cyclohexane and ethyl acetate in proportions (by volume) of 90:10 (1.5 liters) and 75:25 (3 liters), and then with pure ethyl acetate (1.5 liters) and with a 95:5 (by volume) mixture (3 liters) of ethyl acetate and methanol, collecting 100-cc fractions. Fractions 20 to 35 are combined and concentrated under reduced pressure (30 mm Hg; 4 kPa) to give an orange product (3.95 g) of meringue-like consistency. 0.13 g of this product is dissolved in boiling 2-propanol (1 cc) and treated with fumaric acid (0.039 g) dissolved in 2-propanol (1 cc). Crystallization is primed by scratching. The mixture is left stirred for 24 hours at 5° C. and the crystals are then filtered off and dried at 50° C. under reduced pressure (5 mm Hg; 0.7 kPa) to give 10-[(2RS)-1-diethylamino-2-propyl]-N-propyl-2-phenothiazinecarboxamide fumarate (0.044 g), m.p. 110° C.

Proton NMR (250 MHz, DMSO, δ in ppm, J in Hz):

0.87 (Mt, 9H, propyl-CH$_3$ and N(CH$_2$CH$_3$)$_2$); 1.52 (Mt, 2H, —CH$_2$—CH$_2$—CH$_3$); 1.62 (D, J=7, —CH$_3$); 2.53 (Mt, masked by the solvent band, —N(CH$_2$CH$_3$)$_2$); 2.72 (DD, J=13 and 6, 1H, 1H of >N—CH$_2$—); 3.05 (DD, J=13 and 7.5, 1H, 1H of >N—CH$_2$—); 3.20 (Mt, J=5.5 and 7, 2H, —CONH—CH$_2$—); 4.18 (Mt, J=7.5, 7 and 6, 1H, >N—CH<); 6.6 (S, 2H, fumarate —CH=CH—); 6.9 to 7.25 (Mt, 5H, aromatic); 7.39 (DD, J=8 and 1, 1H, -H at 3-position); 7.52 (D, J=1, 1H, —H at 1-position); 8.4 (T, J=5.5, 1H, —CONH—).

Infrared spectrum (KBr), characteristic bands in $m^{-1}$: 3280, 3070, 2960, 2940, 2880, 2600, 2500, 2270, 1695, 1630, 1590, 1550, 1470, 1400, 1350, 1320, 1235, 990, 980, 870, 840, 750, 635.

10-[(2RS)-1-Diethylamino-2-propyl]-2-phenylthiazinecarbothioamide may be prepared in the following manner:

A mixture of 10-[(2RS)-1-diethylamino-2-propyl]-2-phenothiazinecarbonitrile (8.44 g) and triethylamine (3.5 cc) in anhydrous pyridine (60 cc) is saturated by bubbling in hydrogen sulphide for 5 hours at 25° C. The clear solution obtained is kept stirred for 12 hours at 25° C., and the mixture is then outgassed by bubbling through nitrogen for 90 minutes. The reaction mixture is diluted with ethyl acetate (500 cc) and washed with distilled water (8×200 cc). The organic phase is dried over magnesium sulphate, filtered and concentrated to dryness under reduced pressure (30 mm Hg; 4 kPa). The residue is purified by chromatography on a column of basic alumina (0.05-0.16 mm) (height: 31 cm; diameter: 2.6 cm), eluting with mixtures of cyclohexane and ethyl acetate in proportions (by volume) of 80:20 (5 liters) and 50:50 (5 liters) and collecting 100-cc fractions. Fractions 4 to 90 are combined and concentrated under reduced pressure (30 mm Hg; 4 kPa) to give 10-[(2RS)-1-diethylamino-2-propyl]-2-phenothiazinecarbothioamide (8.54 g) in the form of an orange-yellow product of honey-like consistency.

Proton NMR spectrum (250 MHz, DMSO, δ in ppm, J in Hz):

0.84 (T, J=7, 6H, —N(CH$_2$CH$_3$)$_2$); 1.62 (D, J=7, 3H, —CH$_3$); 2.45 (Mt, approximately 4H, —N(CH$_2$CH$_3$)$_2$); 2.69 (DD J=13.5 and 6, 1H, 1H of >N—CH$_2$—); 2.99 (DD, J=13.5 and 6.5, 1H, 1H of >N—CH$_2$—); 4.13 (Mt, J=7, 2.9 6, 1H, >N—CH<); 6.9 to 7.2 (Mt, 5H, aromatic); 7.39 (DD, J=8 and 1, 1H, —H at 3-position); 7.74 (D, J=1, 1H, —H at 1-position); 9.47 and 9.83 (2S, 1H each, —CSNH$_2$).

10-[(2RS)-1-Diethylamino-2-prop-yl]-2-phenothiazinecarbonitrile may be prepared in the following manner:

A solution of 1-diethylamino-2-propanol (78.7 g) in N,N-dimethylformamide (60 cc) is added dropwise in the course of 55 minutes to a solution of p-toluenesulphonyl chloride (114.4 g) in N,N-dimethylformamide (600 cc). The mixture is stirred at 25° C. for 12 hours.

Sodium hydride (19.2 g; in 50% strength dispersion in vaseline) is added in the course of 20 minutes to a solution of 2-phenothiazinecarbonitrile (44.86 g) in N,N-dimethylformamide (600 cc). The mixture obtained is then heated to 110° C., after which the solution of 1-diethylamino-2-propyl p-toluenesulphonate hydrochloride prepared above is added in the course of 35 minutes. The reaction mixture is stirred at 110° C. for 7 hours and then diluted, after being cooled, with ethyl acetate (2 liters). The mixture is washed with distilled water (5 × 1 liter). The organic phase is extracted with 4 N hydrochloric acid (240 cc) and the acid aqueous phase is washed with ethyl acetate (750 cc) and then alkalinized medium is then extracted with ethyl acetate (1250 cc). The organic phase is washed with distilled water (3×300 cc), dried over magnesium sulphate, filtered and concentrated to dryness under reduced pressure (30 mm Hg; 4 kPa) at 40° C. The residue is stirred in the presence of ethyl ether (100 cc); a precipitate forms and this is filtered off, and the filtrate is purified by chromatography on a column of silica gel (0.2-0.063 mm) (height: 82 cm; diameter: 4.5 cm), eluting with an 80:20 (by volume) mixture (7 liters) of cyclohexane and ethyl acetate and collecting 100-cc fractions. After concentration to dryness under reduced pressure (30 mm Hg., 4 kPa) at 50° C., 10-[(2RS)-1-diethylamino-2-prop-yl]-2-phenothiazinecarbonitrile (6.76 g) is obtained from fractions 4 to 9, and a mixture (8.5 g) of 10-[(2RS)-1-diethylamino-2-propyl]-2-phenothiazinecarbonitrile and 10-[(1RS)-2-diethylamino-1-propyl]-2-phenothiazinecarbonitrile is obtained from fractions 10 to 22. The mixture is purified by chromatography on a column of silica gel (0.2-0.063 mm) (height: 67 cm; diameter: 3.0 cm), eluting with an 85:15 (by volume) mixture (3 liters) cyclohexane and ethyl acetate and collecting 50-cc fractions. Fractions 22 to 29 are combined and concentrated to dryness at 50° C. under reduced pressure (30 mm Hg; 4 kPa) to give 10-[(2RS)-1-diethylamino2-propyl]-2-phenothiazinecarbonitrile (2.76 g).

Proton NMR spectrum (250 MHz, DMSO, δ in ppm, J in Hz):

0.85 (T, J=7.5, 6H, —N(CH$_2$CH$_3$)$_2$); 1.57 (D, J=7, 3H, —CH:); 2.25 to 2.57 (Mt, approximately 4H, —N(CH$_2$CH$_3$)$_2$); 2.63 (DD, J=13.5 and 6, 1H, 1H of >NCH$_2$—); 2.98 (DD, J=13.5 and 6.5, 1H, 1H of >NCH$_2$—); 4.08 (Mt, J=7, 6.5 and 6, 1H >N—CH<); 6.9 to 7.25 (Mt, 5H, aromatic); 7.31 (DD, J=8 and 1, 1H, —H at 3-position), 7.59 (D, J=1, 1H, —H at 1-position).

EXAMPLE 2

3-Methylbutylamine (2.9 cc) is added to a solution of 10[(2RS)-1-diethylamino-2-propyl]-2-phenothiazinecarbothioamide (1.86 g) in absolute ethanol (25 cc). The mixture is brought to 150° C. for 16 hours and then diluted with ethyl acetate (100 cc) and washed with distilled water (3×50 cc). The organic phase is dried over magnesium sulphate, filtered and then concentrated to dryness under reduced pressure (30 mm Hg; 4 kPa) at 40° C. The residue is purified by chromatography on a column (height: 18.5 cm; diameter: 2.6 cm) of silica gel (0.04-0.06 mm) with a slight excess pressure of nitrogen (40 kPa), eluting with a 50:50 (by volume) mixture (1 liter) of cyclohexane and ethyl acetate and then with pure ethyl acetate (500 cc), collecting 60-cc fractions. Fractions 8 to 18 are combined and concentrated to dryness under reduced pressure (30 mm Hg; 4 kPa) at 40° C. to give an orange product (0.36 g) of meringue-like consistency. The latter is purified by chromatography on a column of basic alumina (0.05-0.16 mm) (height: 8.5 cm; diameter: 1.2 cm), eluting with a 90:10 by volume) mixture (150 cc) of cyclohexane and ethyl acetate and collecting 7-cc fractions. Fractions 6 to 20 are combined and concentrated under reduced pressure (30 mm Hg; 4 kPa) at 40° C. to give a yellowish resin (0.22 g). This product is dissolved in boiling 2-propanol (2 cc) and treated with fumaric acid (0.06 g) dissolved in 2-propanol (1 cc). Crystallization is primed by scratching. The mixture is left stirred for 24 hours and the crystals are then filtered off, washed with diethyl ether (3×1 cc), and dried at 50° C. under reduced pressure (5 mm Hg; 0.7 kPa) to give 10-[(2RS)-1-diethylamino-2-propyl]-N-(3-methylbutyl)-2-phenothiazinecarboxamide fumarate (0.13 g), m.p. 138° C.

Proton NMR spectrum (250 MHz, DMSO, δ in ppm, J in Hz):

0.87 (T, J=7, 6H, —N(CH$_2$CH$_3$)$_2$); 0.92 (D, J=7, 6H, —CH(CH$_3$)$_2$; 1.42 (Q, J=7, 2H >NCH$_2$CH$_2$—); 1.62 (Mt, 1H, 3-methylbutyl>CH—); 1.64 (D, J=7, 3H, —CH$_3$); 2.52 (Mt, masked by the DMSO band, >N—CH$_2$—CH$_2$); 2.73 (DD, J=13 and 6, 1H, 1H of >N—CH$_2$); 3.05 (DD, J=13 and 7.5, 1H, 1H of >N—CH$_2$—); 3.26 (Mt, 2H, -CONH-C/$_2$—); 4.17 (Mt, J=7.5, 7 and 6, 1H, >N—CH<); 6.62 (S, 2H, fumarate —CH=CH—); 6.9 to 7.25 (Mt, 5H, aromatic); 7.39 (DD, J=8 and 1, 1H, -H at 3-position); 7.52 (D, J=1, 1H, —H at 1-position); 8.33 (T, J=6, 1H, —CONH—).

Infrared spectrum (KBr), characteristic bands in cm$^{-1}$:

3300, 3060, 2960, 2940, 2870, 2640, 2500, 1900, 1705, 1630, 1590, 1555, 1460, 1415, 1385, 1310, 1230, 985, 880, 830, 755, 635.

EXAMPLE 3

A solution of mercuric acetate (0.70 g) in acetic acid (11 cc) is added dropwise during a period of 10 minutes to a solution of 10-[(2RS)-1-diethylamino-2-propyl]-N-ethyl-2-phenothiazinecarbothioamide (0.87 g) in glacial acetic acid (11 cc). The reaction mixture is stirred for 90 minutes at 25° C. and then filtered on sintered glass covered with supercel. The celite is washed with acetic acid (2×2 cc) and the combined filtrates are concentrated to dryness under reduced pressure (30 mm Hg; 4 kPa) at 40° C. to give a residue which is diluted in ethyl acetate (50 cc). The organic phase is washed with 1 N sodium hydroxide (20 cc) and distilled water (3×20 cc) and then with brine (1×20 cc), dried over magnesium sulphate, filtered and concentrated to dryness under reduced pressure (30 mm Hg; 4 kPa) at 40° C. to give a residue which is purified by chromatography on a column (height: 15.5 cm; diameter: 1.6 cm) of alumina (0.05-0.16 mm), eluting with mixtures of cyclohexane and ethyl acetate in proportions (by volume) of 80:20 (375 cc) and 75:25 (3 liters), collecting 25-cc fractions. The first three liters are discarded and fractions 3 to 12 are combined and concentrated to dryness under reduced pressure (30 mm Hg; 4 kPa) at 40° C. to give 10-[(2RS)-1-diethylamino-2-propyl]-N-ethyl-2-phenothiazinecarboxamide (0.54 g).

Fumaric acid (0.13 g) dissolved in 2-propanol (5 cc) under reflux is added to a solution of 10-[(2RS)-1-diethylamino-2-propyl]-N-ethyl-2-phenothiazinecarboxamide (0.44 g) in boiling 2-propanol (5 cc). Crystallization is primed by scratching and the mixture is stirred for 5 hours at 25° C. The crystals are filtered off on sintered glass, washed with ice-cold 2-propanol (2×3 cc) and dried in the ambient air to give 10-[(2RS)-1-diethylamino-2-propyl]-N-ethyl-2-phenothiazinecarboxamide fumarate (0.51 g), m.p. 135° C.

Proton NMR (400 MHz, DMSO, δ in ppm, J in Hz):

0.90 and 1.27 (2T, J=7, 6H and 3H respectively, —N(CH$_2$CH$_3$)$_2$ and >NHCH$_2$CH$_3$); 1.67 (D, J=7, 3H, —CH$_3$); 2.61 (Mt, 4H, —N(CH$_2$CH$_3$)$_2$; 2.84 (DD, J=14 and 6, 1H, 1H of >N—CH$_2$—); 3.15 (DD, J=14 and 7.5, 1H, 1H of >NCH$_2$—); 3.28 (Mt, J=7 and 5.5, 2H, —CONH—CH$_2$—); 4.29 (Mt, J=7.5, 7 and 6, 1H >N—CH<); 6.6 (S, 2H, fumarate —CH=CH—); 6.9 to 7.3 (Mt, 5H, aromatic); 7.42 (D, J=8, 1H, —H at 3-position); 7.54 (S, 1H, —H at 1-position); 8.48 (T, J=5.5, 1H, —CONH—).

Infrared spectrum (KBr), characteristic bands in cm$^{-1}$: 3270, 3060, 3030, 2975, 2935, 2880, 2740, 2650, 2500, 1920, 1700, 1630, 1590, 1555, 1550, 1460, 1420, 1315, 1230, 990, 755, 640.

10-[(2RS)-1-Diethylamino-2-propyl]-N-ethyl-2-phenothiazinecarbothioamide may be prepared in the following manner:

Ethylamine (2.80 cc) in 9 N ethanolic solution is added to a solution of 10-[(2RS)-1-diethylamino-2- propyl]-2-phenylthiazinecarbothioamide (1.86 g) in absolute ethanol (25 cc). The mixture is brought to 150° C. for 16 hours. The reaction mixture is concentrated to dryness under reduced pressure (30 mm Hg; 4 kPa). The residue is purified by chromatography on a column (height: 17.5 cm; diameter: 2.8 cm) of silica gel (0.04-0.06 mm) with a slight excess pressure of nitrogen (40 kPa), eluting with mixtures of cyclohexane and ethyl acetate in proportions (by volume) of 80:20 (1.5 liters) and 50:50 (1.5 liters) and then with pure ethyl acetate (1.5 liters), collecting 100-cc fractions. Fractions 9 to 39 are combined and concentrated to dryness under reduced pressure (30 mm Hg; 4 kPa) to give 10-[(2RS)-1-diethylamino-2-propyl]-N-ethyl-2-phenothiazinecarbothioamide (0.93 g).

Proton NMR spectrum (250 MHz, DMSO, δ in ppm, J in Hz):

1.23 (T, J=7, 3H, —NHCH$_2$CH$_3$); 3.7 (Mt, —CSN-H—CH$_2$); 6.9 to 7.25 (Mt, 5H, aromatic).

EXAMPLE 4

Mercuric acetate (0.38 g) is added with stirring to a solution of N-propyl-10-[(2RS)-1-(1-pyrrolidinyl)-2-propyl]-2-phenothiazinecarbothioamide neutral fumarate (0.6 g) in acetic acid (10 cc), and stirring is continued for 4 hours 30 minutes at a temperature in the region of 20° C. The black reaction mixture is diluted with distilled water (25 cc) and ethyl acetate (50 cc), and then filtered and alkalinized with stirring with 4 N aqueous sodium hydroxide solution to pH 13. After settling ha taken place, the organic phase is separated and the aqueous phase is extracted with ethyl acetate (20 cc). The combined organic phases are washed successively with saturated aqueous sodium chloride solution (50 cc). After drying over magnesium sulphate, filtration and concentration to dryness under reduced pressure (30 mm Hg; 4 kPa) at 40° C., the residual yellow oil (0.43 g) is dissolved in ethanol (2 cc) and then treated with a solution of fumaric acid (0.14 g) in ethanol (5 cc), concentrated to half the volume under reduced pressure (30 mm Hg; 4 kPa) at 40° C. and treated with ethyl ether (20 cc). After 2 hours' stirring at a temperature in the region of 20° C., the solid formed is drained and dried under reduced pressure (5 mm Hg; 0.7 kPa) at 40° C. N-Propyl-10-[(2RS)-1-(1-pyrrolidinyl)-2-propyl]-2-phenothiazinecarboxamide acid fumarate (0.38 g) is thereby obtained in the form of a pale yellow solid, m.p. 75–80° C. (melts forming a paste).

Proton NMR (250 MHz, DMSO, δ in ppm, J in Hz):

0.88 (T, J=7, 3H, propyl —CH$_3$); 1.55 (Mt, 2H, propyl —CH$_2$—CH$_3$); 1.65 (D, J=6.5, 3H, —CH$_3$); 1.73 (Mt, 4H, pyrrolidine —CH$_2$—); 2.75 (Mt, 4H, pyrrolidine >N—CH$_2$—); 3.20 Mt, 4H; >N—CH$_2$— and —CONHCH$_2$—); 4.35 (Mt, 1H, >N—CH<); 6.55 (S, 2H, fumarate >CH=CH<); 6.9 to 7.3 (Mt, 5H, aromatic); 7.42 (D, J 8, 1H, -H at 3-position); 7.50 (S, 1H, —H at 1-position); 9.46 (T, J=10 5.5., 1H, —CONH—).

Infrared spectrum (KBr), characteristic bands in cm$^{-1}$:

3300, 3060, 2960, 2930, 2870, 2600, 2480, 1900, 1705, 1635, 1590, 1555, 1540, 1460, 1410, 1375, 1305, 1230, 980, 830, 750, 635.

N-Propyl-10-[(2RS)-1-(1-pyrrolidinyl)-2-propyl]-2-phenothiazinecarbothioamide neutral fumarate may be prepared in the following manner:

A solution of 10-[(2RS)-1-(1-pyrrolidinyl)-2-propyl]-2-phenothiazinecarbothioamide (0.9 g) and propylamine (3 cc) in absolute ethanol (18 cc) is saturated with hydrogen sulphide and the mixture is brought to a temperature in the region of 100° C. for 16 hours. After being cooled, it is concentrated to dryness under reduced pressure (30 mm Hg; 4 kPa) at 40° C. to obtain a yellow oil. This oil is purified by chromatography on a column (height: 25 cm; diameter: 2.5 cm) of silica gel (0.04-0.063 mm) under a slight excess pressure of nitrogen (40 kPa), eluting successively with methylene chloride (100 cc) and then mixture (95:5 by volume) (300 cc) of methylene chloride and methanol and collecting 50-cc fractions. Fractions 3 to 5 are combined and concentrated to dryness under reduced pressure (30 mm Hg; 4 kPa) at 40° C. The residual yellow oil (1 g) is dissolved in ethanol (9 cc) under reflux and treated with a boiling solution of fumaric acid (0.29 g) in ethanol (5 cc). The mixture is allowed to cool and is maintained for 4 hours at a temperature in the region of 5° C. The crystals formed are drained, washed with ice-cold ethanol (2 cc) and dried under reduced pressure (5 mm Hg; 0.7 kPa) at 35° C. N-Propyl-10-[(2RS)-1-(1-pyrrolidinyl)-2-propyl]-2-phenothiazinecarbothioamide neutral fumarate (1.12 g) is thereby obtained in the form of yellow crystals, m.p. 150–152° C.

EXAMPLE 5

Fumaric acid (2.7 g) is added to a solution of N-propyl-10-[1-(1-pyrrolidinyl)-2-propyl]-2-phenothiazinecarbothioamide, L series (9.5 g) in ethanol (100 cc). The solution obtained is concentrated to dryness under reduced pressure (30 mm Hg; 4 kPa) at 40° C. The merigue-like yellow residue is taken up with acetic acid (200 cc). Mercuric acetate (7.3 g) is added to the solution obtained, and the mixture is stirred for 16 hours at a temperature in the region of 20° C. The black suspension obtained is diluted with distilled water (200 cc) and filtered. The yellow filtrate is concentrated under reduced pressure (30 mm Hg; 4 kPa) at 40° C. The residue is taken up with ethyl acetate (250 cc) and distilled water (50 cc) and then treated with sodium hydroxide (d 1.33) to pH 13. The aqueous phase is separated after settling has taken place and extracted with ethyl acetate (250 cc). The organic phases are combined, washed successively with distilled water (2 × 100 cc) and with saturated aqueous sodium chloride solution (100 cc) and dried over magnesium sulphate. After filtration, the yellow filtrate is concentrated under reduced pressure (30 mm Hg; 4 kPa) at 40° C. and a crude yellow oil (9.2 g) is thereby obtained. This residue is purified by chromatography on a column (height: 22 cm; diameter: 4 cm) of silica gel (0.2-0.063 mm), eluting with a mixture (95:5 by volume) of methylene chloride and methanol. The first 1,500 cc are discarded and the next 1,500 cc are concentrated under reduced pressure (30 mm Hg; 4 kPa) at 40° C. to give N-propyl-10-[1-(1-pyrrolidinyl)-2-propyl]-2-phenothiazinecarboxamide, L series (7.3 g) in the form of a yellow gum.

$[\alpha]^{20}_D = +23.4 \pm 12°$ C. (0.4%; methanol).

A 3 3 N solution (6.2 cc) of hydrochloric acid in isopropyl ether is added dropwise in the course of 5 minutes to a solution of N-propyl-10-[1-(1-pyrrolidinyl)-2-propyl]-b 2-phenothiazinecarboxamide, L series (7.2 g) in anhydrous ethyl acetate (80 cc). The product deposits on the walls and crystallizes on scratching. The suspension obtained is maintained for one hour at a temperature in the region of 5° C. The solid is drained, washed with anhydrous ethyl acetate (3 × 5 cc) and dried under reduced pressure (5 mm Hg; 0.7 kPa) at 40° C. to give N-propyl-10-[1-(1-pyrrolidinyl)-2-propyl]-2- phenothiazinecarboxamide hydrochloride, L series (7.1 g) in the form of a white solid, m.p. 190° C.

$[\alpha]^{20}{}_D = +19.4 \pm 0.6°$ (0.85%,dimethylformamide).

Proton NMR (250 MHz, DMSO, δ in ppm, J in Hz): 0.9 (T, J=7.5, 3H, —CH$_2$—CH$_3$); 1.57 (Mt, 2H, —CH$_2$CH$_3$); 1.79 (D, J=7, 3H, —CH$_3$); 1.75 to 2 (Mt, 4H, pyrrolidine —CH$_2$—CH$_2$—); 2.85, 3.10, 3.60 and 3.75 (4Cx of 1H each, pyrrolidine

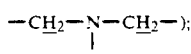

3.24 (Mt, 2H, —CONH-CH$_2$—); 3.77 (AB, 2H, >N—CH$_2$); 4.76 (Mt, 1H, >N—CH<); 7 to 7.4 (Mt, 5H, aromatic); 7.53 (S, 1H, —H at 1-position); 7.55 (D, J=8, 1H, —H at 3-position); 8.66 (T, J=5.5, 1H, —CONH—); 10.7 (Cx, 1H, —NH$^+$).

Infrared spectrum (KBr), characteristic bands in cm$^{-1}$.

3260, 3060, 2965, 2935, 2880, 2670, 2570, 2470, 1645, 1595, 1535, 1465, 1415, 1380, 1360, 1235, 875, 835, 755.

N-Propyl-10-[1-(1-pyrrolidinyl)-2-propyl]-2-phenothiazinecarbothioamide, L series may be prepared in the following manner:

A mixture of 10-[1-(1-pyrrolidinyl)-2-propyl]-2-phenothiazinecarbothioamide (L series) (10.3 g) and propylamine (32 cc) in ethanol (150 cc) is saturated with hydrogen sulphide and then heated for 16 hours to 105° C. in an autoclave. After being cooled, the solution is concentrated to dryness under reduced pressure (30 mm Hg; 4 kPa) at 40° C. An orange oil (10.2 g) is obtained, which is purified by chromatography on a column of silica (0.2–0.063 mm) (diameter: 4 cm; height: 25 cm), eluting with a 95:5 (by volume) mixture (2 liters) of methylene chloride and methanol and collecting 100-cc fractions. Fractions 13 to 17 are combined and concentrated under reduced pressure (30 mm Hg; 4 kPa) at 40° C. N-Propyl-10-[1-(1-pyrrolidinyl)-2-propyl]-2-phenothiazinecarbothioamide, L series (9.5 g) is obtained in the form of a yellow oil.

$[\alpha]^{20}{}_D = +30.4 \pm 0.6°$ (1%; methanol).

10-[1(1-Pyrrolidinyl)-2-propyl]-2-phenothiazinecarbothioamide, L series may be prepared in the following manner:

A mixture of 10-[1-(1-pyrrolidinyl)-2-propyl]-2-phenothiazinecarbonitrile, L series (11.2 g) and triethylamine (4.7 cc) in anhydrous pyridine (225 cc) is saturated by bubbling in hydrogen sulphide for one hour at 25° C. The mixture is stirred for 20 hours at 25° C. The reaction mixture is outgassed by bubbling through nitrogen and diluted with ethyl acetate (500 cc) and washed with distilled water (500 cc). The aqueous phase is extracted again with ethyl acetate (250 cc). The combined organic phases are washed with water (2×200 cc) and saturated aqueous sodium chloride solution (200 cc), dried over magnesium sulphate and concentrated under reduced pressure (30 mm Hg; 4 kPa) at 40° C. An orange oil (14.4 g) is obtained, which is purified by chromatography [on a column of silica (0.2–0.063 mm) (diameter: 4 cm; height: 30 cm), eluting with a 95:5 (by volume) mixture (3 liters) of methylene chloride and methanol and collecting 120-cc fractions. Fractions 12 to 27 are combined and concentrated under reduced pressure (30 mm Hg; 4 kPa) at 40° C. 10-[1-(1-Pyrrolidinyl)-2-propyl]-2-phenothiazinecarbothioamide, L series (10.3 g) is obtained in the form of an orange product of meringue-like consistency.

$[\alpha]^{20}{}_D = -43 \pm 0.7°$ (1%; chloroform).

10-[1-(1-Pyrrolidinyl)-2-propyl]-2-phenothiazinecarbonitrile, L series may be prepared in the following manner:

A mixture of 2-(2-cyano-10-phenothiazinyl)-1-propyl methanesulphonate, L series (25 g) and pyrrolidine (26.6 cc) in toluene (250 cc) is heated for 55 hours to a temperature in the region of 90° C.: The reaction mixture is concentrated to dryness under reduced pressure (30 mm Hg; 4 kPa) at 40° C. The residue is taken up with ethyl ether (500 cc) and extracted with a 2 N aqueous solution (2×100 cc) of methanesulphonic acid. The aqueous phases is alkalinized with caustic soda solution at a temperature in the region of 5° C. and extracted with ethyl ether (2×250 cc). The combined organic phases are washed successively with ethyl ether (100 cc). The combined organic phases are washed successively with distilled water (100 cc) and with saturated aqueous sodium chloride solution (100 cc), dried over magnesium sulphate and filtered, and the yellow filtrate is concentrated to dryness under reduced pressure (30 mm Hg; 4 kPa) at 40° C. The orange oil (17.1 g) thereby obtained is chromatographed on a column (height: 45 cm; diameter: 4 cm) of silica gel (0.063–0.2 mm), eluting with a mixture (95:5 by volume) (1 liter) of methylene chloride and methanol and collecting 100-cc fractions. Fractions 3 to 7 are combined and concentrated to dryness under reduced pressure (30 mm Hg; 4 kPa) at 40° C. 10-[1-(1-Pyrrolidinyl)-2-propyl]-2-phenothiazinecarbonitrile, L series (11.2 g) is thereby obtained in the form of a yellow oil.

$[\alpha]^{20}{}_D = +9.7 \pm 0.3°$ (1.2%; chloroform).

2-(2-Cyano-10-phenothiazinyl)-1-propyl methanesulphonate, L series may be prepared in the following manner:

Triethylamine (10 cc) is added with stirring to a solution, cooled to a temperature in the region of 5° C., of 10-(1-hydroxy-2-propyl)-2-phenothiazinecarbonitrile, L series (12.6 g) in methylene chloride (126 cc), a solution of methanesulphonyl chloride (5.6 cc) in methylene chloride (56 cc) is then added dropwise during 25 minutes, and stirring is continued for 1 hour 15 minutes at a temperature in the region of 10–15° C. The reaction mixture is washed successively with distilled water (2×100 cc) and with saturated sodium chloride solution (100 cc), dried over magnesium sulphate, filtered and concentrated to dryness under reduced pressure (30 mm Hg; 4 kPa) at 40 C. 2-(2-cyano-10-phenothiazinyl)-1-propyl methanesulphonate, L series (16.2 g) is thereby obtained in the form of an orange oil.- ($[\alpha]^{20}{}_D = +29.9 \pm 0.3°$; 2.4%; chloroform), which is used without further purification for the next stage of the synthesis.

10-(1-Hydroxy-2-propyl)phenothiazinecarbonitrile, L series may be prepared in the following manner:

A 1.97 M alcoholic solution (84.9 cc) of potassium hydroxide is added to a solution of (+)-2-(2-cyano-10-phenothiazinyl)prop-vl (R)-1-phenylethylammonium phthalate (42 g) in ethanol (420 cc) under reflux, and refluxing is continued with stirring for 15 minutes The reaction mixture is then poured onto crushed ice (500 g) and extracted with ethyl acetate (500 cc and then 2×250 cc). The organic phases are combined, washed successively with 0.5 N aqueous hydrochloric acid solution (200 cc), with 0.1 N aqueous hydrochloric acid solution (100 cc), with saturated aqueous sodium hydrogen carbonate solution (2×250 cc) and with saturated aqueous sodium chloride solution (100 cc), dried over magnesium sulphate, filtered and concentrated to dryness under reduced pressure (30 mm Hg; 4 kPa) at 40° C. The residual yellow solid is taken up with isopropyl ether (100 cc), ground, drained, washed with isopropyl ether (10 cc) and dried under reduced pressure (5 mm Hg; 0.7 kPa) at 40° C. 10-(1-Hydroxy-2-propyl)-2-phenothiazinecarbonitrile, L series (17.8 g) is thereby obtained in the form of yellow crystals, m.p. 136° C.

[α]$^{20}_D$ = −13±0.4° (1.2%; chloroform).

(+)-2-(2-Cyano-10-phenothiazinyl)propyl (1R)-1-phenylethylammonium phthalate may be prepared in the following manner:

A suspension of 10-[(2RS)-1-hydroxy-2-propyl]-2-phenothiazinecarbonitrile (56.5 g) and phthalic anhydride (32.6 g) in anhydrous pyridine (100 cc) is brought to reflux for 6 hours with stirring. After being cooled, the reaction mixture is diluted with methylene chloride (500 cc), washed with distilled water (4×100 cc), dried over magnesium sulphate, filtered and concentrated to dryness under reduced pressure (30 mm Hg; 4 kPa) at 40° C. The residue is stirred with N aqueous hydrochloric acid solution (500 cc) and then separated after settling has taken place and dissolved in ethyl acetate (500 cc). The solution is washed with N aqueous hydrochloric acid solution (2×100 cc) then with aqueous sodium chloride solution (100 cc). The organic phase is dried over magesium sulphate, filtered and concentrated to dryness under reduced pressure (30 mm Hg; 4 kPa) at 50° C. A thick oil (102 g) containing 2-{[(2RS)-2-(2-cyano-10-phenothiazinyl)-1-propyl]oxycarbonyl}benzenecarboxylic acid is thereby obtained, and is subsequently used as it is.

The oil (102 g) obtained above and containing 2-{[(2RS)-2-(2-cyano-10-phenothiazinyl)-1-propyl]oxycarbonyl}benzenecarboxylic acid is dissolved in ethyl acetate (500 cc) and a solution of (1S)-(−)-1-phenylethylamine (24.2 g) in ethyl acetate (360 cc) is added with stirring at a temperature in the region of 20° C. After 2 days, stirring at a temperature in the region of 20° C., the solid formed is filtered off and kept.

The filtrate is concentrated to dryness under reduced pressure (30 mm Hg; 4 kPa) at 40° C. The residue is taken up with N aqueous hydrochloric acid solution (500 cc) and extracted with ethyl acetate (2×250 cc). The combined organic phases are concentrated to dryness under reduced pressure (30 mm Hg; 4 kPa) at 40° C. The residue (50 g) is dissolved in ethyl acetate (500 cc) and (1R)-(+)-1-phenylethylamine (14 g) is added. After 16 hours, stirring at a temperature in the region of 20° C., the solid formed is drained and dissolved in ethyl acetate (450 cc) under reflux. After cooling, the solid formed is drained, washed with ethyl acetate (40 cc) and dried under reduced pressure (50 mm Hg; 4 kPa) at 40.C (+)-2-(2-Cyano-10-phenothiazinyl)propyl (1R)-1-phenylethylammonium phthalate (44.3 g) is thereby obtained in 5 the form of pale yellow crystals, m.p. 154-155° C.

[α]$^{20}_D$ = +20.8±0.5° (1.1%; chloroform).

EXAMPLE 6

Mercuric aoetate (1.81 g) dissolved in glacial acetic acid (35 cc) is added in the course of 20 minutes to a solution of 10-[(2RS)-1-(perhydro-1-azepinyl)-2-propyl]-N-propyl-2-phenothiazinecarbothioamide (2.5 g) in acetic acid (25 cc), and the mixture is stirred for 45 minutes at a temperature in the region of 20° C. The black suspension obtained is filtered on sintered glass plugged with celite, and the yellow filtrate is concentrated under reduced pressure (30 mm Hg; 4 kPa) at 40° C. The residue is taken up with ethyl acetate (250 cc) and distilled water (50 cc). The organic phase is washed successively with normal sodium hydroxide (2×100 cc) and distilled water (3×100 cc) and with saturated aqueous sodium chloride solution (100 cc) and dried over magnesium sulphate. After filtration, the yellow filtrate is concentrated under reduced pressure (30 mm Hg; 4 kPa) at 40° C. and a crude yellow oil (2.1 g) is thereby obtained This residue is taken up with boiling isopropyl ether (80 cc). The small amount of insoluble matter is removed by filtration and crystallization is primed in the filtrate by cooling maintained with stirring. The crystals are filtered off on sintered glass to give 10-[(2RS)-1-(perhydro-1-azepinyl)-2-propyl]-N-propyl-2-phenothiazinecarboxamide (1.29 g) in the form of an offwhite solid, m.p. 113° C.

Proton NMR (250 MHz, DMSO, δ in ppm, J in Hz):
0.9 (T, J=7.5, 3H, propyl —CH$_3$); 1.48 (Cx, 8H, perhydroazepinyl —CH$_2$—); 1.52 (mt, 2H, —CH$_2$CH$_2$CH$_3$); 1.6 (D, J=7, 3H, —CH$_3$); 2.56 (Mt, approximately 4H,

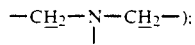

2.78 (DD, J=14 and 6, 1H, 1H of >N—CH$_2$—); 3.06 (DD, J=14 and 6, 1H, 1H of >N—CH$_2$—); 3.06 (DD, J=14 and 7.5, 1H, 1H of >N—CH$_2$—); 3.22 (Mt, 2H, —CONH—CH$_2$—); 4.12 (Mt, J=7.5, 7 and 6, 1H, N-CH); 6.9 to 7.25 (Mt, 5H, aromatic); 7.4 (broad D, J=8, 1H, —H at 3-position); 7.52 (broad S, 1H, —H at 1-position); 8.44 (T, J =5.5, 1H, —CONH—).

Infrared spectrum (KBr), characteristic bands in cm$^{-1}$:
3450, 3370, 3060, 2960, 2930, 2880, 2860, 2820, 1650, 1595, 1555, 1520, 1460, 1410, 1380, 1310, 1230, 820.

10-[(2RS)-1-(Perhydro-1-azepinyl)-2-propyl]-N-propyl-2-phenothiazinecarbothioamide may be obtained in the following manner:

n-Propylamine (3.3 cc) is added to a solution of -[(2RS)-1-(perhydro-1-azepinyl)-2-propyl]-2-phenothiazinecarbothioamide (3.2 g) in absolute ethanol (80 cc). The mixture is saturated with hydrogen sulphide and then brought to 150° C. for 16 hours. The reaction mixture is concentrated to dryness under reduced pressure (30 mm Hg; 4 kPa). The residue is diluted with ethyl 5 acetate (150 cc), washed with distilled water (3×100 cc) and with saturated sodium chloride solution (100 cc), dried over magnesium sulphate and then concentrated to dryness under reduced pressure (30 mm Hg; 4 kPa) before being purified by chromatography on a column (height: 32 cm; diameter: 4 cm) of silica gel (0.06–0.2 mm), eluting with a 60:40 (by volume) mixture (1,000 cc) of cyclohexane and ethyl acetate, collecting 60-cc fractions. Fractions 3 to 11 are combined and concentrated to dryness at 50° C. under reduced pressure (30 mm Hg; 4 kPa) to give 10-[(2RS)-1-(perhydro-1-azepinyl)-2-propyl]-N-propyl-2-phenothiazinethiocarboxamide (2.5 g) in the form of a clear orange oil.

10-[(2RS)-1-(Perhydro-1-azepinyl)-2-propyl]-2-phenothiazinecarbothioamide may be obtained in the following manner:

A mixture of 10-[(2RS)-1-(perhydro-1-azepinyl)-2-propyl]-2-phenothiazinecarbonitrile (7.1 g) and triethylamine (2.74 cc) in anhydrous pyridine (75 cc) is saturated by bubbling in hydrogen sulphide for 5 hours at 25° C. The clear solution obtained is kept stirred for 12 hours at 25° C., and outgassed by bubbling through nitrogen for 1 hour. The reaction mixture is diluted with ethyl acetate (150 cc) and washed with distilled water (6 × 100 cc) and with saturated sodium chloride solution (3 × 120 cc). The organic phase is dried over magnesium sulphate and filtered and the filtrate is concentrated to dryness under reduced pressure (30 mm Hg; 4 kPa). The residue is purified by chromatography on a column of silica gel (0.06–0.2 mm) (height: 29 cm; diameter: 4.5 cm), eluting with mixtures of cyclohexane and ethyl acetate in proportions (by volume) 30:70 (1 liter) and 40:60 (2 liters) and collecting 250-cc fractions. Fractions 4 to 6 are combined and concentrated to dryness at 50° C. under reduced pressure (30 mm Hg; 4 kPa) to give 10[(2RS)-1-(perhydro-1-azepinyl)-2-propyl]-2-phenothiazinecarbothioamide (5.2 g) in the form of an orange product of merigue-like consistency.

10-[(2RS)-1-(Perhydro-1-azepinyl)-2-propyl]-2-phenothiazinecarbonitrile may be prepared in the following manner:

A suspension of (2RS)-2-(2-cyano-10-phenothiazinyl)-1-propyl mesylate (9 g) in hexamethylenimine (25 cc) is brought to 89° C. The mixture is maintained at this temperature for 12 hours. After being cooled, the mixture is concentrated to dryness at 50° C. under reduced pressure (30 mm Hg; 4 kPa). The residue is diluted with ethyl acetate (350 cc) and filtered and the filtrate is washed with distilled water (150 cc) and saturated sodium chloride solution (2 × 100 cc). After settling has taken place, the organic phase is separated and extracted with hydrochloric acid (350 cc) in 3 N solution. The combined acid aqueous extracts are extracted with ethyl acetate (200 cc) and then alkalinized with concentrated sodium hydroxide and extracted again with ethyl acetate (3 × 200 cc). The organic phase is washed with distilled water (2 × 200 cc) and then dried over magnesium sulphate, filtered and concentrated to dryness under reduced pressure (30 mm Hg; 4 kPa) to give a residue which is purified by chromatography on a column (height: 35 cm; diameter: 4.2 cm) of silica gel (0.06–0.2 mm), eluting with a 70:30 (by volume) mixture (500 cc) of cyclohexane and ethyl acetate and collecting 100-cc fractions. The first 200 cc are discarded and fractions 1 to 3 are combined and concentrated to dryness at 50° C. under reduced pressure (30 mm Hg; 4 kPa) to give 10-[(2RS)-1-(perhydro-1-azepinyl)-2-propyl]-2-phenothiazinecarbonitrile (7.2 g) in the form of a yellow product of meringue-like consistency.

EXAMPLE 7

A solution of mercuric acetate (0.57 g) in glacial acetic acid (9 cc) is added dropwise during a period of 10 minutes to a solution of N-butyl-10-[(2RS)-1-diethylamio-2-propyl]-2-phenothiazinecarbothioamide (0.76 g) in glacial acetic acid (9 cc). The reaction mixture is stirred for 90 minutes at 25° C. and then filtered on sintered glass covered with celite. The celite is washed with acetic acid (2 × 3 cc) and the combined filtrates are concentrated to dryness under reduced pressure (30 mm Hg; 4 kPa) at 40° C. to give a residue which is diluted in ethyl acetate (50 cc). The organic phase is washed with normal sodium hydroxide (25 cc) and distilled water (3 × 25 cc) and then with brine (1 × 25 cc), dried over magnesium sulphate, filtered and concentrated to dryness under reduced pressure (30 mm Hg; 4 kPa) at 40° C. to give a residue which is purified by chromatography on a column (height: 12 cm; diameter: 1.8 cm) of silica gel (0.04–0.06 mm) with a slight excess pressure of nitrogen (40 kPa), eluting with a 50:50 (by volume) mixture (750 cc) of cyclohexane and ethyl acetate and collecting 25-cc fractions. Fractions 5 to 25 are combined and concentrated under reduced pressure (30 mm Hg; 4 kPa) at 50° C. to give N-butyl-10-[(2RS)-1-diethylamino-2-propyl]-2-phenothiazinecarboxamide (0.68 g).

Fumaric acid (0.13 g) dissolved in 2-propanol (5 cc) under reflux is added to a solution of N-butyl-10-[(2RS)-1-diethylamino-2-propyl]-2-phenothiazinecarboxamide (0.46 g) in boiling 2-propanol (5 cc). Crystallization is primed by scratching, and the mixture is stirred for 5 hours at 25° C. The crystals are filtered off on sintered glass, washed with ice-cold 2-propanol (2 × 3 cc) and dried under reduced pressure (5 mm Hg; 0.7 kPa) to give N-butyl-10-[(2RS)-1-diethylamino-2-propyl]-2-phenothiazinecarboxamide fumarate (0.34 g), m.p. 129° C.

Proton NMR (250 MHz, DMSO, δ in ppm, J in Hz):
0.92 (Mt, 9H, —N(CH$_2$CH$_3$)$_2$ and —CH$_2$CH$_3$); 1.35 (Mt, 2H, —CH$_2$CH$_3$); 1.52 (Mt, 2H, —CH$_2$CH$_2$CH$_3$); 1.65 (D, J=7, 3H, —CH$_3$); 2.53 (masked Mt, 4H, —N(C/ CH$_3$)$_2$); 2.75 (DD, J=13 and 6, 1H, 1H of >NCH$_2$—); 3.07 (DD, J=13 and 6.5, 1H, 1H of NCH$_2$—) 3.26 (Mt, J=7 and 5.5, 2H, —CONHCH$_2$(CH$_2$)$_2$CH$_3$); 4.20 (Mt, J=7, 6.5 and 6, 1H, >N—CH<); 6.63 (S, 2H, fumarate —CH=CH—); 6.9 to 7.3 (Mt, 5H, aromatic); 7.42 (DD, J 8 and 1, 1H, -H at 3-position); 7.54 (D, J=1, 1H, —H at 1-position); 8.43 (T, J=5.5, 1H, —CONH—).

Infrared spectrum (KBr), characteristic bands in cm$^{-1}$.
3260, 3050, 2960, 2930, 2870, 2660, 2490, 1910, 1700, 1630, 1590, 1555, 1460, 1415, 1380, 1305, 1230, 985, 880, 840, 755, 635.

N-Butyl-10-[(2RS)-1-diethylamino-2-propyl]-2-phenothiazinecarbothioamide may be prepared in the following manner:

n-Butylamine (2.4 cc) is added to a solution of 10-[(2RS)-1-diethylamino-2-propyl]-2-phenothiazinecarbothioamide (1.86 g) in absolute ethanol (25 cc). The mixture is brought to 150° C. for 16 hours and then concentrated to dryness under reduced pressure (30 mm Hg; 4 kPa) at 40° C. The residue obtained is purified by chromatography on a column (height: 17 cm; diameter: 2.6 cm) of silica gel (0.04–0.06 mm) with a slight excess pressure of nitrogen (40 kPa), eluting with mixtures of cyclohexane and ethyl acetate in proportions (by volume) of 90:10 (250 cc), 80:20 (500 cc) and 50:50 (750 cc) and then with pure ethyl acetate (750 cc), collecting 50-cc fractions. Fractions 10 to 18 are combined and concentrated to dryness under reduced pressure (30 mm Hg; 4 kPa) at 40° C. to give N-butyl-10-[(2RS)-1-diethylamino-2-propyl]-2-phenothiazinecarbothioamide (0.96 g).

Proton NMR spectrum (250 MHz, DMSO, δ in ppm, J in Hz):
1.37 (Mt, 2H, —(CH$_2$)$_2$—CH$_2$—CH$_3$); 1.69 (Mt, 2H, —CH$_2$—CH$_2$—CH$_3$); 3.70 (Mt, 2H, —CSNH—CH$_2$); 7 to 7.35 (Mt, 5H, aromatic).

EXAMPLE 8

N-Butyl-10-[(2RS)-1-(N-ethyl-N-methylamino)-2-propyl]-2-phenothiazinecarbothioamide (0.6 g) is dissolved in a solution of fumaric acid (0.17 g) in ethanol (10 cc) and the mixture is then concentrated to dryness under reduced pressure (30 mm Hg; 4 kPa) at 40° C.

The residual orange product (0.77 g) of meringue-like consistency is taken up with acetic acid (10 cc), mercuric acid (0.48 g) is added and the orange suspension obtained is stirred for 2 hours at a temperature in the region of 20° C. The black suspension obtained is concentrated to dryness under reduced pressure (30 mm Hg; 4 kPa) at 60° C. and the residue is taken up with distilled water (15 cc). The mixture is filtered and the solid washed with distilled water (5 cc). The filtrate and the washing liquor are combined and alkalinized with caustic soda solution (d = 1.33) to pH 13. The mixture is extracted with ethyl acetate (2 × 10 cc) and the combined organic phases are washed with saturated aqueous sodium chloride solution (10 cc), dried over magnesium sulphate, filtered and concentrated to dryness under reduced pressure (30 mm Hg; 4 kPa) at 40° C. The residual orange oil (0.5 g) is dissolved in the minimum amount of ethyl acetate (3.6 cc) and isopropyl ether (28.5 cc) is added, followed, with stirring, by a 0.3 N solution (4 cc) of hydrochloric acid in isopropyl ether. Stirring is continued for 30 minutes at a temperature in the region of 5° C. The precipitate formed is drained, washed with isopropyl ether (3 × 4 cc) and dried under reduced pressure (5 mm Hg; 0.7 kPa) at 40° C. N-Butyl-10-[(2RS)-1-(N-ethyl-N-methylamino)-2propyl]-2-phenothiazinecarboxamide hydrochloride (0.4 g) is thereby obtained in the form of a beige solid, m.p. 130–135° C. (melts forming a paste).

Proton NMR (250 MHz, in DMSO, δ in ppm, J in Hz):

0.9 (T, J=7, J=7, 3H, -CH$_2$CH.); 1.32 (Mt, 2H, —CH$_2$—CH$_3$; 1.51 Mt, 2H, —CH$_2$CH$_2$CH$_3$); 1.8 (D, J=7, 3H, CH$_3$); 2.73 (S, 3H, >N—CH$_3$); 3.25 (Mt, 2H, —CONH—CH$_2$—); 4.8 (Mt, 1H, N-CH); 7 to 7.4 (Mt, 5H, aromatic); 7.51 (S, 1H, —H at 1-position); 7.53 (D, J=8, 1H, —H at 3-position); 8.62 (Cx, 1H, —CONH—); 10.45 (Cx, 1H, NH$^+$).

Infrared spectrum (KBr), characteristic bands in cm$^{-1}$:

3280, 3060, 2960, 2930, 2870, 2660, 2600, 2580, 1640, 1590, 1540, 1460, 1415, 1380, 1310, 1230, 870, 845, 830, 755.

N-Butyl-10-[(2RS)-1-(N-ethyl-N-methylamino)-2-propyl]-2-phenothiazinecarbothioamide may be prepared in the following manner:

A mixture of 10-[(2RS)-1-(N-ethyl-N-methylamino)-2-propyl]-2-phenothiazinecarbothioamide (2.1 g) and butylamine (8.5 cc) in absolute ethanol (30 cc) is saturated with hydrogen sulphide and heated for 16 hours to a temperature in the region of 100° C. After being cooled, the orange solution obtained is concentrated to dryness under reduced pressure (30 mm Hg; 4 kPa) at 40° C. The residual brown oil is purified by chromatography on a column (height: 4 cm; diameter: 3 cm) of silica gel (0.2–0.063 mm), eluting successively with methylene chloride (2 liters) and with a mixture (90:10 by volume) (1 liter) of methylene chloride and methanol and collecting 60-cc fractions. Fractions 36 to 39 are combined and concentrated to dryness under reduced pressure (30 mm Hg; 4 kPa) at 40° C. The residual orange oil (1.8 g) is again purified by chromatography on a column (height: 25 cm; diameter: 4 cm) of silica gel (0.04–0.063 cm) under a slight excess pressure of nitrogen (40 kPa), eluting with a mixture (75:25 by volume) (1 liter) of ethyl acetate and cyclohexane and collecting 60-cc fractions. Fractions 5 to 12 are combined and concentrated to dryness under reduced pressure (30 mm Hg; 4 kPa) at 40° C. N-Butyl-10-[(2RS)-1-(N-ethyl-N-methylamino)-2-propyl]-2-phenothiazinecarbothioamide (1.25 g) is thereby obtained in the form of a yellow oil.

10-[(2RS)-1-(N-Ethyl-N-methylamino)-2-propyl]-2-phenothiazinecarbothioamide may be prepared in the following manner:

A solution of 10-[(2RS)-1-(N-ethyl-N-methyl-amino)-2-propyl]-2-phenothiazinecarbonitrile (3 g) and triethylamine (1.3 cc) in anhydrous pyridine (60 cc) is treated with excess hydrogen sulphide, and stirring is then continued for 16 hours at a temperature in the region of 20° C. The solution obtained is purged with a stream of nitrogen for 1 hour, poured into ethyl acetate (100 cc), washed with distilled water (3 × 200 cc), dried over magnesium sulphate, filtered and concentrated to dryness under reduced pressure (30 mm Hg; 4 kPa) at 40° C. The residual brown oil is purified by chromatography on a column (height: 40 cm; diameter: 3 cm) of silica gel (0.2–0.06 mm), eluting successively with methylene chloride (1 liter), a mixture (95:5 by volume) (1 liter) of methylene chloride and methanol and a mixture (80:20 by volume) (3 liters) of methylene chloride and methanol, and collecting 150-cc fractions. Fractions 26 to 30 are combined and concentrated to dryness under reduced pressure (30 mm Hg; 4 kPa) at 40° C. 10-[(2RS)-1-(N-Ethyl-N-methylamino)-2-propyl]-2-phenothiazinecarbothioamide (2.15 g) is thereby obtained in the form of an orange oil.

10-[(2RS)-1-(N-Ethyl-N-methylamino)-2-propyl]-2-phenothiazinecarbonitrile may be prepared in the following manner:

A mixture of 10-[(2RS)-1-ethylamino-2-propyl]-2-phenothiazinecarbonitrile (4.4 g), sodium carbonate (2.25 g) and iodomethane (0.9 cc in dimethylformamide (60 cc) is heated for 6 hours to a temperature in the region of 150° C. The reaction mixture is then concentrated to dryness under reduced pressure (5 mm Hg; 0.7 kPa) at 40° C. and the residue is taken up with distilled water (100 cc) and extracted with ethyl acetate (2 × 100 cc). The combined organic phases are extracted with N aqueous hydrochloric acid solution (2 × 50 cc). The combined aqueous phases are alkalinized with sodium hydroxide (d = 1.33) to pH 13 and extracted with ethyl acetate (2 × 100 cc). The combined organic phases are washed successively with distilled water (50 cc) and with saturated aqueous sodium chloride solution (50 cc), dried over magnesium sulphate, filtered and concentrated to dryness under reduced pressure (30 mm Hg; 4 kPa) at 40° C. 10-[(2RS)-1-(N-Ethyl-N-methylamino)-2-propyl]-2-phenothiazinecarbonitrile (3 g) is thereby obtained in the form of an orange oil.

10-[(2RS)-1-Ethylamino-2-propyl]-2-phenothiazinecarbonitrile may be prepared in the following manner:

A solution of (2RS)-2-(2-cyano-10-pheno thiazinyl)-propyl methanesulphonate (50 g) and ethylamine (100 cc) in toluene (600 cc) is heated for 24 hours to a temperature in the region of 105° C. After being cooled, the mixture is concentrated to dryness under reduced pressure (30 mm Hg; 4 kPa) at 40° C. The residue is taken up with distilled water (250 cc) and the mixture is extracted successively with ethyl acetate (500 cc and 250 cc). The combined organic phases are extracted with N aqueous hydrochloric acid solution (2 × 500 cc). The aqueous phases are alkalinized with caustic soda solution (d = 1.33) to pH 13 and extracted successively with ethyl acetate (500 cc and 250 cc). The combined organic phases are washed with saturated aqueous sodium chloride solution (250 cc), dried over magnesium sulphate, filtered and concentrated to dryness under reduced pressure (30 mm Hg; 4 kPa) at 40° C. 10-[(2RS)-1-Ethylamino-2-propyl]-2phenothiazinecarbonitrile (30.4 g) is thereby obtained in the form of an orange oil.

EXAMPLE 9

A suspension of N-butyl-10-[(2RS)-1-(1-pyrrolidinyl)-2-propyl]-2-phenothiazinecarbothioamide (1.2 g) and mercuric acetate (1 g) in acetic acid (15 cc) is stirred for 5 hours at a temperature in the region of 20° C. The black suspension obtained is diluted with ethyl ether (25 cc) and filtered. The solid is washed with ethyl ether (2×10 cc). The combined organic phases are concentrated to dryness under reduced pressure (30 mm Hg; 4 kPa) at 50° C. The residue is taken up with ethyl acetate (25 cc) and distilled water (25 cc). The organic phase is separated, filtered, dried over magnesium sulphate, filtered again and concentrated to dryness under reduced pressure (30 mm Hg; 4 kPa) at 40° C. The very viscous residual oil (1.1 g) is taken up with a mixture (83:17 by volume) (12 cc) of ethyl acetate and methanol warmed to about 50° C. After 1 hour at a temperature in the region of 20° C., the solid formed is drained, washed with diethyl ether (2×10 cc) and dried under reduced pressure (5 mm Hg; 0.7 kPa) at 40° C. N-butyl-10-[(2RS)-1-(1-pyrrolidinyl)-2-propyl]-2-phenothiazinecarboxamide (0.4 g) is thereby obtained in the form o cream-coloured crystals, m.p. 218° C.

Proton NMR (250 MHz, CDCl:, 27° C., δ in ppm, J in Hz):

0.97 (T, J=7.5, 3H, N-butyl —CH$_3$); 1.43 (Mt, 2H, —CH$_2$—CH$_3$); 1.64 (Mt, 2H, —CH$_2$CH$_2$—CH$_3$); 1.87 (D, J=7, 3H, —CH$_3$); 2.07 (Cx, 4H, pyrrolidine —CH$_2$—CH$_2$—); 2.6 to 3.35 and 3.5 to 4.1 (extended 2Cx, 2H each, pyrrolidine

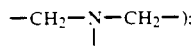

3 45 (Mt, 3H, —CONH—CH$_2$ and 1H of >N—CH$_2$—); 3.72 (DD, J=14 and 8, 1H, 1H of >NCH$_2$—); 5.24 (Mt, 1H, >N—CH<); 6.9 to 7.3 (Mt, 6H, aromatic and —CONH—); 7.39 (DD, J=8 and 1, 1H, —H at 3-position); 7.52 (D, J=1, 1H, —H at 1-position); 12.3 (extended Cx, 1H, —NH$^-$).

Infrared spectrum (KBr), characteristic bands in cm$^{-1}$:

3280, 3060, 2960, 2930, 2870, 2680, 2610, 2480, 1645, 1595, 1535, 1460, 1410, 1380, 1305, 1235, 845, 750.

N-Butyl-10-[(2RS)-1-(1-pyrrolidinyl)-2-propyl]-2-phenothiazinecarbothioamide may be prepared in the following manner:

A mixture of 10-[(2RS)-1-(1-pyrrolidinyl)-2-propyl]-2-phenothiazinecarbothioamide (1 g) and butylamine (1.5 cc) in absolute ethanol (20 cc) is saturated with hydrogen sulphide and then heated for 24 hours to a temperature in the region of 120° C. After being cooled, the reaction mixture is concentrated to dryness under reduced pressure (30 mm Hg; 4 kPa) at 40° C. The residue is taken up with distilled water (10 cc) and ethyl acetate (25 cc). After extraction, the organic phase is separated, washed with distilled water (10 cc) and then with saturated aqueous sodium chloride solution (20 cc), dried over potassium carbonate, filtered and concentrated to dryness under reduced pressure (30 mm Hg; 4 kPa) at 40° C. N-Butyl-10-[(2RS)-1-(1-pyrrolidinyl)-2-propyl]-2-phenothiazinecarbothioamide (1.15 g) is thereby obtained in the form of a viscous yellow oil which is subsequently used as it is.

EXAMPLE 10

Mercuric acetate (1.45 g) is added to a solution of N-butyl-10-[1-(1-pyrrolidinyl)-2-propyl]-2-phenothiazinecarbothioamide hydrochloride, L series (2 g) in acetic acid (40 cc), and the mixture is stirred for 16 hours at a temperature in the region of 20° C. The water (50 cc) and filtered and the yellow filtrate is concentrated under reduced pressure (30 mm Hg; 4 kPa) at 40° C. The residue is taken up with ethyl acetate (100 cc) and distilled water (50 cc) and then treated with sodium hydroxide (d 1.33) to pH 13. The organic phase is washed successively with distilled water (2×25 cc) and with saturated aqueous sodium chloride solution (25 cc) and dried over magnesium sulphate. After filtration, the yellow filtrate is concentrated to dryness under reduced pressure (30 mm Hg; 4 kPa) at 40° C., and a yellow oil (1.12 g) is thereby obtained. This product is purified by chromatography on a column (height: 30 cm; diameter: 1 cm) of silica gel (0.2-0.063 mm), eluting with a mixture (95:5 by volume) of methylene chloride and methanol and collecting 20-cc fractions. Fractions 7 to 19 are combined and concentrated to dryness under reduced pressure (30 mm Hg; 4 kPa) at 40° C. A yellow gum (0.63 g) is obtained. This product is dissolved in a mixture of ethyl acetate (2.5 cc) and isopropyl ether (40 cc) and treated with a 3.3 N solution (0.45 cc) of hydrochloric acid in isopropyl ether. The precipitate formed is drained, washed with isopropyl ether (3×2 cc) and dried at 40° C. under reduced pressure (5 mm Hg; 0.7 kPa). N-Butyl-10-[1-(1-pyrrolidinyl)-2-propyl]-2-phenothiazinecarboxamide hydrochloride, L series (0.35 g) is thereby obtained in the form of a while solid, m.p. 200° C.

$[\alpha]^{20}_D = +14.7 \pm 1°$ (0.5%, dimethylformamide).

Proton NMR (250 MHz, DMSO, δ in ppm, J in Hz):

0.92 (T, J=7, 3H, N-butyl —CH$_3$); 1.35 (Mt, 2H, —CH$_2$—CH$_3$); 1.53 (Mt, 2H, —CH$_2$CH$_2$CH$_3$); 1.8 (D, J=6.5, 3H, —CH$_3$); 1.7 to 2 (Mt, 4H, —CH$_2$—CH$_2$—); 2.8, 3.1, 3.6 and 3.75 (4Mt, 1H each, —CH$_2$—N—CH$_2$—); 3.28 (Mt, 2H, —CONH—CH$_2$); 3.6 to 3.9 (Mt, 2H, >N—CH$_2$—); 4.68 (Mt, 1H, >N—CH<); 7 to 7,4 (Mt, 5H, aromatic); 7.52 (S, 1H, —H at 1-position); 7.54 (D, J=8, 1H, —H at 3-position); 8.58 (T, J=5.5, 1H, —CONH—); 10.2 (Cx, 1H, —NH$^-$).

Infrared spectrum (KBr), characteristic bands in cm$^{-1}$:

3270, 3060, 2950, 2930, 2865, 2670, 2580, 2470, 1645, 1590, 1535, 1460, 1410, 1380, 1305, 1230, 845, 755.

N-Butyl-10-[1-(1-pyrrolidinyl)-2-propyl]-2-phenothiazinecarbothioamide hydrochloride, L series may be prepared in the following manner:

Butylamine (9.6 cc) is added to a solution of 10-[1-(1-pyrrolidinyl)-2-propyl]-2-phenothiazinecarbothioamide, L series (3.7 g) in absolute ethanol (55 cc), and this solution is saturated with hydrogen sulphide. The mixture is then brought to a temperature in the region of 105° C. for 16 hours. After being cooled, the solution is concentrated to dryness under reduced pressure (30 mm Hg; 4 kPa) at 40° C. An orange oil is obtained, which is purified by chromatography under slight excess pressure of nitrogen (40 kPa) on a column (height: 25 cm; diameter: 4 cm) of silica gel (0.2-0.063 mm), eluting with a mixture (70:30 by volume) (1 liter) of ethyl acetate and cyclohexane and collecting 60-cc fractions. Fractions 7 to 12 are combined and concentrated to dryness under reduced pressure (30 mm Hg; 4 kPa) at 40° C. An orange oil (3.4 g) is thereby obtained. This product is dissolved in isopropyl ether (150 cc) and a 3.3 N solution (2.4 cc) of hydrochloric acid in isopropyl ether is added. The precipitate formed is drained, washed with isopropyl (3×10 cc) and dried at 40° C. under reduced pressure (5 mm Hg; 0.7 kPa). N-Butyl-10-[1-(1-pyrrolidinyl)2-propyl]-2-phenothiazinecarbothioamide hydrochloride, L series (3.16 g) is obtained in the form of a yellow solid, m.p. 125-130° C. (melts forming a paste).

$[\alpha]^{20}_D = +27.5 \pm 0.6°$ (1%; dimethylformamide).

Proton NMR (250 MHz, CDCl$_3$, δ in ppm, J in Hz): 1 (T, J=7.5, 3H, butyl —CH$_3$); 1.49 (Mt, 2H, —CH$_2$CH$_3$); 1.85 (D, J 7, 3H, —CH$_3$); 1.86 (Mt, 2H, —C$\overline{H}_2$—CH$_2$CH$_3$); 1.9 to 2.25 (Mt, 4H, pyrrolidine —C$\overline{H}_2$—CH$_2$—); 2.82, 2.98, 3.85 and 4.08 (4Cx, 1H each, pyrrolidine

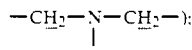

3.45 (broad D, J=13, 1H, 1H of >N—CH$_2$—); 3.65 to 3.95 (Mt, 3H, other H of >N—CH$_2$— and —CSNH—CH$_2$—); 5.6 (Mt, 1H, >CH—<); 6.9 to 7.25 (Mt, 5H, aromatic); 7.33 (D, J=1, 1H, —H at 1-position); 7.5 (DD, J=8 and 1, 1H, —H at 3-position); 8.93 (Cx, 1H, —CSNH—); 12.25 (Cx, 1H, —NH$^+$).

EXAMPLE 11

A solution of mercuric acetate (0.84 g) in glacial acetic acid (13 cc) is added dropwise during a period of 10 minutes to a solution of 10-[(2RS)-1-diethylamino-2-propyl]-N-(2-methylpropyl)-2-phenothiazinecarbothioamide (1.12 g) in glacial acetic acid (13 cc). The reaction mixture is stirred for 90 minutes at 25° C. and then filtered on sintered glass covered with celite. The celite is washed with acetic acid (2 cc) and the combined filtrates are concentrated to dryness under reduced pressure (30 mm Hg; 4 kPa) at 40° C. to give a residue which is then diluted in ethyl acetate (50 cc). The organic phase is washed with normal caustic soda solution (25 cc) and distilled water (3×25 cc) and then with brine (1×25 cc), dried over magnesium sulphate, filtered and concentrated to dryness under reduced pressure (30 mm Hg; 4 kPa) at 40° C. to give a residue which is purified by chromatography on a column (height: 17.2 cm; diameter: 2.4 cm) of silica gel (0.04-0.06 mm) with a slight excess pressure of nitrogen (40 kPa), eluting with a 50:50 (by volume) mixture (1 liter) of cyclohexane and ethylacetate, collecting 60-cc fractions. Fractions 4 to 14 are combined and concentrated to dryness under reduced pressure (30 mm Hg; 4 kPa) at 40° C. to give 10-[(2RS)-1-diethylamino-2-propyl]-N-(2-methylpropyl)-2-phenothiazinecarboxamide (0.83 g).

Fumaric acid (0.18 g) dissolved in 2-propanol (7.5 cc) under reflux is added to a solution of 10-[(2RS)-1-diethylamino-2-propyl]-N-(2-methylpropyl)-2-phenothiazinecarboxamide (0.62 g) in boiling 2-propanol (7.5 cc). The mixture is concentrated to dryness under reduced pressure (30 mm Hg; 4 kPa) at 40° C. and the residue is stirred in isopropyl ether (50 cc). The solid is separated by filtration on sintered glass, washed with isopropyl ether (10 cc) and dried under reduced pressure (5 mm Hg; 0.7 kPa) to give 10-[(2RS)-1-diethylamino-2-propyl]-N-(2-methylpropyl)-2-phenothiazinecarboxamide fumarate (0.64 g), m.p. 110° C.

Proton NMR (250 MHz, DMSO, δ in ppm, J in Hz): 0.9 (Mt, 12 H, —N(CH$_2$CH$_3$)$_2$ and —CH(CH$_3$)$_2$); 1.65 (D, J=7, 3H, —CH:); 1.84 (Mt, 1H, —CH(C$\overline{H}_3$)$_2$); 2.58 (Mt, 4H, —N(CH$_2$CH$_3$)$_2$); 2.8 (DD, J=$\overline{14}$ and 5.5, 1H, 1H of >NCH$_2$—); 3.07 (Mt, 2H, —CONH—CH$_2$—); 3.10 (DD, J=14 and 7.5, 1H >N—CH$_2$—); 4.2$\overline{5}$ (Mt, J=7.5, 7 and 5.5, 1H, N—CH); 6.57 (S, 2H, fumarate —CH=CH—); 6.9 to 7.3 (Mt, 5H, aromatic); 7.42 (D, J=8, 1H, —H at 3-position); 7.52 (S, 1H, —H at 1-position); 8.46 (T, J=5.5, 1H, —CONH—).

Infrared spectrum (KBr), characteristic bands in cm$^{-1}$.

3300, 3060, 2950, 2920, 2865, 2620, 2500, 1900, 1705, 1635, 1590, 1555, 1540, 1460, 1410, 1380, 1310, 1230, 980, 870, 825, 750, 635.

10-[(2RS)-1-Diethylamino-2-propyl]-N-(2-methylpropyl)-2-phenothiazinecarbothioamide may be prepared in the following manner:

Isobutylamine (2.50 cc) is added to a solution of 10-[(2RS)-1-diethylamino-2-propyl]-2-phenothiazinecarbothioamide (1.86 g) in absolute ethanol (25 cc). The mixture is brought to 150° C. for 16 hours and then concentrated to dryness under reduced pressure (30 mm Hg; 4 kPa) at 50° C. The residue obtained is purified by chromatography on a column (height: 16.5 cm; diameter: 2.8 cm) silica gel (0.04-0.06 mm) with a slight excess presof sure of nitrogen (40 kPa), eluting with mixtures of cyclohexane and ethyl acetate in proportions (by volume) of 80:20 (1.5 liters) and 50:50 (1 liter), collecting 50-cc fractions. Fractions 4 to 15 are combined and concentrated to dryness under reduced pressure (30 mm Hg; 4 kPa) at 40° C. to give 10-[(2RS)-1-diethylamino-2-propyl]-N-(2-methylpropyl)-2-phenothiazinecarbothioamide (1.3 g).

Proton NMR spectrum (400 MHz, DMSO, δ in ppm, J in Hz):

0.95 (D, J=7, 6H, —CH(CH$_3$)$_2$); 2.17 (Mt, 1H, —CH(CH$_3$)$_2$); 3.55 (Mt, 2H, —CN$\overline{S}$H—CH$_2$—); 7.05 to 7.35 (Mt, 5H, aromatic).

EXAMPLE 12

Fumaric acid (0.54 g) is added to a solution of 10-(1-diethylamino-2-propyl)-N-(2-methylpropyl)-2-phenothiazinecarbothioamide, L series (2 g) in methanol (20 cc) and is concentrated to dryness under reduced pressure (30 mm Hg; 4 kPa) at 40° C. The orange residue of meringue-like consistency is dissolved in acetic acid 40 cc), treated with mercuric acetate (1.6 g) and stirred for 5 hours at a temperature in the region of 20° C. The reaction mixture is then diluted with distilled water (50 cc) and filtered, and the yellow filtrate is concentrated to dryness under reduced pressure (30 mm Hg; 4 kPa) at 40° C. The residual yellow oil is taken up with ethyl acetate (50 cc) and the solution obtained is washed successively with N sodium hydroxide (50 cc), distilled water (25 cc) and saturated aqueous sodium chloride solution (25 cc), dried over magnesium sulphate in the presence of charcoal 3S, filtered and concentrated to dryness under reduced pressure (30 mm Hg; 4 kPa) at 40° C. The residual yellow oil (1.8 g) is purified by chromatography on a column (height: 25 cm; diameter: 4 cm) of silica gel (0.063-0.04 mm) under a slight excess pressure of nitrogen (300 mm Hg; 40 kPa), eluting successively with methylene chloride (1 liter), a mixture (98:2 by volume) (2 liters) of methylene chloride and methanol and a mixture (95:5 by volume) (1 liter) of methylene chloride and methanol, collecting 60-cc fractions. Fractions 14 to 60 are combined and concentrated to dryness under reduced pressure (30 mm Hg; 4 kPa) at 40° C. to give an orange oil (1.6 g). This product is dissolved in a mixture (91:9 by volume) (110 cc) of isopropyl ether and ethyl acetate, and a 0.64 N solution (6.2 cc) of hydrochloric acid in isopropyl ether is added dropwise, with stirring at a temperature in the region of 5° C. The precipitate formed is drained, washed with isopropyl ether (20 cc) and dried under reduced pressure (5 mm Hg; 0.7 kPa) at 40° C. 10-(1-Diethylamino-2-propyl)-N-(2-methylpropyl)-2-phenothiazinecarbothioamide hydrochloride, L series (1.3 g) is thereby obtained in the form of a white solid, m.p. 115-120° C. (melts forming a paste).

Proton NMR (250 MHz, DMSO, δ in ppm, J in Hz):
When dissolved in DMSO, two forms are observed, due to salification of the nitrogen.

0.9 (D, J=7, 6H, —CH(C$\underline{H}_3$)$_2$); 0.98 and 1.18 (2T, J=7, 6H, —N(CH$_2$C$\underline{H}_3$)$_2$); 1.85 (Mt, 4H, —CH$_3$ and —CH(C$\underline{H}_3$)$_2$); 3.10 (Mt, 2H, —CONH—C$\underline{H}_2$—); 3.17 (Cx, 4H, —N(C$\underline{H}_2$CH$_3$)$_2$); 3.4 and 3.73 (2Mt, 1H each, >N—C$\underline{H}_2$—); 4.77 (Mt, 1H, >N—C$\underline{H}$<); to 7.4 (Mt, 5H, aromatic); 7.54 (broad S, 1H, -H at 1-position); 7.57 (brood D, J=8, 1M, —h at 3-position); 8.6 (T, J=5.5, 1H, —CONH—); 9.95 (Cx, 1H, NH$^+$).

Infrared spectrum (KBr), characteristic bands in cm$^{-1}$:
3270, 3060, 2960, 2930, 2870, 2580, 2480, 1645, 1590, 1555, 1535, 1460, 1415, 1390, 1370, 1315, 1230, 870, 830, 755.

EXAMPLE 13

Mercuric acetate (1.4 g) is added with stirring to a solution of N-(2-methylpropyl)-10-[(2RS)-1-(1-pyrrolidinyl)-2-propyl]-2-phenothiazinecarbothioamide (1.5 g) in acetic acid (25 cc), and the suspension obtained is stirred for 1.5 hour at a temperature in the region of 20° C. The grey suspension is filtered and the filtrate concentrated to dryness under reduced pressure (30 mm Hg; 4 kPa) at 50° C. The cloudy residual oil is taken up with distilled water (20 cc) and ethyl ether (50 cc) and then alkalinized with sodium hydroxide (d =1.33) to pH 13. The organic phase is separated, washed with saturated aqueous sodium chloride solution (15 cc), dried over potassium carbonate, filtered and concentrated to dryness under reduced pressure (30 mm Hg; 4 kPa) at 50° C. The residual pasty product (1 g) of meringue-like consistency is purified by chromatography on a column (height: 30 cm; diameter: 2.6 cm) of silica gel (0.2×0.063 mm), eluting successively with a mixture (95:5 by volume) (100 cc) of ethyl acetat and methanol and with a mixture (85:15 by volume) (100 cc) of ethyl acetate and methanol and collecting 15-cc fractions. Fractions 9 to 11 are combined and concentrated to dryness under reduced pressure (30 mm Hg; 4 kPa) at 40° C. The residual yellow oil (0.55 g) is dissolved in isopropyl ether (20 cc) and treated dropwise and with stirring with a 3.3 N solution (0.5 cc) of hydrochloric acid in isopropyl ether. The precipitate formed is drained, washed with isopropyl ether (3×5 and dried under reduced pressure (5 mm Hg; 0.68 kPa) at 40° C. N-(2-Methyl.propyl)-10-[(2RS)-1-(1-pyrrolidinyl)-2-propyl]-2-phenothiazinecarboxamide ,hydrochloride (0.51 9) is thereby obtained in the form of a pale yellow powder, m.p. 155×160° C. (melts forming a paste).

Proton NMR (250 MHz, CDCl:, δ in ppm, J in Hz): 0.98 (D, J=7, 6H, —CH(C$\underline{H}_3$)$_2$); 1.87 (D, J=7, 3H, —CH$_3$); 1.98 (Mt, 1H, —C$\underline{H}$(CH$_3$)$_2$); 2.1 (Cx, 4H, pyrrolidine —C$\underline{H}_2$—C$\underline{H}_2$—); 2.80, 2.92, 3.78 and 4 (4Mt, 1H each, pyrrolidine —C/ $_2$—N—C$\underline{H}_2$—); 3.26 (Mt, 2H, —CONH—C$\underline{H}_2$—); 3.47 (broad D, J=13, 1H, 1H of NCH$_2$—); 3.7 (Mt, 1H, 1H of N—CH$_2$—); 5.25 (Mt, 1H, N—C$\underline{H}$); 6.95 to 7.25 (Mt, 5H, aromatic); 7.38 (D, J=8, 1H, —H at 3-position); 7.51 (S, 1H, —H at 1-position); 12.35 (Cx, 1H, —CONH—).

Infrared spectrum (KBr), characteristic bands in cm$^{-1}$:
3280, 3060, 2950, 2920, 2860, 2770, 2670, 2580, 1640, 1590, 1530, 1460, 1415, 1385, 1365, 1230, 870, 825, 755.

N-(2-Methylpropyl)-10-[(2RS)-1-(1-pyrrolidinyl)-2-propyl]-2-phenothiazinecarbothioamide may be prepared in the following manner:

A suspension of 10-[(2RS)-1-(-pyrrolidinyl)-2-propyl]-2-phenothiazinecarbothioamide (2 g) and 2-methylpropylamine (3 cc) in absolute ethanol (20 cc) is saturated for 15 minutes with hydrogen sulphide and then heated for 23 hours to a temperature in the region of 115° C. After being cooled, the mixture is concentrated to dryness under reduced pressure (30 mm Hg; 4 kPa) at 30° C. The residual paste is taken up with ethyl acetate (30 cc) and distilled water (20 cc). The organic phase is separated, washed with saturated aqueous sodium chloride solution (20 cc), dried over potassium carbonate, filtered and concentrated to dryness under reduced pressure (30 mm Hg; 4 kPa) at 50° C. The residual viscous yellow oil (2.5 g) is purified by chromatography on a column (height: 35 cm; diameter: 2.6 cm) of silica gel (0.2×0.063 mm), eluting with a mixture (92:8 by volume) (200 cc) of ethyl acetate and methanol and collecting 15-cc fractions. Fractions 5 to 11 are combined and concentrated to dryness under reduced pressure (30 mm Hg; 4 kPa) at 40° C. N-(2-Methylpropyl)-10-[(2RS)-1-(1-pyrrolidinyl)-2-propyl]-2-phenothiazinecarbothioamide (2.04 g) is thereby obtained in the form of a viscous yellow oil.

EXAMPLE 14

Mercuric acetate (0.94 g) is added to a solution of N-(2-methylpropyl)-10-[1-(1-pyrrolidinyl)-2-propyl]-2-phenothiazinecarbothioamide hydrochloride, L series (1.36 g) in ethyl acetate (27 cc), and the mixture is stirred for 16 hours at a temperature in the region o 20° C. The orange suspension obtained is filtered and the filtrate is concentrated to dryness under reduced pressure (30 mm Hg; 4 kPa) at 40° C. The residue is taken up with ethyl acetate (100 cc) and the solution obtained is washed with saturated aqueous sodium hydrogen carbonate solution (2×50 cc) and then with saturated aqueous sodium chloride solution (50 cc) and dried over magnesium sulphate in the presence of charcoal 3S. After filtration, the yellow filtrate is concentrated to dryness under reduced pressure (30 mm Hg; 4 kPa) at 40° C. and an orange oil (1.15 g) is thereby obtained, which is purified by chromatography on a column (height: 40 cm; diameter: 2 cm) of silica gel (0.063-0.04 mm) under a slight excess pressure of nitrogen (40 kPa), eluting successively with methylene chloride (500 cc), a mixture (98.7:1.3 by volume) (750 cc) of methylene chloride and methanol and then a mixture (97.5:2.5 by volume) (2 liters) of methylene chloride and methanol and collecting 50-cc fractions for the first liter of eluate and then 100-cc fractions. Fractions 11 to 23 are combined and concentrated to dryness under reduced pressure (30 mm Hg; 4 kPa) at 40° C. An orange oil (0.95 g) is thereby obtained. This product is dissolved in ethyl ether (50 cc) and a 0.23 N solution (10 cc) of hydrochloric acid in ethyl ether is added. The precipitate formed is drained, washed with ethyl ether (3×10 cc) and dried under reduced pressure (5 mm Hg; 0.7 kPa) at 40° C. N-(2-Methylpropyl)-10-[1-(1-pyrrolidinyl)-2-propyl]-2-phenothiazinecarboxamide hydrochloride, L series (0.75 g) is thereby obtained in the form of a white solid, m.p. 200-205° C. (melts forming a paste).

Proton NMR (250 MHz, DMSO, δ in ppm and J in Hz):

When dissolved in DMSO, two forms are observed, due to salification of the nitrogen.

0.9 (D, J=7.5, 6H, —CH(C$\underline{H}_3$)$_2$); 1.78 (D, J=7, 3H, —CH$_3$); 1.88 (Mt, 1H, —C$\underline{H}$(CH$_3$)$_2$); 1.75 to 2 (Mt, 4H, pyrrolidine —C$\underline{H}_2$—C$\underline{H}_2$—); 2.82, 3.09, 3.60 and 3.75 (4Mt, 1H each, pyrrolidine

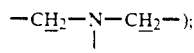

3.09 (Mt, 2H, —CONH—C$\underline{H}_2$—); 3.75 (limiting AB, 2H, >N—C$\underline{H}_2$—); 4.72 (Mt, 1H, >N—C$\underline{H}$<);7 to 7.35 (Mt, 5H, aromatic); 7.52 (broad S, 1H, -H at 1-position); 7.55 (broad D, J 8, 1H, —H at 3-position); 8.60 (T, J=5.5, 1H, —CONH—); 10.48 (Cx, 1H, —N$\underline{H}^+$).

Infrared spectrum (KBr), characteristic bands in cm$^{-1}$:

3280, 3060, 2960, 2925, 2875, 2680, 2590, 2475, 1640, 1595, 1540, 1460, 1415, 1385, 1370, 1315, 1230, 875, 830, 755.

N-(2-Methylpropyl)-2-phenothiazinecarbothioamide hydrochloride. L series may be obtained in the following manner:

A mixture of 10-[1-(1-pyrrolidinyl)-2-propyl]-2-phenothiazinecarbothioamide, L series (2 g) and 2-methylpropylamine (2.75 cc) in ethanol (40 cc) is saturated with hydrogen sulphide and then heated for 16 hours to 100° C. After being cooled, the solution is concentrated to dryness under reduced pressure (30 mm Hg; 4 kPa) at 40° C. and an orange oil (2.7 g) is obtained, which is purified by chromatography on a column (height: 40 cm; diameter: 4 cm) of silica gel (0.063-0.04 mm) under a slight excess pressure of nitrogen (300 mm Hg; 40 kPa), eluting successively with methylene chloride (500 cc) and then a mixture (97.5:2.5 by volume) (500 cc) of methylene chloride and methanol and collecting 60-cc fractions. Fractions 12 to 16 are combined and concentrated to dryness under reduced pressure (30 mm Hg; 4 kPa) at 40° C. and an orange oil (1.72 g) is obtained. This product is dissolved in ethyl ether (50 cc) and the solution is treated with charcoal 3S and filtered; a 3 N solution (1.5 cc) of hydrochloric acid in ethyl ether is added to this filtrate. The precipitate formed is drained, washed with ethyl ether (3×10 cc) and dried under reduced pressure (5 mm Hg; 0.7 kPa) at 40° C. N-(2-Methylpropyl)-10-[1-(1-pyrrolidinyl)-2-propyl]-2-phenothiazinecarbothioamide hydrochloride, L series (1.4 g) is thereby obtained in the form of a yellow solid, m.p. about 120° C. (melts forming a paste).

$[\alpha]^{20}_D = +24 \pm 0.5°$ (1%; dimethylformamide).

EXAMPLE 15

Mercuric acetate (0.65 g) is added to a solution of N-(2-methylpropyl)-10-[1-(1-pyrrolidinyl)-2-propyl]-2-phenothiazinecarbothioamide hydrochloride, D series (0.95 g) in acetic acid (19 cc), and the mixture is stirred for 24 hours at a temperature in the region of 20° C. The orange suspension obtained is filtered and the filtrate is concentrated to dryness under reduced pressure (30 mm Hg; 4 kPa) at 40° C. The residue is taken up with ethyl acetate (100 cc) and the solution obtained is washed with saturated aqueous sodium hydrogen carbonate solution (2×50 cc) and then with saturated aqueous sodium chloride solution (50 cc) and dried over magnesium sulphate in the presence of charcoal 3S. After filtration, the yellow filtrate is concentrated to dryness under reduced pressure (30 mm Hg; 4 kPa) at 40° C. and an orange oil (0.76 g) is thereby obtained. This product is purified by chromatography on a column (height: 40 cm; diameter: 2 cm) of silica gel (0.063-0.04 mm) under a slight excess pressure of nitrogen (40 kPa), eluting successively with methylene chloride (500 cc), a mixture (98.7:1.3 by volume) (750 cc) of methylene chloride and methanol and then a mixture (97.5:2.5 by volume) (1 liter) of methylene chloride and methanol and collecting 50-cc fractions from the first liter of eluate and then 80-cc fractions Fractions 15 to 28 are combined and concentrated to dryness under reduced pressure (30 mm Hg; kPa) at 40 C. An orange oil (0.47 g) is thereby obtained. This product is dissolved in ethyl ether (30 cc) and a 0.23 N solution (5 cc) of hydrochloric acid in ethyl ether is added. The precipitate formed is drained, washed with ethyl ether (3×5 cc) and dried under reduced pressure (5 mm Hg; 0.7 kPa) at 40° C. N-(2-Methylpropyl)-10-1(1-pyrrolidinyl)-2-propyl]-2-phenothiazinecarboxamide hydrochloride, D series (0.4 g) is thereby obtained in the form of a white solid, m.p. 190-200° C. (melts forming a paste), the NMR spnctrum of which is identical to that of the product described in Example 14.

$[\alpha]^{20}_D = -16.7 \pm 0.5°$ (1% dimethylformamide).

Infrared spectrum (KBr), characteristic bands in cm$^{-1}$.

3280, 3060, 2960, 2925, 2875, 2685, 2610, 2480, 1640, 1595, 1540, 1460, 1415, 1385, 1370, 1320, 1230, 875, 830, 755.

N-(2-Methylpropyl)-10-[1-(1-pyrrolidinyl)-2-propyl]-2-phenothiazinecarbothioamide hydrochl-oride, D series may be prepared in the following manner:

A mixture of 10-[1-(1-pyrrolidinyl)-2-propyl]-2-phenothiazinecarbothioamide, D series 2 g) and 2-methylpropylamine (2.75 cc) in ethanol (40 cc) is saturated with hydrogen sulphide and then heated for 16 hours to 100° C. After being cooled, the solution is concentrated to dryness under reduced pressure (30 mm Hg; 4 kPa) at 40° C. and an orange oil (2.3 g) is obtained. This product is purified by chromatography on a column (height: 40 cm;

diameter: 4 cm) of silica gel (0.063-0.04 mm) under a slight excess pressure of nitrogen (40 kPa), eluting successively with methylene chloride (500 cc) and then a mixture (97.5:2.5 by volume) (500 cc) of methylene chloride and methanol and collecting 60-cc fractions. Fractions 12 to 16 are combined and concentrated to dryness under reduced pressure (30 mm Hg; 4 kPa) at 40° C. and an orang oil (1.25 g) is obtained. This product is dissolved in ethyl ether (50 cc) and the solution is treated with charcoal 3S and filtered; a 3 N solution (1 cc) of hydrochloric acid in ethyl ether is added to this filtrate. The precipitate formed is drained, washed with ethyl ether (3×10 cc) and dried under reduced pressure (5 mm Hg; 0.7 kPa) at 40° C. N-(2-Methylpropyl)-10-[1-(1-pyrrolidinyl)-2-propyl]-2-phenothiazinecarbothioamide hydrochloride. D series (1 g) is thereby obtained in the form of a yellow solid melting at about 120° C. (melts forming a paste).

EXAMPLE 16

A suspension of N-pentyl-10-[(2RS)-1-(1-pyrrolidinyl)-2-propyl]-2-phenothiazinecarbothioamide (1.7 g) and mercuric acetate (1.4 g) in acetic acid (25 cc) is stirred for 16 hours at a temperature in the region of 20° C. The black suspension obtained is diluted with ethyl ether (15 cc) and filtered and the filtrate is concentrated to dryness under reduced pressure (30 mm Hg; 4 kPa) at 40° C. The brown residue is taken up with distilled water (20 cc), alkalinized to pH 13 with sodium hydroxide (d=1.33) and extracted with ethyl acetate (25 cc). The organic phase is washed with distilled water (10 cc), dried over potassium carbonate, filtered and concentrated to dryness under reduced pressure (30 mm Hg; 4 kPa) at 50° C. The residual viscous light brown oil (1.5 g) is purified by chromatography on a column (height: 45 cm; diameter: 3.2 cm) of silica gel (0.04–0.063 mm) under a slight excess pressure of nitrogen (40 kPa), eluting with a mixture (90:10 by volume) (800 cc) of ethyl acetate and methanol and collecting 25-cc fractions. Fractions 13 to 23 are combined and concentrated to dryness under reduced pressure (30 mm Hg; 4 kPa) at 40° C. The residual viscous oil is dissolved in ethyl ether (25 cc) and a 3.3 N solution (1 cc) of hydrochloric acid in isopropyl ether is added dropwise and with stirring. The precipitate formed is drained, washed with isopropyl ether (2×5 cc) and dried under reduced pressure (5 mm Hg; 0.7 kPa) at 40° C. N-Pentyl-10-[(2RS)-1-(1-pyrrolidinyl)-2-propyl]-2-phenothiazinecarboxamide hydrochloride (0.9 g) is thereby obtained in the form of a white powder, m.p. 214° C.

Proton NMR (250 MHz, DMSO, δ in ppm, J in Hz): 0.9 (T, J 7, 3H, —CH$_2$—CH$_3$); 1.32 (Mt, 4H, —CH$_2$—CH$_2$—CH$_3$); 1.55 (Mt, 2H, —CH—(CH$_2$)$_2$—CH$_3$); 1.8 (D, J=7, 3H, —CH$_3$); 1.75 to 2 (Mt, 4H, pyrrolidine —CH$_2$—); 2.85, 3.10, 3.6 and 3.75 (4Mt, 1H each, pyrrolidine >N—CH$_2$—); 3.26 (Mt, 2H, —CONH—CH$_2$); 3.77 (Mt, 2H, >N—CH$_2$—); 4.77 (Mt, 1H, >N—CH<); 7 to 7.4 (Mt, 5H, aromatic); 7.53 (S, 1H, —H at 1-position); 7.55 (D, J=8, 1H, —H at 3-position); 8.66 (T, J=5.5, 1H, —CONH—); 10.80 (Cx, 1H, —NH$^+$).

Infrared spectrum (KBr), characteristic bands in cm$^{-1}$:
3270, 3060, 2950, 2920, 2860, 2850, 2670, 2610, 2580, 1645, 1590, 1535, 1460, 1410, 1375, 1305, 1230, 860, 830, 750.

N-Pentyl-10-[(2RS)-1-(1-pyrrolidinyl)-2-propyl]-2-phenothiazinecarbothioamide may be prepared in the following manner:

A suspension of 10-[(2RS)-1-(1-pyrrolidinyl)-2-propyl]-2-phenothiazinecarbothioamide (2 g and pentylamine (3 cc) in absolute ethanol (30 cc) is saturated with hydrogen sulphide and then heated for 2 hours to a temperature in the region of 100° C. After being cooled, the mixture is concentrated to dryness under reduced pressure (30 mm Hg; 4 kPa) at 40° C. The pasty residue is taken up with ethyl ether (50 cc) and distilled water (15 cc). The organic phase is separated, dried over potassium carbonate and concentrated to dryness under reduced pressure (30 mm Hg; 4 kPa) at 40° C. The residual viscous yellow oil is purified by chromatography on a column (height: 35 cm; diameter: 2.6 cm) of silica gel (0.2–0.063 mm), eluting with ethyl acetate (300 cc) and collecting 25-cc fractions Fractions 3 to 9 are combined and concentrated to dryness under reduced pressure (30 mm Hg; 4 kPa) at 40° C. N-Pentyl-10-[(2RS)-1-(1-pyrrolidinyl)-2-propyl]-2-phenothiazinecarbothioamide (2.25 g) is thereby obtained in the form of a yellow oil.

Proton NMR (250 MHz, DMSO, δ in ppm, J in Hz): 0.92 (T, J=7, 3H, pentyl —CH$_3$); 1.35 (Mt, 4H, —CH$_2$—CH$_2$—CH$_3$); 1.7 (Mt, 2H, —CH$_2$—(CH$_2$)$_2$CH$_3$); 3.55 to 3.90 (Mt, 4H, N—CH$_2$— and —CSNH—CH$_2$—); 7 to 7.35 (Mt, 5H, aromatic); 7.43 (DD, J=8 and 1, 1H, —H at 3-position); 7.57 (D, J=1, 1H, —H at 1-position).

EXAMPLE 17

N-[(2RS)-2-methylbutyl]-10-[(2RS)-1-(N-ethyl-N-methylamino)-2-propyl]-2-phenothiazinecarbothioamide (1 g) is dissolved in a solution of fumaric acid (0.27 g) in absolute ethanol (20 cc), and the mixture is concentrated to dryness under reduced pressure (30 mm Hg; 4 kPa) at 40° C. The residue is dissolved in acetic acid (16.7 cc) and mercuric acetate (0.78 g) is added. The suspension obtained is stirred for 16 hours at a temperature in the region of 20° C. to give a black suspension which is diluted with distilled water (25 cc) and filtered. The orange filtrate is alkalinized with caustic soda solution (d=1.33) to pH 13 and extracted with ethyl acetate (2×50 cc). The combined organic phases are washed successively with distilled water (2×25 cc) and with saturated aqueous sodium chloride solution 25 cc), dried over magnesium sulphate in the presence of charcoal 3S, filtered and concentrated to dryness under reduced pressure (30 mm Hg; 4 kPa) at 40° C. The residual yellow oil (1 g) is purified by chromatography on a column (height: 25 cm; diameter: 2 cm) of silica gel (0.04–0.063 mm) under a slight excess pressure of nitrogen (40 kPa), eluting successively with ethyl acetate (500 cc) and with a mixture (90:10 by volume) (1.2 liter) of ethyl acetate and methanol, collecting 50-cc fractions. Fractions 21 to 30 are combined and concentrated to dryness under reduced pressure (30 mm Hg; 4 kPa) at 40° C. A yellow oil (0.46 g) is obtained, which crystallizes. This product is dissolved in isopropyl ether (10 cc) under reflux and then left to stand for 1 hour at a temperature in the region of 5° C. The crystals formed are drained, washed with isopropyl ether (2 x 2 cc) and dried under reduced pressure (5 mm Hg; 0.7 kPa) at 40° C. N-[(2RS)-2-Methylbutyl]-10-[(2RS)-1-(N-ethyl-N-methylamino)-2-propyl]-2-phenothiazinecarboxamide (0.23 g) is thereby obtained in the form of off-white crystals, m.p. 95° C.

Proton NMR (250 MHz, DMSO, δ in ppm and J in Hz):
0.9 (Mt, 9H, 2—CH$_3$ of 2-methylbutyl, >NCH$_2$CH$_3$); 1.14 and 1.44 ((2Mt, 1H each, —CH$_2$—CH$_3$); 1.62 (D, J=7, 3H, —CH$_3$); 1.65 (Mt, 1H, 2-methylbutyl —CH—); 2.23 (S, 3H, —N—CH$_3$); 2.41 (Mt, 2H, >N—CH$_2$—CH$_3$); 2.67 (DD, J=14 and 6.5, 1H, 1H of >N—CH$_2$—); 2.97 (DD, J=14 and 6, 1H, 1H of >NCH$_2$—); 3 to 3.3 (Mt, 2H, —CONH—CH$_2$—); 4.17 (Mt, J=7, 6.5 and 6, 1H, >N—CH<); 6.90 to 7.3 (Mt, 5H, aromatic); 7.42 (DD, J=8 and 1, 1H, —H at 3-position); 7.55 (D, J = 1, 1H, —H at 1-position); 8.4 (T, J=5.5, 1H, —CONH—).

Infrared spectrum (KBr), characteristic bands in cm$^{-1}$:
3320, 3060, 2965, 2930, 2875, 2845, 2790, 1630, 1590, 1580, 1540, 1460, 1415, 1380, 1320, 1240, 825, 750.

N-[(2RS)-2-Methylbutyl]-10-[(2RS)-1-(N-ethyl-N-methylamino)-2-propyl]-2-phenothiazinecarbothioamide may be prepared in the following manner:

A solution of 10-[(2RS)-1-(N-ethyl-N-methyl-amino)-2-propyl]-2-phenothiazinecarbothioamide (1 g) and (2RS)-2-methylbutylamine (4.9 cc) in absolute ethanol (15 cc) is saturated with hydrogen sulphide and heated for 16 hours to a temperature in the region of 100° C. After being cooled, the mixture is concentrated to dryness under reduced pressure (30 mm Hg; 4 kPa) at 40° C. The oily orange residue is purified by chromatography on a column (height: 25 cm; diameter: 2 cm) of silica gel (0.04–0.063 mm) under a slight excess pressure of nitrogen (40 kPa), eluting with a mixture (80:20 by volume) (500 cc) of ethyl acetate and cyclohexane and collecting 40-cc fractions Fractions 4 to 8 are combined and concentrated to dryness under reduced pressure (30 mm Hg; 4 kPa) at 40° C. N-[(2RS)-2-Methylbutyl]--10-[(2RS)-1-(N-ethyl-N-methylamino)-2-propyl]-2-phenothiazinecarbothioamide (1.88 g) is obtained in the form of a yellow oil.

EXAMPLE 18

Mercuric acetate (1.3 g) is added to a solution of N-[(2RS)-2-methylbutyl]10-[(2RS)-1-(1-pyrrolidinyl)-2-propyl]-2-phenothiazinecarbothioamide (1.4 g) in acetic acid (25 cc), and the suspension obtained is stirred for 2 hours at a temperature in the region of 20° C. The black precipitate formed is drained and washed with acetic acid (2×5 cc) and the filtrate is concentrated to dryness under reduced pressure (30 mm Hg; 4 kPa) at 60° C. The brown residue is taken up with distilled water (15 cc) and ethyl acetate (25 cc) and alkalinized with N aqueous sodium hydroxide solution. The organic phase is separated, filtered on supercel, dried over potassium carbonate, filtered again and concentrated to dryness under reduced pressure (30 mm Hg; 4 kPa) at 20° C. The pale yellow viscous resin (1.3 g) obtained is dissolved in isopropyl ether (50 cc) and treated with a 3.3 N solution (1 cc) of hydrochloric acid in isopropy-1 ether. The precipitate is drained, washed with isopropyl ether (3×10 cc) and dried under reduced pressure (5 mm Hg; 0.7 kPa) at 40° C. N-[(2RS)-2-Methylbutyl]-10-[(2RS)-1-(1-pyrrolidinyl)-2-propyl]-2-phenothiazinecarboxamide hydrochloride (1.2 g) is thereby obtained in the form of an off-white powder, m.p. 155–160° C. (melts forming a paste).

Proton NMR (205 MHz, DMSO, δ in ppm, J in Hz): 0 89 and 0.90 (D and T, J=7, 6H, CH—CH$_3$ and —CH$_2$CH$_3$ respectively); 1.13 and 1.43 (2Mt, 1$\overline{H}$ each, —CH$_2$C$\overline{H}_3$); 1.7 (Mt, 1H, 2-methylbutyl >CH—); 1.79 (D, $\overline{J}$=7, 3H, —CH$_3$); 1.75 to 2 (Mt, 4H, pyrrolidine —CH$_2$—CH$_2$—); 2.85, 10, 3.60 and 3.75 (4Cx, 1H each, 2 >N—C$\overline{H}_2$ of pyrrolidine); 3 to 3.3 (Mt, 2H, —CONH—CH$_2$—), 3.65 to 3.90 (Mt, 2H, >N—CH$_2$—); 4.8 (Mt, 1$\overline{H}$, >N—CH<); 7 to 7.4 (Mt, 5H, aromatic); 7.55 (S, 1H, —H at 1-position); 7.57 (D, J=8, 1H, -H at 3-position); 8.65 (T, J=5.5, 1H, —CONH—); 10.85 (Cx, 1H, —NH+).

Infrared spectrum (KBr), characteristic bands in cm$^{-1}$.

3290, 3060, 2980, 2925, 2875, 2670, 2585, 2475, 1645, 1595, 1535, 1460, 1410, 1380, 1305, 1230, 830, 755.

N-[(2RS)-2-Methylbutyl]-10-[(2RS)-1-(1-pyrrolidinyl)-2-propyl]-2-phenothiazinecarbothioamide may be prepared in the following manner:

A stirred suspension of 10-[(2RS)-1-(1-pyrrolidinyl)-2-propyl]-2-phenothiazinecarbothioamide (2 g) and 2-methylbutylamine (3 cc) in anhydrous ethanol (15 cc) is saturated with hydrogen sulphide and the mixture is heated for 1 hour to a temperature in the region of 115° C. After being cooled, the mixture is concentrated to dryness under reduced pressure (30 mm Hg; 4 kPa) at 50° C. The residual yellow paste is taken up with ethyl acetate (30 cc) and distilled water (20 cc). The organic phase is separated, washed with saturated aqueous sodium chloride solution (20 cc), dried over magnesium sulphate, filtered and concentrated to dryness under reduced pressure (30 mm Hg; 4 kPa) at 40° C. The residual viscous yellow oil (2.2 g) is purified by chromatography on a column (height: 40 cm; diameter: 3.2 cm) of silica gel (0.04–0.063 mm), eluting with a mixture (92:8 by volume) (300 cc) of ethyl acetate and methanol and collecting 25-cc fractions. Fractions 6 to 11 are combined and concentrated to dryness under reduced pressure (30 mm Hg; 4 kPa) at 40° C. N-[(2RS)-2-Methylbutyl]-10-[(2RS)-1-(1-pyrrolidinyl)-2-propyl]-2-phenothiazinecarbothioamide (1.8 g) is thereby obtained in the form of a viscous yellow oil.

EXAMPLE 19

Mercuric acetate (2.2 g) is added to a solution of N-[(2S)-2-methylbutyl]-10-[1-(1-pyrrolidinyl)-2-propyl]-2-phenothiazinecarbothioamide hydrochloride, L series (2.5 g) in acetic acid (50 cc), and the mixture is stirred for 16 hours at a temperature in the region of 20° C. The orange suspension obtained is diluted with distilled water (100 cc) and filtered and the filtrate is concentrated to dryness under reduced pressure (30 mm Hg; 4 kPa) at 40° C. The residue is taken up with ethyl acetate (200 cc) and distilled water (100 cc). Sodium hydroxide (d=1.33) is added to pH 13. The organic phase is separated after settling has taken place, washed successively with distilled water (2×50 cc) and with saturated aqueous sodium chloride solution (50 cc) and dried over magnesium sulphate. After filtration, the yellow filtrate is concentrated to dryness under reduced pressure (30 mm Hg; 4 kPa) at 40° C.; an orange oil (1.9 g) is thereby obtained. This product is dissolved in ethyl acetate (10 cc) and a 3.3 N solution (1.4 cc) of hydrochloric acid in isopropyl ether is added dropwise and with stirring. The crystals formed are separated by filtration, washed with isopropyl ether (3×10 cc) and dried under reduced pressure (5 mm Hg; 0.7 kPa). N-[(2S)-2-Methylbutyl]-10-[1-(1-pyrrolidinyl)-2-propyl]-2-pheno thiazinecarboxamide hydrochloride, L series (1.05 g) is thereby obtained in the form of a beige solid, m.p. 190° C., the NMR spectrum of which is identical to that of the product described in Example 18.

Infrared spectrum (KBr), characteristic bands in cm$^{-1}$:

3280, 3060, 2960, 2930, 2875, 2680, 2590, 2480, 1640, 1595, 1540, 1460, 1415, 1380, 1310, 1235, 860, 830, 755.

N-[(2S)-2-Methylbutyl]-10-[1-(1-pyrrolidinyl)-2-propyl]-2-phenothiazinecarbothioamide hydrochloride, L series may be obtained in the following manner:

A mixture of 10-[1-(1-pyrrolidinyl)-2-propyl]-2-phenothiazinecarbothioamide, L series (4 g) and (2S)-2-methylbutylamine (5 g) in ethanol (60 cc) is saturated with hydrogen sulphide and then heated for 16 hours to 100° C. After being cooled, the solution is concentrated to dryness under reduced pressure (30 mm Hg; 4 kPa) at 40° C. An orange oil (5.3 g) is obtained, which is purified by chromatography on a column (height: 48 cm; diameter: 4 cm) of silica gel (0.063–0.2 mm), eluting with a mixture (97.5:2.5 by volume) (2 liters) of methylene chloride and methanol and collecting 60-cc fractions. Fractions 23 to 29 ar combined and concentrated to dryness under reduced pressure (30 m Hg; 4 kPa) at 40° C. An orange oil (4.1 g) is obtained. This product is dissolved in a mixture (75:25 by volume) (200 cc) of isopropyl ether and ethyl acetate, and a 0.72 N solution (12.8 cc) of hydrochloric acid in isopropyl ether is added with stirring and at a temperature in the region of 5° C. The precipitate formed is drained, washed with isopropyl ether (3×20 cc) and dried under reduced pressure (5 mm Hg; 0.7 kPa) at 40° C. N-[(2S)-2-Methylbutyl]-2-phenothiazinecarbothioamide hydrochloride, L series (3.2 g) is thereby obtained in the form of a yellow solid, m.p. 135–140° C. (melts forming a paste), the NMR spectrum of which is identical to that of the thioamide described in Example 18.

$[\alpha]^{20}_D = +28.3 \pm 0.6°$ (1%; dimethylformamide).

EXAMPLE 20

Mercuric acetate (0.7 g) is added to a solution of N-[(2RS)-2-methylbutyl]-10-[1-(1-pyrrolidinyl)-2-propyl]-2-phenothiazinecarbothioamide, L series (0.8 g) in acetic acid (16 cc), and the mixture is stirred for 16 hours at a temperature in the region of 20° C. The orange suspension obtained is diluted with distilled water (50 cc) and filtered and the orange filtrate is concentrated to dryness under reduced pressure (30 mm Hg; 4 kPa) at 40° C. The residue is taken up with ethyl acetate (100 cc) and distilled water (25 cc). Caustic soda solution (d=1.33) is added to pH 13. The organic phase is separated after settling has taken place, washed successively with distilled water (2×25 cc) and with saturated aqueous sodium chloride solution (25 cc) and dried over magnesium sulphate After filtration, the yellow filtrate is concentrated to dryness under reduced pressure (30 mm Hg; 4 kPa) at 40.C and a yellow gum (0.5 g) is thereby obtained. This product is dissolved in isopropyl- ether (25 cc) and a 0.24 N solution (5.4 cc) of hydrochloric acid in isopropyl ether is then added dropwise, with stirring and at a temperature in the region of 5° C. The precipitate formed is separated by filtration, washed with isopropyl- ether (3×10 cc) and dried under reduced pressure (5 mm Hg; 0.68 kPa). N-[(2RS)-2-Methylbutyl-]-10-[1-(1-pyrrolidinyl)-2-propyl]-2-phenothiazinecarbokamide hydrochloride, L series (0.4 g) is thereby obtained in the form of a white solid, m.p. 178° C., the NMR spectrum of which is identical to that of the product described in Example 18.

$[\alpha]^{\circ}_D = +15.5 \pm 0.5°$ (1%; dimethylformamide).

Infrared spectrum (KBr), characteristic bands in cm$^{-1}$:

3310, 3060, 2960, 2925, 2870, 2680, 2600, 2475, 1635, 1590, 1540, 1470, 1410, 1380, 1310, 1230, 870, 830, 755.

N-[(2RS)-2-Methylbutyl]-10-[1-(1-pyrrolidinyl)-2-propyl]-2-phenothiazinecarbothioamide hydrochloride, L series may be obtained in the following manner:

A mixture of 10-[1-(1-pyrrolidinyl)-2-propyl]-2-phenothiazinecarbothioamide, L series (2 g) and (2RS)-2-methylbutylamine (9.5 cc) in ethanol (30 cc) is saturated with hydrogen sulphide and then heated for 16 hours to 100° C. After being cooled, the solution is concentrated to dryness under reduced pressure (30 mm Hg; 4 kPa) at 40° C. An orange oil (3.8 g) is obtained, which is purified by chromatography on a column (height: 40 cm; diameter: 3 cm) of silica gel (0.063-0.2 mm), eluting with a mixture (97.5:2.5 by volume) (1.5 liters) of methylene chloride and methanol and collecting 30-cc fractions. Fractions 35 to 46 are combined and concentrated to dryness under reduced pressure (30 mm Hg; 4 kPa) at 40° C. An orange oil (1.8 g) is obtained. This product is dissolved in a mixture (80:20 by volume) (60 cc) of isopropyl ether and ethyl acetate and a 0.37 N solution (11 cc) of hydrochloric acid in isopropyl ether is then added with stirring and at a temperature inthe region of 5° C. The precipitate formed is drained, washed with isopropyl ether (3×10 cc) and dried under reduced pressure (5 mm Hg; 0.7 kPa) at 40° C. N-[(2RS)-2-Methylbutyl]-10-[1-(1-pyrrolidinyl)-2-propyl]-2-phenothiazinecarbothiomamide hydrochloride, L series (1.4 g) is thereby obtained in the form of a yellow solid, m.p. 120–125° C. (melts forming a paste), the NMR spectrum of which is identical to that of the thioamide described in Example 18.

$[\alpha]^{20}_D = +24.3 \pm 0.8°$ (0.7%; dimethylformamide).

EXAMPLE 21

A solution of 10-(1-diethylamino-2-propyl)-N(3-methyl-1-butyl)-2-phenothiazinecarbothioamide, L series (2 g) and fumaric acid (0.52 g) in ethanol (20 cc) is concentrated to dryness under reduced pressure (30 mm Hg; 4 kPa) at 40° C. The residue is taken up with stirring with acetic acid (35 cc), mercuric acid (1.5 g) is then added and stirring is continued at a temperature in the region of 20° C. for 16 hours. The grey suspension obtained is diluted with distilled water (60 cc) and filtered. The orange filtrae is treated with caustic soda (d=1.33) to pH 13 and extracted with ethyl acetate (200 cc). The organic phase is washed successively with distilled water (2×50 cc) and with saturated aqueous sodium chloride solution (50 cc) and dried over magnesium sulphate in the presence of charcoal 3S. After filtration, the yellow filtrate is concentrated to dryness under reduced pressure (30 mm Hg; 4 kPa) at 40° C. and an orange oil (1.55 g) is thereby obtained. This product is purified by chromatography on a column (height: 25 cm; diameter: 2.6 cm) of silica gel (0.04-0.063 mm) under a slight excess pressure of nitrogen (40 kPa), eluting with ethyl acetate (750 cc) and then with a mixture (90:10 by volume) (1,500 cc) of ethyl acetate and methanol and collecting 50-cc fractions. Fractions 12 to 44 are combined and concentrated to dryness under reduced pressure (30 mm Hg; 4 kPa) at 40° C. A yellow oil $[\alpha]^{20}_D = +15.6°$; 0.64%; chloroform) (1.1 g) is obtained. This product is dissolved in isopropyl ether (100 cc), a 0.45 N solution (5.8 cc) of hydrochloric acid in isopropyl ether is then added with stirring at a temperature in the region of 5° C., and stirring is continued for 30 minutes. The precipitate formed is drained, washed with isopropyl ether (2 cc) and dried at 40° C. under reduced pressure (5 mm Hg; 0.7 kPa). 10-(1-Diethylamino-2-propyl)-N-(3-methyl-1-butyl)-2-phenothiazinecarboxamide hydrochloride, L series (0.88 g) is thereby obtained in the form of a white solid, m.p. 100–105° C. (melts forming a paste).

$[\alpha]^{20}_D +15.7°$ (0.9%; dimethylformamide).

Proton NMR (250 MHz, DMSO, δ in ppm, J in Hz): 0.93 (D, J=7, 6H, —CH(CH$_3$)$_2$); 0.98 and 1.17 (2T, J=7, 3H each, —N(CH$_2$CH$_3$)$_2$); 1.44 (Q, J=7, 2H >N—CH$_2$CH$_2$—); 1.62 (Mt, 1H, 3-methylbutyl >CH—); 1.85 (D, J=7, 3H, —CH$_3$); 3.17 (Mt, 4H, —N(CH$_2$CH$_3$)$_2$); 3.3 (Mt, 2H, —CONH—CH$_2$—); 3.4 (Mt, 1H, 1H of >N—CH$_2$—); 3.76 (DD, J=14 and 7.5, 1H, 1H of N—CH$_2$—); 4.81 (Mt, 1H, >N—CH<); 7 to 7.4 (Mt, 5H, aromatic); 7.52 (S, 1H, —H at 1-position); 7.53 (D, J=7.5, 1H, —H at 3-position); 8.6 (T, J=5.5, 1H, —CONH—); 10.13 (Cx, 1H, —NH+).

Infrared spectrum (KBr), characteristic bands in cm$^{-1}$:

3270, 3060, 2955, 2940, 2870, 2640, 2580, 2480, 1640, 1590, 1535, 1460, 1415, 1395, 1385, 1365, 1310, 1230, 875, 830, 755.

10-(1-Diethylamino-2-propyl)-N-(3-methyl-1-butyl)-2-phenothiazinecarbothioamide, L series may be prepared in the following manner:

3-Methylbutylamine (10.7 cc) is added to a solution of 10-(1-diethylamino-2-propyl)-2-phenothiazinecarbothioamide acid fumarate, L series (3 g) in absolute ethanol (45 cc), and this solution is saturated with hydrogen sulphide. The mixture is then brought to a temperature in the region of 105° C. for 16 hours and concentrated to dryness under reduced pressure (30 mm Hg; 4 kPa). The residual orange oil is purified by chromatography on a column (height: 35 cm; diameter: 3 cm) of silica gel (0.2-0.063 mm), eluting with a mixture (70:30 by volume) (400 cc) of ethyl acetate and cyclohexane, collecting 30-cc fractions. Fractions 7 to 10 are combined and concentrated to dryness under reduced pressure (30 mm Hg; 4 kPa) at 50° C. to give 10-(1-diethylamino-2-propyl)-N-(3-methyl-1-butyl)-2-phenothiazinecarbothioamide, L series (3.1 g) in the form of an orange oil, the NMR characteristics of which are identical to those described below in Example 22.

10-(1-Diethylamino-2-propyl)-2-phenothiazinecarbothioamide acid fumarate, L series may be prepared in the following manner:

A solution of 10-(1-diethylamino-2-propyl)-2-phenothiazinecarbonitrile, L series (5.2 g) and triethylamine (2.2 cc) in anhydrous pyridine (104 cc) is saturated with hydrogen sulphide at 20° C. for 1 hour with stirring, and then stirred at 20° C. for 17 hours. The reaction mixture is purged with nitrogen for 1 hour, poured into distilled water (500 cc) and extracted with ethyl acetate (2×250 cc). The combined organic phases are washed successively with distilled water (3×100 cc) and with saturated aqueous sodium chloride solution (100 cc), dried over magnesium sulphate and filtered. The yellow filtrate is concentrated to dryness under reduced pressure (30 mm Hg; 4 kPa) at 40° C. to give 6.5 g of an orange oil. This product is purified by chromatography on a column (height: 44 cm; diameter: 3.4 cm) of silica gel (0.2-0.063 mm), eluting with a mixture (30:70 by volume)

0.93 (D, J=7, 6H, —CH(CH$_3$):); 0.98 and 1.17 (2T, 150-cc fractions. Fractions 8 to 17 are combined and concentrated to dryness under reduced pressure (30 mm Hg; 4 kPa) at 40° C. An orange oil $[\alpha]^{20}_D = -33.7° \pm 0.6°$; 1.006%; chloroform) (5.08 g) is obtained. This product is dissolved at a temperature in the region of 60° C. in ethanol (20 cc), and this solution is poured into a solution of fumaric acid (1.56 g) in ethanol (20 cc) at a temperature in the region of 60° C. and then left to stand for 16 hours at a temperature in the region of 5° C. The crystals formed are drained, washed with ethanol (2 ×2 cc) and dried at 40° under reduced pressure (5 mm Hg; 0.7 kPa). 10-(1-Diethylamino-2-propyl)-2-phenothiazinecarbothioamide acid fumarate, L series (5.5 g) is thereby obtained in the form of yellow crystals, m.p. 186° C.

$[\alpha]^{20}_D = +29.1° \pm 0.6°$ (1%; dimethylformamide).

10-(1-Diethylamino-2-propyl)-2-phenothiazinecarbonitrile, L series may be prepared in the following manner:

Sodium carbonate (3.2 g) and iodoethane (2.3 cc) phenothiazinecarbonitrile, L series (7 g) in dimethylformamide (86 cc), and this mixture is then brought to a temperature in the region of 150° C. for 6 hours. After being cooled, the reaction mixture is concentrated to dryness under reduced pressure (30 mm Hg; 4 kPa) at 40° C. and the residue is taken up with ethyl acetate (250 cc). The solution obtained is washed successively with distilled water (2×100 cc) and with saturated aqueous sodium chloride solution (100 cc), dried over magnesium sulphate in the presence of charcoal 3S and filtered. The yellow filtrate is concentrated to dryness under reduced pressure (30 mm Hg; 4 kPa) at 40° C. to give an orange oil (6.65 g) which crystallizes slowly. This residue is dissolved in the minimum amount of isopropyl ether under reflux, the small amount of insoluble matter is filtered off hot, and the filtrate is stored for 3 days at a temperature in the region of 5° C. The crystals formed are drained, washed with isopropyl ether (2×2 cc) and dried at 40° C. under reduced pressure (5 mm Hg; 0.7 kPa). 10-(1-Diethylamino-2-propyl)-2-phenothiazinecarbonitrile, L series (2.9 g) is thereby obtained in the form of beige crystals, m.p. 83° C. ($[\alpha]^{20}_D = +9 \pm 0.3°$; 0.978%; chloroform). The filtrate is then concentrated to dryness under reduced pressure (30 mm Hg; 4 kPa) at 40° C. to give a further 2.3 g of 10-(1-diethylamino-2-propyl)-2-phenothiazinecarbonitrile, L series, in the form of a beige solid, m.p. 81–82° C.

$[\alpha]^{20}_D = +8.7 \pm 0.3°$ (1.2%; chloroform).

10-(1-Ethylamino-2-propyl)-2-phenothiazinecarbonitrile, L series may be prepared in the following manner:

Ethylamine (30 cc) is added to a solution of 2-(2-cyano-10-phenothiazinyl)-1-propyl methanesulphonate, L series (16 g) in toluene (160 cc), and this mixture is brought to a temperature in the region of 105° C. for 24 hours. After being cooled, the reaction mixture is concentrated to dryness under reduced pressure (30 mm Hg; 4 kPa) at 40° C. and the residue is taken up with ethyl ether (250 cc) and N aqueous sodium hydroxide solution (50 cc). After stirring, the organic phase is separated, washed successively with distilled water (50 cc) and with saturated aqueous sodium chloride solution (50 cc), dried over magnesium sulphate, filtered and concentrated to dryness under reduced pressure (30 mm Hg; 4 kPa) to give a yellow oil (13.8 g). This residue is dissolved at a temperature in the region of 60° C. in ethanol (46 cc), and this solution is poured into a solution at 60° C. of fumaric acid (5.2 g) in ethanol (46 cc) and then left for 16 hours at a temperature in the region of 5° C. The yellow precipitate formed is drained, washed with ethanol (2×5 cc) and dried at 40° C. under reduced pressure (5 mm Hg; 0.7 kPa). 10-(1-Ethylamino-2-propyl)-2-phenothiazinecarbonitrile fumarate, L series ($[\alpha]^{20}_D + 6.2 \pm 0.4°$; 1.008%; dimethylformamide) (9.7 g) is thereby obtained. This product is suspended in ethyl ether (200 cc) and N aqueous sodium hydroxide solution (100 cc) is added. After stirring, the organic phase is separated and the aqueous phase is extracted with ethyl ether (50 cc). The organic phases are combined, washed with saturated aqueous sodium chloride solution (100 cc), dried over magnesium sulphate, filtered and concentrated to dryness under reduced pressure (300 mm Hg; 40 kPa then 30 mm Hg; 4 kPa) at 40° C. 10-(1-Ethylamino-2-propyl)-2-phenothiazinecarbonitrile, L series (7 g) is thereby obtained in the form of a yellow oil.

$[\alpha]^{20}_D = +12 \pm 0.3°$ (2%; chloroform).

EXAMPLE 22

A solution of 10-(1-diethylamino-2-propyl)-N-(3-methyl-1-butyl)-2-phenothiazinecarbothioamide, D series (2 g) and fumaric acid (0.52 g) in ethanol (20 cc) is concentrated to dryness under reduced pressure (30 mm Hg; 4 kPa) at 40° C. The residue is taken up with stirring with acetic acid (35 cc) and then treated with mercuric acetate (1.5 g). Stirring is continued at a temperature in the region of 20° C. for 16 hours. The black suspension obtained is diluted with distilled water (60 cc) and filtered. The orange filtrate is treated with caustic soda (d=1.33) to pH 13 and extracted with ethyl ether (200 cc). The organic phase is washed successively with distilled water (2×50 cc) and with saturated aqueous sodium chloride solution (50 cc) and dried over magnesium sulphate in the presence of charcoal 3S. After filtration, the colourless filtrate is concentrated to dryness under reduced pressure (30 mm Hg; 4 kPa) at 40° C.; a pale yellow oil (2 g) is thereby obtained. This product is purified by chromatography on a column (height: 25 cm; diameter: 2.6 cm) of silica gel (0.04–0.063 mm) under a slight excess pressure of nitrogen (40 kPa), eluting with a mixture (90:10 by volume) (1,000 cc) of ethyl acetate and methanol and collecting 50-cc fractions. Fractions 3 to 9 are combined and concentrated to dryness under reduced pressure (30 mm Hg; 4 kPa) at 40° C. A yellow oil ($[\alpha]^{20}_D = -15 \pm 1°$; 0.6%; chloroform) (1.5 g) is obtained. This product is dissolved in isopropyl ether (100 cc) and then treated with stirring, at a temperature in the region of 5° C., with a 0.45 N solution (5.8 cc) of hydrochloric acid in isopropyl ether. Stirring is continued for 30 minutes. The precipitate formed is drained, washed with isopropyl ether (2 cc) and dried at 40° C. under reduced pressure (5 mm Hg; 0.7 kPa). 10-(1-Diethylamino-2-propyl)-N-(3-methyl-1-butyl)-2-phenothiazinecarboxamide hydrochloride, D series (0.8 g) is thereby obtained in the form of a white solid, m.p. 105–110° C. (melts forming a paste), the NMR spectrum of which is identical to that of the product obtained in Example 21.

$[\alpha]^{20}_D = -14.6° \pm 0.5$ (0.5%; dimethylformamide).

Infrared spectrum (KBr), characteristic bands in cm$^{-1}$:

3280, 3050, 2950, 2930, 2860, 2620, 2580, 2470, 1640, 1590, 1535, 1460, 1410, 1390, 1380, 1360, 1305, 1230, 870, 825, 750.

10-(1-Diethylamino-2-propyl)-N-(3-methyl-1-butyl)-2-phenothiazinecarbothioamide, D series may be prepared in the following manner:

3-Methylbutylamine (10.7 cc) is added to a solution of 10-(1-diethylamino-2-propyl)-2-phenothiazinecarbothioamide acid fumarate, D series (3 g) in absolute ethanol (45 cc), and this solution is saturated with hydrogen sulphide. The mixture is then brought to a temperature in the region of 105° C. for 16 hours and concentrated to dryness under reduced pressure (30 mm Hg; 4 kPa) at 50° C. The residual orange oil is purified by chromatography on a column (height: 35 cm; diameter: 3 cm) of silica gel (0.2–0.063 mm), eluting with a mixture (75:25 by volume) (400 cc) of ethyl acetate and cyclohexane and collecting 40-cc fractions. Fractions 4 to 6 are combined and concentrated to dryness under reduced pressure (30 mm Hg; 4 kPa) at 50° C. to give 10-(1-diethyl-amino-2-propyl)N-(3-methyl-1-butyl)-2-phenothiazinecarbothioamide, D series (3.1 g) in the form of an orange oil.

10-(1-Diethylamino-2-propyl)-2-phenothiazinecarbothioamide acid fumarate, D series may be obtained in the following manner:

By working as described in Example 21, but starting with 10-(1-diethylamino-2-propyl)-2-phenothiazinecarbonitrile, D series (3.4 g) and triethylamine (1.4 cc) in anhydrous pyridine (68 cc), an orange oil (4 g) is obtained. This product is dissolved at a temperature in the region of 60° C. in ethanol (13 cc) and this solution is poured into a solution of fumaric acid (1.16 g) in ethanol (13 cc) at a temperature in the region of 5.C The crystals formed are drained, washed with ethanol (2×2 cc) and dried at 40° C. under reduced pressure (5 mm Hg; 0.7 kPa). 10-(1-diethylamino-2-propyl)-2-phenothiazinecarbothioamide acid fumarate, D series 3.47 g) is thereby obtained in the form of a yellow solid, m.p. 180° C.

$[\alpha]^{20}_D = -32.8 \pm 0.6°$ (0.9%; dimethylformamide).

10-(1-diethylamino-2-propyl)-2-phenothiazinecarbonitrile, D series may be obtained in the following manner:

A mixture of 10-(1-ethylamino-2-propyl)-2-phenothiazinecarbonitrile acid fumarate, D series (4 g), sodium carbonate (1.32 g) and iodoethane (1 cc) in dimethylformamide (50 cc) is heated to a temperature in the region of 150° C. for 6 hours. After being cooled, the reaction mixture is concentrated to dryness (30 mm Hg; 4 kPa) at 50° C. and the residue is taken up with ethyl acetate (100 cc) and washed successively with distilled water (50 cc) and with saturated aqueous sodium chloride solution (50 cc). The organic phase is dried over magnesium sulphate, filtered and concentrated to dryness under reduced pressure (30 mm Hg; 4 kPa) at 40° C. 10-(1-Diethylamino-2-propyl)-2-phenothiazinecarbonitrile, D series (3.4 g) is thereby obtained in the form of a yellow oil.

$[\alpha]^{20}_D = -6.8 \pm 0.4°$ (1.3%; chloroform).

10-(1-Ethylamino-2-propyl)-2-phenothiazinecarbonitrile acid fumarate, D series may be obtained in the following manner:

Ethylamine (18.75 cc) is added to a solution of 2-(2-cyano-10-phenothiazinyl)-2-propyl methanesulphonate, D series (10 g) in toluene (100 cc), and this mixture is brought to a temperature in the region of 105° C. for 24 hours. After being cooled, the reaction mixture is concentrated to dryness under reduced pressure (30 mm Hg; 4 kPa) at 40° C. The residue is taken up with ethyl ether (250 cc) and extracted successively with N aqueous hydrochloric acid solution (2×100 cc). The combined aqueous phases are alkalinized with caustic soda (d=1.33) to pH 13 and extracted with ethyl ether (2 x 200 cc). The combined organic phases are washed successively with distilled water (50 cc) and with saturated aqueous sodium chloride solution (50 cc), dried over magnesium sulphate, filtered and concentrated to dryness under reduced pressure (30 mm Hg; 4 kPa) at 40.° C. 10-(1-Ethylamino-2-propyl)-2-phenothiazinecarbonitrile D series (5 g) is thereby obtained in the form of an orange oil. This product is dissolved at a temperature in the region of 60° C. in ethanol (17 cc) and this solution is poured into a solution of fumaric acid (1.9 g) in ethanol (17 cc) at the same temperature, crystallization is then primed and the mixture is left for 16 hours at a temperature in the region of 20° C. The solid is drained, washed with ethanol (2×2 cc) and dried under reduced pressure (5 mm Hg; 0.7 kPa) at 40° C. 10-(1-Ethylamino-2-propyl)-2-phenothiazinecarbonitrile acid fumarate, D series (4 g) is thereby obtained in the form of a yellow solid, m.p. 208° C.

$[\alpha]^{20}_D = -5.2 \pm 0.5°$ (0.9%; dimethylformamide).

EXAMPLE 23

N-(3-Methylbutyl)-10-[(2RS)-1-(N-ethyl-N-methylamino)-2-propyl]-2-phenothiazinecarbothioamide (0.3 g) is dissolved in a solution of fumaric acid (81 mg) in absolute ethanol (5 cc) and the mixture is concentrated to dryness under reduced pressure (30 mm Hg; 4 kPa) at 40° C. The residual orange product of meringue-like consistency is dissolved in acetic acid (5 cc) and mercuric acetate (0.23 g) is added. The orange suspension obtained is stirred for 16 hours at a temperature in the region of 20° C. The reaction mixture is concentrated to dryness under reduced pressure (30 mm Hg; 4 kPa) at 60° C. The residue is taken up with distilled water (10 cc) and filtered and the filtrate is alkalinized with caustic soda (d=1.33) to pH 13 and extracted with ethyl acetate (2×10 cc). The combined organic phases are washed with saturated aqueous sodium chloride solution (10 cc), dried over magnesium sulphate, filtered and concentrated to dryness under reduced pressure (30 mm Hg; 4 kPa) at 40° C. The residual yellow oil (0.15 g) is dissolved in ethyl acetate (2 cc), and isopropyl ether (20 cc) is added. The solution obtained is cooled to a temperature in the region of 5° C. and a solution (5.1 cc) of 0.065N hydrochloric acid in isopropyl ether is added dropwise and with stirring. The precipitate formed is drained, washed with isopropyl ether (3×5 cc) and dried under reduced pressure (5 mm Hg; 0.7 kPa) at 40° C. N-(3-Methylbutyl)-10-[(2RS)-1-(N-ethyl-N-methylamino)-2-propyl]-2-phenothiazinecarboxamide hydrochloride (0.13 g) is thereby obtained in the form of an off-white solid, m.p. 110–120° C. (melts forming a paste).

Proton NMR (250 MHz, DMSO, $\delta$ in ppm, J in Hz):

In solution DMSO, two forms are observed, due to salification of the nitrogen.

0.92 (D, J=7, 6H, —CH(CH$_3$)$_2$); 1.06 and 1.20 (broad 2T, 3H, >NCH$_2$CH$_3$); 1.45 (Mt, 2H, —CH$_2$CH<); 1.63 (Mt, 1H, 3-methylbutyl >CH—); 1.82 (broad D, 3H,—CH$_3$); 2.77 (Cx, 3H, >NCH$_3$); 3.15 (Cx, 2H ; >NCH$_2$—CH$_3$); 3.29 Cx, 2H, —CONH—CH$_2$—); 3.48 and 3.75 (2 Cx, 3.46 - DD, J=14 and 3, and 3.73 - DD, J=14 and 8, 2H, N—CH$_2$—); 4.76 (Cx, 1H, >N—CH<); 7 to 7.4 (Cx, 5H, aromatic); 7.53 (S, 1H, —H at 1-position); 7.54 (D, J=8, 1H, —H at 3-position); 8.59 (Cx, J=5.5, 1H, —CONH—); 10.20 (Cx, 1H, —NH+).

Infrared spectrum (KBr), characteristic bands in cm$^{-1}$:

3270, 3060, 2950, 2930, 2870, 2580, 2480, 1645, 1590, 1540, 1460, 1415, 1385, 1365, 1310, 1230, 870, 845, 830, 755.

N-(3-Methylbutyl)-10-[(2RS)-1-(N-ethyl-N-methylamino)-2-propyl]-2-phenothiazinecarbothioamide may be prepared in the following manner:

A solution of 10-[(2RS)-1-(N-ethyl-N-methyl-amino)-2-propyl]-2-phenothiazinecarbothioamide (1 g) and 3-methylbutylamine (4.9 cc) in absolute ethanol (15 cc) is saturated with hydrogen sulphide and heated for 16 hours to a temperature in the region of 100° C. After being cooled, the orange solution obtained is concentrated to dryness under reduced pressure (30 mm Hg; 4 kPa) at 40° C. The residual orange oil is purified by chromatography on a column (height: 25 cm; diameter 2 cm) of silica gel (0.04–0.063 mm) under a slight excess pressure of nitrogen (40 kPa), eluting with a mixture (80:20 by volume) (500 cc) of ethyl acetate and cyclohexane and collecting 30-cc fractions. Fractions 4 to 8 are combined and concentrated to dryness under reduced pressure (30 mm Hg; 4 kPa) at 40° C. N-(3-Methylbutyl)-10-[(2RS)-1-(N-ethyl-N-methylamino)-2-propyl]-2-phenothiazinecarbothioamide (1.3 g) is thereby obtained in the form of an orange-yellow oil.

EXAMPLE 24

Mercuric acetate (0.668 g) is added with stirring to a suspension of N-(3-methylbutyl)-10-[(2RS)-1-(1-pyrrolidinyl)-2-propyl]-2-phenothiazinecarbothioamide hydrochloride (1 g) in acetic acid (20 cc), and the mixture is left to react for 5 hours 30 minutes at a temperature in the region of 20° C. The reaction mixture is diluted with ethyl acetate (150 cc) and distilled water (50 cc) and then treated with caustic soda (d=1.33) to pH 13. The organic phase is separated and the aqueous phase is extracted again with ethyl acetate (2×50 cc). The combined organic phases are washed with saturated aqueous sodium hydrogen carbonate solution (100 cc) and then with saturated aqueous sodium chloride solution (100 cc), dried over magnesium sulphate, filtered and concentrated to dryness under reduced pressure (30 mm Hg; 4 kPa) at 40° C. The residual yellow oil (0.53 g) is purified by chromatography on a column (height: 30 cm; diameter: 2.5 cm) of silica gel (0.04–0.063 mm) under a slight excess pressure of nitrogen (40 kPa), eluting successively with a mixture (97.5:2.5 by volume) (100 cc) of methylene chloride and methanol and then with a mixture (95:5 by volume) (200 cc) of methylene chloride and methanol and collecting 15-cc fractions. Fractions 12 to 34 are combined and concentrated to dryness under reduced pressure (30 mm Hg; 4 kPa) at 40° C. The oil obtained is dissolved in ethyl acetate (10 cc) and a 3N solution (0.5 cc) of hydrochloric acid in ethyl ether is added. The solid formed is drained, washed with ethyl ether (2×2 cc) and dried under reduced pressure (5 mm Hg; 0.7 kPa) at 40° C. N-(3-Methylbutyl)-10-[(2RS)-1-(1-pyrrolidinyl)-2-propyl]-2-phenothiazinecarboxamide hydrochloride (0.37 g) is thereby obtained in the form of a pale yellow solid, m.p. about 100° C. (melts forming a paste), the NMR spectrum of which is identical to that of the product described below in Example 26.

Infrared spectrum (KBr), characteristic bands in cm$^{-1}$:

3280, 3060, 2960, 2930, 2875, 2680, 2610, 2480, 1660, 1650, 1595, 1540, 1460, 1415, 1385, 1365, 1310, 1235, 860, 830, 750.

N-(3-Methylbutyl)-10-[(2RS)-1-(1-pyrrolidinyl)-2-propyl]-2-phenothiazinecarbothioamidehydrochloridemay be prepared in the following manner:

A solution of 10-[(2RS)-1-(1-pyrrolidinyl)-2-propyl]-2-phenothiazinecarbothioamide (1.89 g) and 3-methylbutylamine (8.9 cc) in absolute ethanol (28 cc) is saturated with hydrogen sulphide, and this mixture is heated for 16 hours to a temperature in the region of 110° C. After being cooled, the reaction mixture is concentrated to dryness under reduced pressure (30 mm Hg; 4 kPa) at 40° C., and the oily yellow residue (2.8 g) is purified by chromatography on a column (height: 30 cm; diameter: 2 cm) of silica gel (0.04–0.063 mm) under a slight excess pressure of nitrogen (40 kPa), eluting successively with methylene chloride (100 cc) and then a mixture (95:5 by volume) (300 cc) of methylene chloride and methanol and collecting 30-cc fractions. Fractions 4 to 8 are combined and concentrated to dryness under reduced pressure (30 mm Hg; 4 kPa) at 40° C. The oily yellow residue (2.1 g) is dissolved in ethyl acetate (15 cc) and a 3N solution (2 cc) of hydrochloric acid in ethyl ether is added. The mixture is kept stirred for 1 hour at a temperature in the region of 5° C. The precipitate formed is drained, washed with ethyl acetate (2 cc) and dried under reduced pressure (5 mm.Hg; 0.7 kPa) at 35° C. N-(3-Methylbutyl)-10-[(2RS)-1-(1-pyrrolidinyl)-2-propyl]-2-phenothiazinecarbothioamide hydrochloride (2.1 g) is thereby obtained in the form of yellow crystals, m.p. 190° C.

EXAMPLE 25

Fumaric acid (1.5 g) is added to a solution of N-(3-methylbutyl)-10-[1-(1-pyrrolidinyl)-2-propyl]phenothiazinecarbothioamide, L series (4.57 g) in absolute ethanol (100 cc), and the mixture is concentrated to dryness under reduced pressure (30 mm Hg; 4 kPa) at 40° C. The yellow meringue-like residue is taken up with acetic acid (100 cc), mercuric acetate (4.3 g) is added with stirring and stirring is continued for 16 hours at a temperature in the region of 20° C. The black suspension obtained is concentrated to one quarter of its volume under reduced pressure (30 mm Hg; 4 kPa) at 50° C., taken up with distilled water (200 cc) and filtered. The filtrate is alkalinized with caustic soda (d=1.33) to pH 13 and extracted with ethyl acetate (2×200 cc). The combined organic phases are washed successively with distilled water (2×100 cc) and with saturated aqueous sodium chloride solution (100 cc), dried over magnesium sulphate, filtered and concentrated to dryness under reduced pressure (30 mm Hg; 4 kPa) at 40° C. N-(3-Methylbutyl)-10-[1-(1-pyrrolidinyl)-2-propyl]-2-phenothiazinecarbothioamide, L series (4.88 g) is thereby obtained in the form of a slightly yellow oil. 3.3 g of this oil are dissolved in ethyl acetate (25 cc), which is stirred and treated with a 3.3 N solution (2.4 cc) of hydrochloric acid in isopropyl ether and then stirred again for 1 hour at a temperature in the region of 5° C. The solid formed is drained, washed with ethyl ether (3×10 cc) and dried under reduced pressure (5 mm Hg; 0.7 kPa) at 40° C. N-(3-Methylbutyl)-10-[1-(1-pyrrolidinyl)-2-propyl]-2-phenothiazinecarboxamide hydrochloride, L series (2.55 g) is thereby obtained in the form of a white solid, m.p. 210° C., the NMR spectrum of which is identical to that described in Example 26.

$[\alpha]^{20}_D = +14 \pm 0.9°$ (0.5%; dimethylformamide).

Infrared spectrum (KBr), characteristic bands in cm$^{-1}$:

3295, 3060, 2950, 2930, 2870, 2680, 2620, 2485, 660, 1650, 1595, 1535, 1460, 1410, 1380, 1360, 1305, 230, 855, 825, 750.

N-(3-Methylbutyl)-10-[1-(1-pyrrolidinyl)-2-propyl]-2-phenothiazinecarbothioamide, L series may be prepared in the following manner:

A solution of 10-[1-(1-pyrrolidinyl)-2-propyl]-2-phenothiazinecarbothioamide, L series (6 g) and 3-methylbutylamine (18.9 cc) in absolute ethanol (90 cc) is saturated with hydrogen sulphide and brought for 16 hours to a temperature in the region of 105° C. After being cooled, the reaction mixture is concentrated to dryness under reduced pressure (30 mm Hg; 4 kPa) at 40° C. The oily brown residue is purified by chromatography on a column (height: 40 cm; diameter: 4 cm) of silica gel (0.02–0.063 mm), eluting with methylene chloride (1 liter) and then with a mixture (95:5 by volume) (1.5 liters) of methylene chloride and methanol and collecting 80-cc fractions. Fractions 23 to 36 are combined and concentrated to dryness under reduced pressure (30 mm Hg; 4 kPa) at 40° C. N-(3-Methylbutyl)-10-[1-(1-pyrrolidinyl)-2-propyl]-2-phenothiazinecarbothioamide, L series (6.76 g) is thereby obtained in the form of an orange oil.

EXAMPLE 26

A solution of N-(3-methylbutyl)-10-[1-(1-pyrrolidinyl)-2-propyl]-2-phenothiazinecarbothioamide, D series (2 g) and fumaric acid (0.52 g) in ethanol (20 cc) is concentrated to dryness under reduced pressure (30 mm Hg; 4 kPa) at 40° C. The residual yellow product of meringue-like consistency is taken up with acetic acid (35 cc) and then treated with mercuric acetate (1.5 g) and stirred at a temperature in the region of 20° C. for 16 hours. The black suspension obtained is diluted with distilled water (50 cc) and filtered. The yellow filtrate is alkalinized to pH 13 with sodium hydroxide (d=1.33) and extracted with ethyl acetate (2×100 cc). The combined organic phases are washed successively with distilled water (2×50 cc) and with saturated aqueous sodium chloride solution (50 cc), dried over magnesium sulphate in the presence of charcoal 3S and filtered, and the colorless filtrate is concentrated to dryness under reduced pressure (30 mm Hg; 4 kPa) at 50° C. N-(3-Methyl-butyl)-10-[1-(1-pyrrolidinyl)-2-propyl]-2-phenothiazinecarbothioamide, D series (1 g) is thereby obtained in the form of a yellow oil. This product is dissolved in ethyl acetate (10 cc) and treated with a 3.3N solution (0.7 cc) of hydrochloric acid in isopropyl ether. The precipitate formed is drained, washed with isopropyl ether (3×2 cc) and dried under reduced pressure (5 mm Hg; 0.7 kPa) at 40° C. N-(3-Methylbutyl)-10-[1-(1-pyrrolidinyl)-2-propyl]-2-phenothiazinecarboxamide hydrochloride, D series (0.75 g) is thereby obtained in the form of a white solid, m.p. 200° C.

$[\alpha]^{20}_D = -17.3 \pm 0.5°$ (1.1%; dimethylformamide).

Proton NMR (250 MHz, DMSO, δ in ppm, J in Hz): 0.92 (T, J=7, 6H, —CH(CH$_3$)$_2$); 1.43 (Q, J=7, 2H, —NH—CH$_2$—CH$_2$—); 1.62 (Mt, 1H, 3-methylbutyl—CH—); 1.78 (D, J=7, 3H, —CH$_3$); 1.75 (Mt, 4H, —CH$_2$—CH$_2$—); 2.82–3.10–3.55 and 3.75 (4Cx, 1H each, pyrrolidine

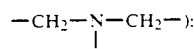

3.30 (Mt, 2H, —CONH—CH$_2$); 3.75 (AB, 2H, >N—CH$_2$); 4.75 (Mt, 1H, >N—CH<); 7 to 7.4 (Mt, 5H, aromatic); 7.53 (S, 1H, —H at 1-position); 7.55 (D, J=8, 1H, —H at 3-position); 8.6 (T, J=5, 1H, —CONH—); 10.58 (Cx, 1H, —NH+).

Infrared spectrum (KBr), characteristic bands in cm$^{-1}$:

3290, 3060, 2955, 2935, 2870, 2660, 2620, 2580, 1660, 1650, 1595, 1540, 1465, 1415, 1385, 1365, 1305, 1235, 860, 850, 830, 750.

N-(3-Methylbutyl)-10-[1-(1-pyrrolidinyl)-2-propyl]-2-phenothiazinecarbothioamide, D series may be prepared in the following manner:

3-Methylbutylamine (12.9 cc) is added to a solution of 10-[1-(1-pyrrolidinyl)-2-propyl]-2-phenothiazinecarbothioamide, D series (4.1 g) in ethanol (61.5 cc), and the mixture is then saturated with hydrogen sulphide and heated for 16 hours to a temperature in the region of 105° C. After being cooled, the solution is concentrated to dryness under reduced pressure (30 mm Hg; 4 kPa) at 40° C. A yellow oil is obtained, which is purified by chromatography on a column (height: 30 cc; diameter:

4 cm) of silica gel (0.2–0.063 mm), eluting with a mixture (95:5 by volume) (1.5 liters) of methylene chloride and methanol and collecting 80-cc fractions. Fractions 14 to 17 are combined and concentrated to dryness under reduced pressure (30 mm Hg; 4 kPa) at 40° C. N-(3-Methylbutyl)-10-[1-(1-pyrrolidinyl)-2-propyl]-2phenothiazinecarbothioamide, D series (4.7 g) is obtained in the form of an orange oil.

$[\alpha]^{20}{}_D = 3.2 \pm 0.2°$ (1.92%; chloroform).

10-[1-(1-Pyrrolidinyl)-2-propyl]-2-phenothiazinecarbothioamide, D series may be prepared in the following manner:

A mixture of 10[1-(1-pyrrolidinyl)-2-propyl]-2-phenothiazinecarbonitrile, D series (11.7 g) and triethylamine (4.9 cc) in anhydrous pyridine (234 cc) is saturated with hydrogen sulphide for 1 hour at 25° C. the mixture is stirred for 20 hours at 25° C. and the reaction mixture is then outgassed by bubbling nitrogen through, diluted with ethyl acetate (100 cc), poured into distilled water (1 liter) and extracted with ethyl acetate (2×500 cc). The combined organic phases are washed successively with distilled water (2×250 cc) and saturated aqueous sodium chloride solution (250 cc), dried over magnesium sulphate and filtered, and the yellow filtrate is concentrated to dryness under reduced pressure (30 mm Hg; 4 kPa) at 40° C. A yellow oil (18 g) is obtained, which is purified by chromatography on a column 0.063 mm) eluting with methylene chloride (1 liter) and then with a mixture (95:5 by volume) (5 liters) of methylene chloride and methanol and collecting 100-cc fractions. Fractions 23 to 50 are combined and concentrated to dryness under reduced pressure (30 mm Hg; 4 kPa) at 40° C. 10-[1-(1-Pyrrolidinyl)-2-propyl]-2-phenothiazinecarbothioamide, D series (10.7 g) is thereby obtained in the form of a yellow product of meringue-like consistency.

$[\alpha]^{20}{}_D = +40.7 \pm 0.6°$ (1.1%; chloroform).

10-[1-(1-Pyrrolidinyl)-2-propyl]-2-phenothiazinecarbonitrile, D series may be prepared in the following manner:

A mixture of 2-(2-cyano-10-phenothiazinyl)-1-propyl methanesulphonate, D series (25.5 g) and pyrrolidine (29.6 cc) in toluene (260 cc) is heated for 52 hours to a temperature in the region of 90° C. The reaction mixture is concentrated to dryness under reduced pressure (30 mm Hg; 4 kPa) at 40° C. The residue is taken up with ethyl ether (500 cc) and extracted with 2N aqueous - methanesulphonic acid solution (2×100 cc). The aqueous phase is alkalinized with caustic soda (d=1.33) to pH 13 at a temperature in the region of 5° C., and extracted successively with distilled water (100 cc) and with saturated aqueous sodium chloride solution (100 cc), dried over magnesium sulphate in the presence of charcoal 3S and filtered, and the yellow filtrate is concentrated to dryness under reduced pressure (30 mm Hg; 4 kPa) at 40° C. The orange oil (18.2 g) thereby obtained is chromatographed on a column (height: 45 cm; diameter: 4 cm) of silica gel (0.063-0.2 mm), eluting with a mixture (97.5:2.5 by volume) (2.5 liters) of methylene chloride and methanol and collecting 150-cc fractions. Fractions 8 to 16 are combined and concentrated to dryness under reduced pressure (30 mm Hg; 4 kPa) at 40° C. 10-[1-(1-pyrrolidinyl)-2-propyl]-2-phenothiazinecarbonitrile, D series (11.7 g) is thereby obtained in the form of a yellow oil.

$[\alpha]^{20}{}_D = -9.8 \pm 0.4°$ (1.1%; chloroform).

2-(2—Cyano-10-phenothiazinyl)-1-propyl methanesulphonate, D series may be prepared in the following manner:

Triethylamine (16.2 cc) is added with stirring to a solution, cooled to a temperature in the region of 5° C., of 10-(1-hydroxy-2-propyl)phenothiazinecarbonitrile, D series (20 g) in methylene chloride (200 cc), a solution of methanesulphonyl chloride (8.9 cc) in methylene chloride (89 cc) is then introduced dropwise during 25 minutes, and stirring is continued for 50 minutes at a temperature in the region of 10° C. The reaction mixture is washed successively with distilled water (2×100 cc) and with saturated aqueous sodium chloride solution (100 cc), dried over magnesium sulphate, filtered and concentrated to dryness under reduced pressure (30 mm Hg; 4 kPa) at 40° C. 2-(2—Cyano-10-phenothiazinyl)-1-propyl methanesulphonate, D series (25.8 g) is thereby obtained in the form of an orange gum, which is used without further purification for the next stage of the synthesis.

$[\alpha]^{20}{}_D = -23.1 \pm 0.4°$ (1.4%; chloroform).

10-(1-Hydroxy-2-propyl)-2-phenothiazinecarbonitrile D series may be prepared in the following manner:

(−)-2-(2—Cyano-10-phenothiazinyl)propyl (S)-1-phenylethylammonium phthalate (95.4 g) is added to a solution of potassium hydroxide (23.5 g) in ethanol (1,150 cc) under reflux, and refluxing is continued with stirring for 10 minutes. The reaction mixture is then cast into ice-cold water (1 liter) and extracted with ethyl acetate (2 liters, then 500 cc). The combined organic phases are washed successively with 0.1N aqueous hydrochloric acid solution (2×500 cc), with saturated aqueous sodium hydrogen carbonate solution (2×500 cc) and with saturated aqueous sodium chloride solution (500 cc), dried over magnesium sulphate, filtered and concentrated to dryness under reduced pressure (30 mm Hg; 4 kPa) at 40° C. The residual yellow solid (44 g) is taken up with isopropyl ether (200 cc) under reflux and the product crystallizes in the heated state. The mixture is allowed to return to a temperature in the region of 20° C and the solid is drained, washed with isopropyl ether (20 cc) and dried under reduced pressure (5 mm Hg; 0.7 kPa) at 20° C. 10-(1-Hydroxy-2-propyl)-2-phenothiazinecarbonitrile, D series (36.5 g) is thereby obtained in the form of yellow crystals, m.p. 135° C.

$[\alpha]^{20}{}_D = +13.1 \pm 0.5°$ (1.0%); chloroform.

(−)-2-(2-Cyano-10-phenothiazinyl)propyl (S)-1-phenylethylammonium phthalate may be obtained as described in Example 5 for the preparation of 2-(2-cyano-10-phenothiazinyl)-1-propyl (L series) (1R)-1-phenylethylammonium phthalate, but making use of the solid kept after the filtration. The solid is dissolved in ethyl acetate (600 cc) under reflux. After cooling, the solid formed is drained, washed with ethyl acetate (50 cc) and dried under reduced pressure (30 mm Hg; 4 kPa) at 40° C. (−)-2-(2—Cyano-10-phenothiazinyl)propyl (1S)-1-phenylethylammonium phthalate (44.2 g) is thereby obtained in the form of pale yellow crystals, m.p. 154° C.

$[\alpha]^{20}{}_D = -21.5° \pm 0.6°$ (1%; chloroform).

EXAMPLE 27

A solution of mercuric acetate (1.63 g) in acetic acid (20 cc) is added dropwise during a period of 10 minutes to a solution of N-(3-methylbutyl)-10-[(2RS)-1-piperidino-2-propyl]-2-phenothiazinecarbothioamide (2.32 g) in glacial acetic acid (20 cc). The reaction mixture is stirred for 60 minutes at 25° C. and then filtered on sintered glass covered with celite. The celite is washed with ethyl acetate (2×10 cc) and the combined filtrates are concentrated to dryness under reduced pressure (30 mm Hg; 4 kPa) to give a residue which is diluted in ethyl acetate (100 cc). The organic phase is washed with normal sodium hydroxide (2×50 cc) and (2×50 cc) and then with brine (1×50 cc), dried over magnesium sulphate, filtered and concentrated to dryness under reduced pressure (30 mm Hg; 4 kPa) at 50° C. to give a residue which is purified by chromatography on a column (height: 36 cm; diameter: 2 cm) of silica gel (0.06-0.2 mm), eluting with mixtures of cyclohexane and ethyl acetate in proportions (by volume) of 80:20 (500 cc) and 50:50 (600 cc), collecting 50 cc fractions. Fractions 8 to 20 are combined and concentrated to dryness under reduced pressure (30 mm Hg; 4 kPa) at 50° C. to give 0.95 g of N-(3-methylbutyl)-10-[(2RS)-1-piperidino-2-propyl]-2-p-henothiazinecarboxamide (0.95 g).

A 2.2 N ethereal solution (0.83 cc) of hydrochloric acid is added to a solution of N-(3-methylbutyl)-10-[(2RS)-1-piperidino-2-propyl]-2phenothiazinecarboxamide (0.80 g) in ethyl ether (40 cc). The suspension is stirred for 12 hours at 25° C. The precipitate is filtered off on sintered glass, washed with ethyl ether (2×10 cc) and dried at 40° C. under reduced pressure (5 mm Hg; 0.7 kPa) to give N-(3methylbutyl)-10-[(2RS)-1-piperidino-2-propyl]-2-phenothiazinecarbcxamide hydrochloride (0.67 g), m.p. 228° C.

Proton NMR (250 MHz, DMSO, δ in ppm, J in Hz):
0.9 (D, J=7, 6H, —CH(CH$_3$)$_2$); 1.42 (Mt, 2H, —NHCH$_2$CH$_2$—); 1.6 (Mt, 1H, 3-methylbutyl >CH—; 1.2 to 1.9 (Mt, 6H, piperidine—CH$_2$—CH$_2$—); 1.8 (D, J=7, 3H, —CH$_3$); 2.7 to 3.8 (Mt,

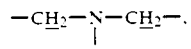

>N—CH$_2$—, —CONHCH$_2$—); 4.8 (Mt, 1H, >N—CH<); 7 to 7.35 (Mt, 5H, aromatic); 7.5 (S, 1H, —H at 1-position); 7.52 (D, J=8, 1H, —H at 3position); 8.55 (T, J=5.5, 1H, —CONH-); 9.95 (Cx, 1H, —NH+).

Infrared sprectra (KBr), characteristic bands in cm$^{-1}$:
3285, 3060, 2950, 2870, 2660, 2540, 1660, 1595, 1540, 1460, 1410, 1385, 1365, 1305, 1235, 860, 825, 745.

N-(3-Methylbutyl)-10-[(2RS)-1-[piperidino-2-propyl]-2-phenothiazinecarbothioamide may be prepared in the following manner:

3-Methylbutylamine (4.65 cc) is added to a solution of 10-[(2RS)-1-piperidino-2-propyl]-2-phenothiazinecarbothioamide (3.07 g) in absolute ethanol (65 cc). The mixture is brought to 150° C. for 16 hours. The reaction mixture is concentrated to dryness under reduced pressure (30 mm Hg; 4 kPa) at 50° C. The residue is diluted with ethyl acetate (150 cc), the solution obtained is washed with distilled water (3×50 cc), dried over magnesium sulphate and then concentrated to dryness under reduced pressure (30 mm Hg; 4 kPa), and the residue is purified by chromatography on a column (height: 23.2 cm; diameter: 3.6 cm) of silica gel (0.04-0.06 mm) with a slight excess pressure of nitrogen (40 kPa), eluting with mixtures of cyclohexane and ethyl acetate in proportions (by volume) of 80:20 (1 liter) and 50:50 (2 liters), collecting 60-cc fractions. Fractions 5 to 13 are combined and concentrated to dryness at 50° C. under reduced pressure (30 mm Hg; 4 kPa) to give N-(3-methylbutyl)-10-[(2RS)-1-piperidino-2-propyl]-2-phenothiazinecarbothioamide (2.49 g).

10-[(2RS)-1-Piperidino-2-propyl]-2-phenothiazinecarbothioamide may be obtained in the following manner:

A mixture of 10-[(2RS)-1-piperidino-2-propyl]-2-phenothiazinecarbonitrile (8.74 g) and triethylamine (3.5 cc) in anhydrous pyridine (100 cc) is saturated by bubbling in hydrogen sulphide for 3 hours at 25° C. The clear solution obtained is kept stirred for 12 hours at 25° C., and the mixture is then outgassed by bubbling through nitrogen for 2 hours. The reaction mixture is diluted with ethyl acetate (500 cc) and washed with 15 distilled water (10×200 cc). The organic phase is dried over magnesium sulphate and filtered and the filtrate is concentrated to dryness under reduced pressure (30 mm Hg; 4 kPa). The residue is purified by chromatography on a column (height: 54 cm; diameter: 3.6 cm) of silica gel (0.06-0.2 mm), eluting with a 50:50 (by volume) mixture (1.25 liters) of cyclohexane and ethyl acetate and then with pure ethyl acetate (1.25 liters) and collecting 125-cc fractions. Fractions 4 to 18 are combined and concentrated to dryness under reduced pressure (30 mm Hg; 4 kPa) at 50° C. to give 10-[(2RS)-1piperidino-2-propyl]-2-phenothiazinecarbothioamide (9.36 g).

Proton NMR (250 MHz, DMSO, δ in ppm, J in Hz):
1.38 (Mt, 2H, —CH$_2$—CH$_2$—CH$_2$—); 4.23 (Mt, J=7, 6.5 and 6, 1H ; >N—CH<); 6.9 to 7.25 (Mt, 5H, aromatic); 7.43 (broad D, J=8, 1H, —H at 3-position); 7.79 (broad S, 1H, —H at 1-position); 9.5 and 9.9 (2S, 1H each, —CSNH$_2$).

10-[(2RS)-1-Piperidino-2-propyl]-2-phenothiazinecarbonitrile may be obtained in the following manner:

Piperidine (19.8 cc) is added to a suspension of 2-(2-cyano-10-phenothiazinyl)-1-propyl methanesulphonate (36.05 g) in xylene (360 cc). The mixture is brought to reflux for 19 hours. After being cooled, the mixture is washed with distilled water (6×150 cc). The organic phase is dried over magnesium sulphate, filtered and concentrated to dryness at 50° C. under reduced pressure (30 mm Hg; 4 kPa). The residue is purified by chromatography on a column (height: 96 cm; diameter: 4.8 cm) of silica gel (0.06-0.2 mm), eluting with mixtures of cyclohexane and etyl acetate in proportions (by volume) of 90:10 (4 liters), 85:15 (4 liters), 80:20 (4 liters) and 75:25 (4 liters), collecting 500-cc fractions. The first 9 liters are discarded and fractions 8 to 13 are combined and concentrated to dryness at 50° C. under reduced pressure (30 mm Hg; 4 kPa) to give 10-[(2RS)-1-piperidino-2-propyl]-2-phenothiazinecarbonitrile (13.6 g).

Proton NMR (250 MHz, DMSO, δ in ppm, J in Hz).
1.4 (Mt, 2H, —CH$_2$—CH$_2$—CH$_2$—); 4.19 (Mt, J=7, 6.5 and 6, 1H, >N—CH<); 6.9 to 7.35 (Mt, 5H, aromatic); 7.39 (DD, J=8 and 1, 1H, —H at 3-position); 7.79 (D, J=1, 1H, —H at 1-position).

EXAMPLE 28

Mercuric acetate (0.88 g) is added to a solution of N-[(3RS)-3-methylpentyl]-10-[(2RS)-1-(l-pyrrolidinyl)-2-propyl]-2-phenothiazinecarbothioamide hydrochloride (1.2 g) in acetic acid (20.5 cc), and the mixture is stirred for 16 hours at a temperature in the region of 20° C. The orange suspension obtained is diluted with distilled water (50 cc) and filtered and the yellow filtrate is concentrated to dryness under reduced pressure (30 mm Hg; 4 kPa) at 40° C. The residue is taken up with ethyl acetate (100 cc) and distilled water (50 cc). Caustic soda (d=1.33) is added to pH 13. The organic phase is washed successively with distilled water (2×25 cc) and with saturated aqueous sodium chloride solution (25 cc) and dried over magnesium sulphate. After filtration, the yellow filtrate is concentrated to dryness under reduced pressure (30 mm Hg; 4 kPa) at 40° C. and a yellow product (0.8 g) of meringue-like consistency is thereby obtained. This product is dissolved in ethyl acetate (10 cc) and a 3.3N solution (0.5 cc) of hydrochloric acid in isopropyl ether is then added. The precipitate formed is separated by filtration, washed with isopropyl ether (3×2 cc) and dried under reduced pressure (5 mm Hg; 0.7 kPa). N-[(3RS)-3-Methylpentyl]-10[(2RS)-1-(1-pyrrolidinyl)-2-propyl]-2-phenothiazinecarboxamide hydrochloride (0.26 g), m.p. 198° C., is thereby obtained.

Proton NMR (250 MHz, CDCl$_3$, δ in ppm, J in Hz): 0.91 (T, J=7, 3H, —CH$_2$—CH$_3$); 0.97 (D, J=7, 3H, 3-methylpentyl >CH—CH$_3$; 1.2 and 1.45 (2Mt, 1H each, —CH$_2$CH$_3$); 1.48 (Mt, 2H, —NHCH$_2$CH$_2$—); 1.69 (Mt, 1H, 3-methylpentyl >CH—; 1.89 (D, J=7, 3H, —CH$_3$); 2.08 (Mt, 4H, pyrrolidine-CH$_2$-CH$_2$—); 2.9 and 3.6 to 4 (2Cx,.2H each, pyrrolidine—CH$_2$—N—CH$_2$—); 3.45 (Mt, 2H, —CONH—CH$_2$—); 3.45 (broad D, J=14, 1H, 1H of >N—CH$_2$—); 3.72 (DD, J=14 and 8, 1H, 1H of >NCH$_2$—); 5.25 (Mt, 1H, >N—CH<); 6.92 (T, J=5.5, 1H, —CONH—); 7 to 7.25 (Mt, 5H, aromatic); 7.37 (broad D, J=8, 1H, —H at 3-position); 7.5 (D, J=1, 1H, —H at 1-position); 12.4 (extended Cx, 1H, —NH+).

Infrared spectrum (KBr), characteristic bands in cm$^{-1}$.

3280, 3060, 2960, 2930, 2885, 2760, 2610, 2480, 1660, 1595, 1530, 1460, 1415, 1380, 1300, 1235, 860, 850, 830, 750.

N-[(3RS)-3-Methyl-1-pentyl]-10-[(2RS)-1-(1-pyrrolidinyl)-2-propyl]-2-phenothiazinecarbothioamide hydrochloride may be prepared in the following manner:

A mixture of 10-[(2RS)-1-(1-pyrrolidinyl)-2-propyl]-2-phenothiazinecarbothioamide (3.7 g), [(3RS)-3-methyl-1-pentyl]amine hydrochloride (3.3 g) and triethylamine (3.4 cc) in ethanol (55 cc) is saturated with hydrogen sulphide and then heated for 16 hours to 105° C. After being cooled, the solution is concentrated to dryness under reduced pressure (30 mm Hg; 4 kPa) at 40° C. An orange oil (5.6 g) is obtained, which is purified by chromatography under an excess pressure of nitrogen (40 kPa) on a column (height: 25 cm; diameter: 4 cm) of silica gel (0.063-0.2 mm), eluting with a mixture (95:5 by volume) (1 liter) of methylene chloride and methanol and collecting 60-cc fractions. Fractions 8 to 9 are combined and concentrated to dryness under reduced pressure (30 mm Hg; 4 kPa) at 40° C. . An orange oil (2.3 g) is obtained. This product is dissolved in a mixture of ethyl acetate (10 cc) and isopropyl ether (100 cc) and a 3.3N solution (1.5 cc) of hydrochloric acid in isopropyl ether is then added. The precipitate formed is drained, washed with isopropyl ether (3×10 cc) and dried under reduced pressure (5 mm Hg; 0.7 kPa) at 40° C. N-[(3RS)-3-Methyl-1-pentyl]-10-[(2RS)-1-(1-pyrrolidinyl)-2-propyl]-2-phenothiazinecarbothioamide hydrochloride (1.7 g) is thereby obtained in the form of a yellow solid, m.p. 135–140° C. (melts forming a paste).

Proton NMR (250 MHz, DMSO, δ in ppm, J in Hz): 0.88 (T, J=7, 3H, —CH$_2$—CH$_3$); 0.93 (D, J=7, 3H, 3-methylpentyl CH—CH$_3$); 1.2 and 1.4 (2Mt, 1H each, —CH$_2$CH$_3$); 1.49 (Mt, 2H, —NHCH$_2$CH$_2$); 1.72 (Mt, 1H, 3-methylpentyl —CH—); 3.50 to 3.90 (Mt, 4H, N—CH$_2$ and —CSNH—CH$_2$—); 7 to 7.35 (Mt, 5H, aromatic); 7.41 (broad D, J=8, 1H, —H at 3-position); 7.56 (broad S, 1H, —H at 1-position); 10.4 (T, J=5, 1H, —CSNH—).

10-[(2RS)-1-(1-Pyrrolidinyl)-2-propyl]-2-phenothiazinecarbothioamide may be obtained in the following manner:

A solution of 10-[(2RS)-1-(1-pyrrolidinyl)-2-propyl]-2-phenothiazinecarbonitrile (5.3 g) and triethylamine (2.2 cc) in anhydrous pyridine (106 cc) is saturated with hydrogen sulphide and left stirred for 16 hours at a temperature in the region of 20° C. The reaction mixture is poured into distilled water (500 cc) and extracted successively with ethyl acetate (500 cc, then 2×250 cc). The combined organic phases are washed with illed water (3×200 cc), dried over magnesium sulphate, filtered and concentrated to dryness under reduced pressure (30 mm Hg; 4 kPa) at 40° C. The orange oil (6.5 g) obtained is chromatographed on a column (height: 30 cm; diameter: 4 cm) of silica gel (0.2-0.063 mm) under an excess pressure of nitrogen (40 kPa), eluting with a mixture (95:5 by volume) (1 liter) of methylene chloride and methanol and then with a mixture (90:10 by volume) (1 liter) of methylene chloride and methanol and collecting 100-cc fractions. Fractions 8 to 16 are combined and concentrated to dryness under reduced pressure (30 mm Hg; 4 kPa) at 40° C. 10-[(2RS)-1-(1-Pyrrolidinyl)-2-propyl]-2-phenothiazinecarbothioamide (5.1 g) is thereby obtained in the form of a yellow solid. 1.4 g of this product are dissolved, at a temperature in the region of 60° C., in isopropanol (25 cc). After cooling, the crystals formed are drained, washed with cold isopropanol (5 cc) and dried under reduced pressure (5 mm Hg; 0.7 kPa) at 30° C. 10-[(2RS)-1-(1-Pyrrolidinyl)-2-propyl]-2-phenothiazinecarbothioamide (1.1 g) is thereby obtained in the form of yellow crystals, m.p. 150° C.

10-[(2RS)-1-(1-Pyrrolidinyl)-2-propyl]-2-phenothiazinecarbonitrile may be obtained in the following manner:

A mixture of (2RS)-2-(2-cyano-10-phenothiazinyl)-1-propyl methanesulphonate (10 g) and pyrrolidine (11.6 cc) in toluene (50 cc) is brought to 90° C. with stirring for 24 hours. After being cooled, the mixture is concentrated to dryness under reduced pressure (30 mm Hg; 4 kPa) at 40° C. and the residue is taken up with ethyl ether (200 cc) and 4N aqueous sodium hydroxide solution (15 cc). After the mixture has been stirred for 10 minutes, settling is allowed to take place and the organic phase is washed with saturated aqueous sodium chloride solution (3×25 cc), dried over magnesium sulphate, filtered and concentrated to dryness under reduced pressure (30 mm Hg; 4 kPa) at 20° C. The residual oil (11.3 g) is dissolved in 0.5N aqueous hydrochloric acid solution (60 cc). This solution is washed with ethyl ether (100 cc) and then alkalinized with an excess of N aqueous sodium hydroxide solution and extracted with ethyl ether (100 cc). The organic phase is washed with saturated aqueous sodium chloride solution (50 cc), dried over magnesium sulphate, filtered and concentrated to dryness under reduced pressure (30 mm Hg; 4 kPa) at 20° C. The residual yellow oil (9.5 g) is purified on a column (height: 30 cm; diameter: 5.8 cm) of silica gel (0.04-0.063 mm) under a slight excess pressure of nitrogen (40 kPa), eluting with a mixture (95:5 by volume) (1 liter) of methylene chloride and methanol and collecting 100-cc fractions. Fractions 3 to 10 are combined and concentrated to dryness under reduced pressure (30 mm Hg; 4 kPa) at 40° C. 10-[(2RS)-1-(1-Pyrrolidinyl)-2-propyl]-2-phenothiazinecarbonitrile (5.45 g) is thereby obtained in the form of a yellow oil.

(2RS)-2-(2-Cyano-10-phenothiazinyl)-1-propyl methanesulphonate may be obtained in the following manner:

Into a solution, cooled to a temperature in the region of 5° C., of 10-[(2RS)-1-hydroxy-2-propyl]-2-phenothiazinecarbonitrile (120.5 g) in methylene chloride (1280 cc), there is introduced with stirring, triethylamine (100 cc) followed, in the course of 30 minutes, by methanesulphonyl chloride (55.9 cc), and stirring is continued for 15 minutes while the temperature is maintained at about 10–15° C. The reaction mixture is diluted with distilled water (500 cc) at 5° C. and the organic phase is separated, washed with saturated aqueous sodium chloride solution (500 cc), dried over sodium sulphate, filtered and concentrated to dryness under reduced pressure (30 mm Hg; 4 kPa) at 40° C. The residual oil (164 g) is purified by chromatography on a column (height: 54 cm; diameter: 8.5 cm) of silica gel (0.2–0.063 mm), eluting with methylene chloride (4.4 liters) and then with a mixture (99:1 by volume) (7 liters) of methylene chloride and methanol and collecting 1-liter fractions. Fractions 3 to 11 are combined and concentrated to dryness under reduced pressure (30 mm Hg; 4 kPa) at 40° C. A yellow oil (153.5 g) is thereby obtained, which is taken up with isopropyl ether (400 cc) under reflux. On cooling, a product crystallizes, and stirring is continued for 1 hour at a temperature in the region of 5° C. The solid formed is drained, washed with ice-cold isopropyl ether (2×50 cc) and dried at 30° C. under reduced pressure (30 mm Hg; 0.4 kPa). (2RS)-2-(2-Cyano-10-phenothiazinyl)-1-propyl methanesulphonate (131.6 g) is thereby obtained in the form of pale yellow crystals, m.p. 124° C.

10-[(2RS)-1-Hydroxy-2-propyl]-2-phenothiazinecarbonitrile may be prepared in the following manner:

Into a suspension of sodium borohydride (52 g) in tetrahydrofuran (1.4 liters), 1,2-ethanedithiol (113 cc) is introduced with stirring in the course of 15 minutes and at a temperature in the region of 20° C., followed, in the course of 15 minutes under the same conditions, by a pionate (296 g) in tetrahydrofuran (1.4 liters). When the addition is complete, the reaction mixture is heated for 0 hours to a temperature in the region of 60° C. After the mixture has cooled to a temperature in the region of 5° C., 4N aqueous sodium hydroxide solution (1 liter) is introduced during 1 hour: a brisk evolution of gas is observed. The reaction mixture is then poured into a mixture of 4N aqueous sodium hydroxide solution (1 liter) and methylene chloride (3 liters) with stirring. The organic phase is isolated and the aqueous phase extracted again with methylene chloride (1 liter). The combined organic phases are washed with saturated aqueous sodium chloride solution (2×1 liter), dried over magnesium sulphate, filtered and concentrated to dryness under reduced pressure (30 mm Hg; 4 kPa) at 30° C. The viscous orange oil (290 g) is purified on a column (height: cm; diameter: 8.5 cm) of silica gel (0.2–0.063 mm), eluting successively with methylene chloride (3 liters), then with a mixture (97.5:2.5 by volume) (4 liters) of methylene chloride and methanol and with a mixture (95:5 by volume) (10 liters) of methylene chloride and methanol and collecting 1-liter fractions. Fractions 3 to 15 are combined and concentrated to dryness under reduced pressure (30 mm Hg; 4 kPa) at 30° C. 10-[(2RS)-1-Hydroxy-2-propyl]-2-phenothiazinecarbonitrile (169.7 g) is thereby obtained in the form of a yellow solid, m.p. 123° C.

Ethyl (2RS)-2-(2-cyano-10-phenothiazinyl)propionate may be prepared in the following manner:

A solution of 2-phenothiazinecarbonitrile (224.5 g) in dimethylformamide (1 liter) is introduced, with stirring and in the course of 2 hours 30 minutes, into a suspension of sodium hydride (24 g) in dimethylformamide (1 liter) at a temperature in the region of 25° C., and the mixture is left stirred for a further 1 hour 15 minutes until the evolution of gas has ceased. The fine suspension obtained is introduced, with stirring and at a temperature in the region of 25° C., in the course of 4 hours 30 minutes, into a solution of ethyl (2RS)-2chloropropionate (255 cc) in dimethylformamide (1 liter), and stirring is continued for 16 hours. Ethanol (100 cc) is then poured into the reaction mixture, and thereafter the whole is poured into a mixture of ice (2 kg) in distilled water (4 liters): a gum precipitates and then crystallizes. The solid formed is drained, washed successively with distilled water (6×500 cc) and petroleum ether (2×500 cc) and dried in the air. Ethyl (2RS)-2-(2-cyano-10-phenothiazinyl)propionate (296.5 g) is thereby obtained in the form of yellowish brown crystals, m.p. 117–118° C., which are used as they are in the next stage.

EXAMPLE 29

A mixture of N-(4-methylpentyl)-10-[(2RS)-1-(1-pyrrolidinyl)-2-propyl]-2-phenothiazinecarbothioamide hydrochloride (1.2 g) and mercuric acetate (0.88 g) in acetic acid (20.5 cc) is stirred for 16 hours at a temperature in the region of 20° C. The orange suspension obtained is diluted with distilled water (50 cc), filtered and concentrated to dryness under reduced pressure (30 mm Hg; 4 kPa) at 40° C. The residue is taken up with distilled water (50 cc) and ethyl acetate (100 cc). The mixture is alkalinized to pH 13 with sodium hydroxide (d=1.33). The organic phase is separated and then washed successively with distilled water (2×25 cc) and saturated aqueous sodium chloride solution (25 cc). The organic phase is then dried over magnesium sulphate, filtered and concentrated to dryness under reduced pressure (30 mm Hg; 4 kPa) at 40° C. The oily yellow residue (0.82 g) is dissolved in ethyl acetate (10 cc) and treated, with stirring, with a 3.3N solution (0.55 cc) of hydrochloric acid in isopropyl ether. After 1 hour with stirring at a temperature in the region of 5° C., the solid formed is drained, washed with ethyl ether (3×10 cc) and dried under reduced pressure (5 mm Hg; 0.7 kPa) at 40° C. N-(4-Metylpentyl)-10-[(2RS)-1-1-pyrrolidinyl)-2-propyl]-2-phenothiazinecarboxamide hydrochloride (0.6 g) is thereby obtained in the form of a very pale yellow solid, m.p. 218° C.

Proton NMR (200 MHz, DMSO, $\delta$ in ppm, J in Hz): 0.9 (D, J=7, 6H, —CH(CH$_3$)$_2$); 1.24 (Mt, 2H, —CH$_2$CH(CH$_3$)$_2$); 1.6 (Mt, 3H, 4-methylpentyl—CH$_2$— and >CH—); 1,8 (D, J=7, 3H, —CH$_3$) 1.75 to 2 (Mt, 4H, pyrrolidine-CH$_2$CH$_2$—); 2.88, 3.13, 3.60 and 3.75 (4Cx, 1H each, pyrrolidine—CH$_2$—N—CH$_2$—); 3.26 (Mt, 2H, —CONHCH$_2$—); 3.75 (Mt, 2H, >NCH$_2$—); 4.78 (Mt, 1H, >N—$\overline{C}$H<); 7 to 7.4 (Mt, 5H, aromatic); 7.55 (S, 1H, —H at 1-position); 7.57 (D, J=8, 1H, —H at 3-position); 8.68 (T, J=5.5, 1H, —CONH—); 10.75 (extended Cx, 1H, —NH+).

Infrared spectrum (KBr), characteristic bands in cm−1:

3285, 3060, 2955, 2930, 2870, 2680, 2620, 2485, 1650, 1595, 1540, 1460, 1415, 1385, 1365, 1235, 865, 830, 750.

N-(4-Methylpentyl)-10-[(2RS)-1-(1-pyrrolidinyl)-2-propyl]-2-phenothiazinecarbothioamidehydrochloride may be prepared in the following manner:

A solution of 10-[(2RS)-1-(1-pyrrolidinyl)-2-propyl]-2-phenothiazinecarbothioamide (2 g) and 4-methylpentylamine hydrochloride (7.4 g) in absolute ethanol (30 cc) is saturated with hydrogen sulphide. The reaction mixture is then brought for 16 hours to a temperature in the region of 105° C. After being cooled, it is concentrated to dryness under reduced pressure (30 mm Hg; 4 kPa) at 40° C. The pasty residue (5 g) is purified by chromatography on a column (height: 35 cm; diameter 3 cm) of silica gel (0.2-0.063 mm), eluting successively with methylene chloride (500 cc) and then with a mixture (95:5 by volume) (500 cc) of methylene chloride and methanol and collecting 30-cc fractions. Fractions 25 to 28 are combined and concentrated to dryness under reduced pressure (30 mm Hg; 4 kPa) at 40° C. The residual orange oil (2.16 g) is dissolved in ethyl acetate (10 cc) and there is added, with stirring, a 3.3N solution (1.5 cc) of hydrochloric acid in isopropyl ether followed by ethyl ether until a persistent cloudiness is formed. After 1 hour at a temperature in the region of 5° C., the solid formed is drained, washed with ethyl ether (3 × 10 cc) and dried under reduced pressure (5mm Hg; 0.7 kPa) at 40° C. N-(4-Methylpentyl)-10-[(2RS)-1-(1-pyrrolidinyl)-2-propyl]-2-phenothiazinecarbothioamide hydrochloride (1.7 g) is thereby obtained in the form of a yellow solid, m.p. 186° C.

Proton NMR (250 MHz, DMSO, δ in ppm, J in Hz):
0.90 (D, J=7, 6H, —CH(CH$_3$)$_2$); 1.26 (Mt, 2H, —CH$_2$—CH(CH$_3$)$_2$); 1.58 (Mt, 1H, 4-methylpentyl>CH—); 1.7 (Mt, 2H, —NHCH$_2$—CH$_2$—); 3.72 (Mt, 2H, —CSNHCH$_2$—); 7 to 7.35 (Mt, 5H, aromatic); 7.45 (broad D, J=8, 1H, —H at 3position); 7.55 (broad S, 1H, —H at 1-position); 10.52 (T, J=5, 1H, —CSNH—).

EXAMPLE 30

A suspension of N-(3,3-dimethylbutyl)-10-[(2RS)-1-(1-pyrrolidinyl)-2-propyl]-2-phenothiazinecarbothioamide hydrochloride (2.45 g) and mercuric acetate (1.6 g) in acetic acid (49 cc) is stirred for 16 hours at a temperature in the region of 20° C., and then taken up with distilled water (50 cc) and filtered. The filtrate is concentrated to dryness under reduced pressure (30 mm Hg; 4 kPa) at 40° C. The residue is taken up with ethyl acetate (100 cc) and alkalinized with N aqueous sodium hydroxide solution. The organic phase is separated, washed with saturated aqueous sodium chloride solution (50 cc), dried over magnesium sulphate, filtered and concentrated to dryness under reduced pressure (30 mm Hg; 4 kPa) at 40° C. The residual yellow product (1.6 g) of meringue-like consistency is purified by chromatography on a column (height 40 cm; diameter: 1.8 cm) of silica gel (0.2-0.063 mm), eluting with methylene chloride (100 cc) and then with a mixture (93:7 by volume) (500 cc) of methylene chloride and methanol and collecting 50-cc fractions. Fractions 3 to 10 are combined and concentrated to dryness under reduced pressure (30 mm Hg; 4 kPa) at 40° C. The residue (1.75 g) is dissolved in ethyl acetate (10 cc) and treated with a 3N solution (1.5 cc) of hydrochloric acid in ethyl ether. The solid formed is drained (1.5 g) and taken up with distilled water (20 cc) and ethyl acetate (20 cc), and alkalinized with 0.1N aqueous sodium hydroxide solution. The organic phase is separated, washed with distilled water (10 cc), dried over magnesium sulphate, filtered and concentrated to dryness under reduced pressure (30 mm Hg; 4 kPa) at 40° C. The residue (1.35 g) is purified by chromatography on a column (height: 40 cm; diameter: 1.8 cm) of silica gel (0.2-0.063 mm), eluting with ethyl acetate (700 cc) and collecting 50-cc fractions. Fractions 4 to 10 are combined and concentrated to dryness under reduced pressure (30 mm Hg; 4 kPa) at 40° C. A residual white solid (1.31 g) is obtained. 1.05 g of this residue is taken up with isopropyl ether (20 cc) under reflux with stirring for 10 minutes, and the mixture is left to cool with stirring. The solid is drained, washed with ice-cold isopropyl ether (5 cc ) and dried under reduced pressure (5 mm Hg; 0.7 kPa) at 40° C. N-(3,3-Dimethylbutyl)-10-[(2RS)-1-(1-pyrrolidinyl)-2-propyl]-2-phenothiazinecarboxamide (0.68 g) is thereby obtained in the form of white crystals, m.p. 138° C.

Proton NMR (250 MHz, DMSO, δ in ppm, J in Hz)
0.98 (S, 9H, —C(CH$_3$)$_3$); 1.47 (Mt, 2H, —CH$_2$—C(CH$_3$)$_3$); 1.61 (D, J=7, 3H, —CH$_3$); 1.7 (Mt, 4H, pyrrolidine-CH$_2$—CH$_2$—); 2.55 (masked Mt, 4H,

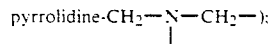
pyrrolidine-CH$_2$—N—CH$_2$—);

2.91 (DD, J=14 and 7.5, 1H, 1H of >NCH$_2$—); 3 (DD, J=14 and 5.5, 1H, 1H of >N—CH$_2$—); 3.28 (Mt, 2H, —CONHCH$_2$—); 4.2 (Mt, J=7.5, 7 and 5.5, 1H, >N—CH<); 6.9 to 7.3 (Mt, 5H, aromatic); 7.4 (D, J=8, 1H, —H at 3-position); 7.55 (S, 1H, —H at 1-position); 8.4 (T, J=5.5, 1H, —CONH—).

Infrared spectrum (KBr), characteristic bands in cm$^{-1}$:
3305, 3060, 2950, 2900, 2860, 2790, 1630, 1590, 1580, 1540, 1460, 1410, 1390, 1360, 1320, 1230, 875, 845, 825, 745.

N-(3,3-Dimethylbutyl)-10-[(2RS)-1-(1-pyrrolidinyl)-2-propyl]-2-phenothiazonecarbothioamide hydrochloride may be prepared in the following manner:

A mixture of 10-[(2RS)-1-(1-pyrrolidinyl)-2-propyl]-2-phenothiazinecarbothioamide (3 g) and 3,3-dimethylbutylamine (5.7 g) in absolute ethanol (30 cc) is brought to a temperature in the region of 100° C. for 16 hours. After being cooled, the mixture is concentrated to dryness under reduced pressure (30 mm Hg; 4 kPa) at 40° C. The residue is dissolved in ethyl acetate (100 cc) and this solution is washed with distilled water (3 × 20 cc), dried over magnesium sulphate in the presence of charcoal 3S and concentrated to dryness under reduced pressure (30 mm Hg; 4 kPa) at 40° C. The residue (5 g) is purified by chromatography on a column (height: 30 cm; diameter: 5cm) of silica gel (0.04-0.063 mm), eluting with a mixture (97:3 by volume) (2.5 liters) of methylene chloride and methanol and collecting 100-cc fractions. Fractions 18 to 24 are combined and concentrated to dryness under reduced pressure (30 mm Hg; 4 kPa) at 40° C. The residue (3.68 g) is dissolved in ethyl acetate (35 cc). This solution is filtered and a 3N solution (3.5 cc) of hydrochloric acid in ethyl ether is added. The mixture is left to stand for 2 hours at a temperature in the region of 5° C. and the solid formed is drained, washed with ethyl ether (5 cc) and dried under reduced pressure (5 mm Hg; 0.7 kPa) at 35° C. N-(3,3-Dimethylbutyl)-10-[(2RS)-1-(1-pyrrolidinyl)-2-propyl]-2-phenothiazinecarbothioamide hydrochloride (3.2 g) is thereby obtained in the form of yellow crystals, m.p. 199-200° C.

Proton NMR (250 MHz, DMSO, δ in ppm, J in Hz):
0.97 (S, 9H. —C(CH$_3$)$_3$); 1.61 (Mt, 2H, —CH$_2$—C(CH$_3$); 1.78 (D, J=7, 3H, —CH$_3$); 3.5 to 3.9 (Mt, 4H, N—CH$_2$ and —CSNHCH$_2$—); 7 to 7.35 (Mt, 5H, aromatic); 7.42 (D, J=8, 1H, —H at 3-position); 7.53 (S, 1H, —H at 1-position); 10.45 (T, J=5, 1H, —CSNH—).

EXAMPLE 31

A mixture of 10-[(2RS)-1-N-methyl-N-ethylamino)-2-propyl]-2-phenothiazinecarbothioamide (2.4 g) and propylamine (8.27 cc) in ethanol (48 cc) is heated for 16 hours to a temperature in the region of 100° C. After being cooled, the mixture is concentrated to dryness under reduced pressure (30 mm Hg; 4 kPa) at 40° C. The residual brown oil (3 g) is purified by chromatography on a column (height: 25 cm; diameter: 4 cm) of silica gel (0.04–0.063 mm) with a slight excess pressure of nitrogen (40 kPa), eluting with a mixture (95:5 by volume) (2 liters) of methylene chloride and methanol and collecting 60-cc fractions. Fractions 8 to 20 are combined and concentrated to dryness under reduced pressure (30 mm Hg; 4 kPa) at 40° C. The residual oil (1.68 g) is dissolved in ethyl ether (50 cc) in the presence of charcoal 3S. The mixture is filtered and the yellow filtrate is treated, with stirring, with a 3.3N solution (1.3 cc, of hydrochloric acid in ethyl ether, and stirring is continued for 2 hours at a temperature in the region of 20° C. The precipitate formed is drained, washed with ethyl ether (5 cc) and dried under reduced pressure (5 mm Hg; 0.68 kPa) at 35° C. 10-[(2RS)-1-(N-methyl-N-ethylamino)-2-propyl]-N-propyl-2-phenothiazinecarbothioamide hydrochloride (1.35 g) is thereby obtained in the form of a yellow solid, m.p. 110–115° C. (melts forming a paste).

Proton NMR (250 MHz, DMSO, δ in ppm, J in Hz):

In solution in DMSO, two forms are observed, due to salification of the nitrogen; this phenomenon disappears on adding CD$_3$COOD.

0.97 (T, J=7.5, 3H, —(CH$_2$)$_2$CH$_3$); 1.06 and 1.20 (2T, J=7.5, 3H, >NCH$_2$CH$_3$); 1.74 (Mt. 2H, —CH$_2$—CH$_2$—CH$_3$); 1.82 (Mt, 3H, —CH$_3$); 2.8 Mt, 3H, >N—CH$_3$); 3.18 (Mt, 2H, >N—CH$_2$CH$_3$); 3.54 and 3.80 (2Mt, 1H each, >N—CH$_2$—); 3.7 (Mt, 2H, —CSNH—CH$_2$—); 7.05 to 7.4 (Mt, 5H, aromatic); 7.45 (broad D, J=8, 1H, H at 3-position); 7.6 (broad S, 1H, —H at 1-position); 10.31 and 10.52 (2Mt, 1H each, —NH+ and —CSNH—).

Infrared spectrum (KBr), characteristic bands in cm$^{-1}$:

3210, 2970, 2940, 2880, 2650, 2480, 1590, 1535, 1465, 880 820, 750.

A solution of 10-[(2RS)-1-(N-ethyl-N-methyl-amino)-2-propyl]-N-propyl-2-phenothiazinecarbothioamide (1.1 g) and fumaric acid (0.32 g) in methanol (20 cc) is concentrated to dryness under reduced pressure (309 mm Hg; 4 kPa) at 40° C. The residual orange product of meringue-like consistency is taken up with acetic acid (22 cc), then treated with mercuric acetate (0.9 g) and stirred at a temperature in the region of 20° C. for 16 hours. The suspension obtained is diluted with distilled water (25 cc) and filtered. The yellow filtrate is concentrated to dryness under reduced pressure (30 mm Hg; 4 kPa) at 40° C. The residue is taken up with ethyl acetate (50 cc) and water (25 cc) and alkalinized with sodium hydroxide. The organic phase is separated and the aqueous phase is extracted with ethyl acetate (25 cc). The organic phases are combined, washed successively with distilled water (2×20 cc) and then with saturated aqueous sodium chloride solution (20 cc), dried over magnesium sulphate, filtered and concentrated to dryness under reduced pressure (30 mm Hg; 4 kPa) at 40° C. The yellow oily residue (1.05 g) is dissolved in a mixture (15:85 by volume) (35 cc) of ethyl acetate and isopropyl ether, and a 0.4N solution (6 cc) of hydrochloric acid in isopropyl ether is added dropwise at a temperature of 5° C. A solid precipitates. The suspension thereby obtained is stirred for 1 hour at 0° C. and then filtered. The solid is washed with isopropyl ether (3×5 cc). The solid is dried under reduced pressure (1 mm Hg; 0.13 kPa) at 50° C. to give 10-[(2RS)-1-(N-ethyl-N-methylamino)-2-propyl]-N-propyl- 2-phenothiazinecarboxamide (0.3 g) in the form of a white solid, m.p. 100° C.

Proton NMR (250 MHz, DMSO-d$_6$ +a few drops of CD$_3$COOD—d$_4$, δ in ppm, J in Hz):

0.9 (T, J=7.5, 3H, —(CH$_2$)$_2$CH$_3$; 1.09 (T, J=7.5, 3H, >NCH$_2$CH$_3$); 1.8 (D, J=7, 3H, —CH$_3$); 2.75 (S, 3H, >N—CH$_3$); 3.13 (Q, J=7.5, 2H, N—CH$_2$—CH$_3$); 3.24 (Mt, 2H, —CONH—CH$_2$—); 3.42 (DD, J=14 and 4, 1H, 1H of >N—CH$_2$—); 3.73 (DD, J=14 and 8, H, the other H of >N—CH$_2$—); 7 and 4, 1H, >N—CH<); to 7.35 >N—CH$_2$—); 4.69 (Mt, J=8, 7 and 4, 1H, >N—CH<); 7 to 7.35 (Mt, 5H, aromatic); 7.53 (S, 1H. —H at 1-position); 7.54 (D, J=8, 1H, H at 3-position); 8.55 (residual T, J=5, —CONH—).

Infrared spectrum (KBr), characteristic bands in cm$^{-1}$.

3270, 2960, 2930, 2875, 2580, 2470, 1645, 1590, 1460, 1535, 875, 830, 755.

EXAMPLE 32

Distilled water (0.16 cc) is added in the course of two minutes, with stirring and at a temperature of 20° C., to a suspension of potassium tert-butylate (1.68 g) in tert-butanol (20 cc). A solution of 10-(1-diethylamino-2-propyl)-2-phenothiazinecarbonitrile, L series (1.68 g) in tert-butanol (10 cc) is added with stirring and at a temperature of 20° C. to the solution obtained. The yellow suspension obtained is then brought to reflux for 1 hour. After the mixture is cooled to a temperature of 30° C., 1-iodopropane (1.5 cc) is added with stirring and the mixture is brought to reflux for 4 hours. After being cooled, the mixture is concentrated to dryness under reduced pressure (30 mm Hg; 4 kPa) at 40° C. The residue is taken up with ethyl ether (100 cc) and the organic phase is washed with distilled water (20 cc), dried over magnesium sulphate, filtered and concentrated to dryness under reduced pressure (30 mm Hg; 4 kPa) at 40° C. The oily yellow residue (2.3 g) is purified by chromatography on a column (height: 20 cm; diameter: 3 cm) of silica gel (0.04–0.063 mm) under a slight excess pressure of nitrogen (40 kPa), eluting successively with methylene chloride (500 cc) and with a mixture (97:3 by volume) (500 cc) of methylene chloride and methanol and collecting 30-cc fractions. Fractions 8 to 25 are combined and concentrated to dryness under reduced pressure (30 mm Hg; 4 kPa) at 40° C. to give an oily residue (1.15 g). This residue is dissolved in ethyl acetate (30 cc) and a 3.3 N solution (3 cc) of hydrochloric acid in ethyl ether is added. After 2 hours, stirring at 20° C., the precipitate formed is filtered off, washed with ethyl acetate (4×5 cc) and dried under reduced pressure (5 mm Hg; 0.67 kPa) at 40° C. to give 10-(1-diethylamino-2-propyl)-N-propyl-2-phenothiazinecarboxamide hydrochloride, L series (1.23 g) in the form of a white solid, m.p. 125–130° C.

Proton NMR (250 MHz, DMSO-d$_6$, δ in ppm, J in Hz):

0.91 (T, J=7, 3H, —(CH$_2$)$_2$CH$_3$; 1 and 1.12 (2T, J =7, respectively 3H each —N(CH$_2$CH$_3$)$_2$); 1.86 (D, J=7, 3H, —CH$_3$); 3.05 to 3.3 (Mt, 6H, —CON—H—CH$_2$— and —N(CH$_2$CH$_3$)$_2$); 3.4 and 3.7 (2 Mt, the first partially masked, the other H, >N—CH$_2$—); 4.84 (Mt, 1H, >N—CH<); 7 to 7.4 (Mt, 5H, aromatic); 7.53 (S, 1H, H at 1-position); 7.55 (D, J=8, 1H, —H at 3-position); 8.65 (T, J=5.5, 1H, —CONH—); 10.28 (Cx, 1H, —NH+Cl—).

Infrared spectrum (KBr), characteristic bands in cm$^{-1}$:

3250, 2960, 2930, 2870, 2580, 2480, 1645, 1590, 1460, 1540, 875, 830, 750.

EXAMPLE 33

Distilled water (0.28 cc) is introduced into a solution of potassium tert-butylate (1.7 g) in tert-butanol (12 cc), 10-[(2RS)-1-(N-ethyl-N-propylamino)-2-propyl]-2-phenothiazinecarbonitrile (1.1 g) is added and the mixture is brought to reflux for 30 minutes with stirring. 1-Iodopropane (1.5 cc) is then added and refluxing is continued with stirring for 3 hours 50 minutes. After being cooled, the reaction mixture is concentrated to dryness under reduced pressure (30 mm Hg; 4 kPa) at 40° C. The residue is taken up with ethyl acetate (25 cc) and the solution obtained is washed successively with distilled water (10 cc) and then with saturated aqueous sodium chloride solution (10 cc), dried over magnesium sulphate in the presence of charcoal 3S, filtered and concentrated to dryness under reduced pressure (30 mm Hg; 4 kPa) at 40° C. to give a yellow oil (0.9 g). This product is purified by chromatography on a column (height: 25 cm; diameter 3 cm) of silica gel 0.063-0.04 mm) under a slight excess pressure of nitrogen (40 kPa), eluting successively with methylene chloride (500 cc) and then with a mixture (98:2 by volume) (1 liter) of methylene chloride and methanol and finally with a mixture (96:4 by volume) (500 cc) of methylene chloride and methanol and collecting 60-cc fractions. Fractions 10 to 30 are combined and concentrated to dryness under reduced pressure (30 mm Hg; 4 kPa) at 40° C. A yellow oil (0.72 g) is thereby obtained, which is dissolved in a mixture (89:11 by volume) (45 cc) of isopropyl ether and ethyl acetate, and a 0.34 N solution (5.57 cc) of hydrochloric acid in isopropyl ether is added dropwise and with stirring at a temperature in the region of 5° C. The precipitate formed is drained, washed with isopropyl ether (10 cc) and dried under reduced pressure (5mm Hg; 0.7 kPa) at 40° C. 10-[(2RS)-1-(N-Ethyl-N-propylamino)-2-propyl]-N-propyl-2-phenothiazinecarboxamide hydrochloride (0.6 g) is thereby obtained in the form of a white solid, m.p. 95-100° C. (melts forming a paste).

Proton NMR (250 MHz, DMSO, δ in ppm and J in Hz):

In solution in DMSO, two products are observed, due t salification of the nitrogen.

0.73 and 0.84 (2T, J=7, 3H >N(CH$_2$)$_2$CH$_3$); 0.9 (T, J=7.5, 3H, —NH(CH$_2$)$_2$CH$_3$); 1 and 1.19 (2T, J=7, 3H, >NCH$_2$CH$_3$); 1.56 (Mt, 4H, —CH$_2$—CH$_2$—CH$_3$ of the 2 propyls); 1.85 (D, J=7, 3H, —CH$_3$); 3 and 3.15 (2Cx, approximately 4H, >N—CH$_2$— of the ethyl and of the propyl of N-ethyl-N-propylamino); 3.23 (Mt, 2H, —CONH—CH$_2$); approximately 3.4 and 3.75 (2Cx, 1H each, >N—CH$_2$—); 4.85 (Mt, 1H, >N—CH<); 7 to 7.4 (Mt, 5H, aromatic); 7.54 (broad S, 1H, —H at 1-position); 7.55 (broad D, J=8, 1H, —H at 3-position); 8.65 (T, J=5.5, 1H, —CONH—); 10.15 and 10.25 (2Cx, 1H in toto, —NH+).

Infrared spectrum (KBr), characteristic bands in cm$^{-1}$.

3270, 3060, 2960, 2930, 2875, 2580, 2490, 1645, 1590, 1555, 1535, 1460, 1415, 1395, 1380, 1310, 1230, 870, 830, 750.

10-[(2RS)-1-(N-Ethyl-N-propylamino)-2-propyl]-2-phenothiazinecarbonitrile may be prepared in the following manner:

A mixture of 10-[(2RS)-1-ethylamino-2-propyl]-2-phenothiazinecarbonitrile (1.5 g), 1-iodopropane (0.5 cc) and sodium carbonate (0.8 g) in dry dimethylformamide (20 cc) is brought to a temperature in the region of 150° C. for 6 hours. After being cooled, the reaction mixture is concentrated to dryness under reduced pressure (5 mm Hg; 0.7 kPa) at 50° C. The residue is taken up with ethyl acetate (50 cc) and the solution obtained is washed successively with distilled water (2×50 cc) and with saturated aqueous sodium chloride solution (25 cc). The organic phase is separated, dried over magnesium sulphate in the presence of charcoal 3S, filtered and concentrated to dryness under reduced pressure (30 mm Hg; 4 kPa) at 40° C. An orange oil (1.5 g) is obtained, which is purified by chromatography on a column (height: 25 cm; diameter: 4 cm) of silica gel (0.063-0.04 mm) under a slight excess pressure of nitrogen (300 mm Hg; 40 kPa), eluting with a mixture (97.5:2.5 by volume) (1.5 liters) of methylene chloride and methanol and collecting 60-cc fractions. Fractions 19 to 22 are combined and concentrated to dryness under reduced pressure (30 mm Hg; 4 kPa) at 40° C. 10-[(2RS)-1-(N-Ethyl-N-propylamino)-2-propyl]-2-phenothiazinecarbonitrile (1.18 g) is thereby obtained in the form of a yellow oil.

10-[(2-RS)-1-Ethylamino-2-propyl]-2-phenothiazinecarbonitrile may be prepared as described for the preparation of the starting materials described in Examples 8 and 28.

EXAMPLE 34

A solution of 10-[(2RS)-1-dimethylamino-2-propyl]-2-phenothiazinecarbonitrile (6.18 g) in tert-butanol (40 cc) is added to a solution of potassium tert-butylate (11.2 g) in a mixture of tert-butanol (120 cc) and distilled water (1.8 cc). The mixture is brought for 2 hours 30 minutes to reflux after 1-iodo-3-methylbutane (13.2 cc) has been added. After being cooled, the mixture is diluted with ethyl acetate (300 cc) and the organic phase is washed with distilled water (3×500 cc) and saturated sodium chloride solution (100 cc) and then dried over magnesium sulphate. The filtrate is concentrated to dryness at 50° C. under reduced pressure (30 mm Hg; 4 kPa) to give a residue which is purified by chromatography on a column (height: 40 cm; diameter: 2.5 cm) of silica (0.06-0.2 mm), eluting with mixtures of ethyl acetate and cyclohexane in proportions (by volume) of 70:30 (300 cc), 50:50 (300 cc) and 20:80 (500 cc) and then with pure ethyl acetate (1 liter) while collecting 60-cc fractions. Fractions 29 to 34 are combined and concentrated to dryness at 50° C. under reduced pressure (30 mm Hg; 4 kPa) to give 10-[(2RS)-1-dimethylamino-2-propyl]-N-(3-methylbutyl)-2-phenothiazinecarboxamide (1.5 g) in the form of a pale yellow solid.

10-[(2RS)-1-Dimethylamino-2-propyl]-N-(3-methylbutyl)-2-phenothiazinecarboxamide (1.5 g) is stirred in isopropyl ether (30 cc) for 15 minutes. The solid is filtered off on sintered glass and then dried at 40° C. under reduced pressure (30 mm Hg; 4 kPa) to give 10-[(2RS)-1-dimethylamino-2-propyl]-N-(3-methylbutyl)-2-phenothiazinecarboxamide (1.2 g) in the form of a pale yellow amorphous solid, m.p. 105° C.

Proton NMR (250 MHz, CDCl$_3$, δ in ppm, J in Hz). 0.98, (D, J=7, 6H, —CH(CH$_3$)$_2$); 1.53 (Q, J=7, 2H, —CH$_2$CH(CH$_3$)$_2$); 1.68 (D, J=7, 3H, —CH$_3$); 1.71 (Mt, 1H, —CH(CH$_3$)$_2$); 2.38 (S, 6H, —N(CH$_3$)$_2$); 2.75 (DD, J=13 and 6, 1H, 1H of >N—CH$_2$—); 3.08 (DD, J=13 and 5, 1H, 1H of >NCH$_2$—); 3.47 (Mt, 2H, —CONH—CH$_2$—); 4.27 (Mt, J=7, 6 and 5, 1H, >N—CH<); 6.2 (Cx, 1H, —CONH—); 6.90 to 7.25 (Mt, 5H, aromatic); 7.3 (DD, J=8 and 1.5, 1H, —H at 3-position); 7.7 (D, J=1.5, 1H, —H at 1-position).

Infrared spectrum (KBr), characteristic bands in cm$^{-1}$. 3340, 3065, 3050, 2950, 2870, 2815, 2765, 1630, 1590, 1580, 1540, 1460, 1420, 1385, 1365, 1315, 1235, 845, 825, 755. 10-[(2RS)-1-Dimethylamino-2-propyl]-2-phenothiazinecarbonitrile may be prepared in the following An Erlenmeyer is charged with a solution of 2-chloro-1-dimethylaminopropane hydrochloride (342 g) in distilled water (700 cc). 10N sodium hydroxide solution (270 cc) is added and the mixture is extracted with toluene (1.3 liters). The organic phase is dried over magnesium sulphate, filtered and concentrated at 50° C. under reduced pressure (30 mm Hg; 4 kPa) until a residual volume of 800 cc is obtained. Powdered potassium hydroxide (96.7 g) is added to a suspension of 2-cyanophenothiazine (242 g) in methyl ethyl ketone (2.2 liters). The temperature of the mixture rises spontaneously to 24° C., and the mixture is brought to 60° C. for half an hour while stirring. The toluene solution of 2-chloro-1-dimethylaminopropane prepared above is added in the course of 30 minutes. The mixture is heated under reflux for 12 hours. After being cooled, the mixture is transferred to a dropping funnel and washed with distilled water (2×2 liters). The organic phase is dried over magnesium sulphate, filtered and then concentrated to dryness under reduced pressure (30 mm Hg; 4 kPa) at 50° C. to given an oil, which is diluted in ethyl ether (2 liters). The solution obtained is cooled and primed by scratching. The yellow precipitate which has crystallized is removed by filtration. The mother liquors are concentrated to dryness under reduced pressure (100 mm Hg; 15 kPa) at 30° C. to give a brown oil which is purified by chromatography on a column (height: 80 cm; diameter: 8.5 cm) of silica (0.2–0.06 mm), eluting with an 80:20 (by volume) mixture of cyclohexane and ethyl acetate and collecting 1-liter fractions. Fractions 7 to 16 are combined and concentrated to dryness at 50° C. under reduced pressure (30 mm Hg; 4 kPa) to give 10-[(2RS)-1-dimethylamino-2-propyl]-2-phenothiazinecarbonitrile (54.8 g) in the form of a brown oil.

EXAMPLE 35

Distilled water (0.27 cc) is added in the course of 2 minutes, with stirring and at a temperature in the region of 20° C., to a suspension of potassium tert-butylate (1.71 in tert-butanol (20 cc). A solution of 10-[(2RS)-1-(1-pyrrolidinyl)-2-propyl]-2-phenothiazinecarbonitrile 1.1 g) in tert-butanol (10cc) is added, with stirring and at a temperature in the region of 20° C., to the solution obtained. The light brown solution is then brought to reflux for 25 minutes. After the mixture is cooled to a temperature in the region of 30° C., 1-iodopropane (2.55 g) is added with stirring and the mixture is brought to reflux for 3 hours 15 minutes. After being cooled, the mixture is concentrated to dryness under reduced pressure (30 mm Hg; 4 kPa) at 40° C. The residue is taken up with distilled water (10 cc) and the mixture is extracted with ethyl acetate (25 cc). The organic phase is dried over potassium carbonate, filtered and concentrated to dryness under reduced pressure (30 cm Hg; 4 kPa) at 40° C. The residual grey product (1.5 g) of meringue-like consistency is purified by chromatography on a column (height: 25 cm; diameter: 3.2 cm) of silica gel (0.04–0.063 mm) under slight excess pressure of nitrogen (40 kPa), eluting with mixture (90:10 by volume) (750 cc) of methylene chloride and methanol and collecting 25-cc fractions. Fractions 12 to 24 are combined and concentrated to dryness under reduce pressure (30 mm Hg; 4 kPa) at 40° C. N-Propyl-10-[(2RS)-1-(1-pyrrolidinyl)-2-propyl]-2-phenothiazinecarboxamide (0.85 g) is thereby obtained in the form of a yellow resin.

EXAMPLE 36

Distilled water (2.8 cc) is added to a solution of potassium tert-butylate (17.6 g) in tert-butanol (120 cc), followed by the portionwise addition of 10-[1-(1-pyrrolidinyl)-2-propyl]-2-phenothiazinecarbonitrile hydrochloride, L series (11.7 g), and the mixture is brought to reflux with stirring for 25 minutes. After the mixture is cooled, 1-iodopropane (15.3 cc) is added and the mixture is again brought to reflux with stirring for 3 hours. After being cooled, the mixture is concentrated to dryness under reduced pressure (30 mm Hg; 4 kPa) at 40° C. The residue is taken up with ethyl acetate (250 cc) and the solution obtained is washed successively with distilled water (100 cc) and saturated aqueous sodium chloride solution (100 cc), dried over magnesium sulphate, filtered and concentrated to dryness under reduced pressure (30 mm Hg; 4 kPa) at 40° C. The residual orange oil (12 g) is purified by chromatography on a column (height: 30 cm; diameter: 6 cm) of silica gel (0.2–0.063 mm), eluting with a mixture (95:5 by volume) (5 liters) of methylene chloride and methanol and collecting 100-cc fractions. Fractions 25 to 43 are combined and concentrated to dryness under reduced pressure (30 mm Hg; 4 kPa) at 40° C. The residual yellow oil (8.4 g) is dissolved in ethyl acetate (84 cc) and treated, dropwise and with stirring, with a 3.3N solution (6.4 cc) of hydrochloric acid in isopropyl ether. The solid formed is drained, washed with ethyl acetate (15 cc) and dried under reduced pressure (5 mm Hg; 0.7 kPa) at 40° C. N-Propyl-10-[1-(1-pyrrolidinyl)-2-propyl]-2-phenothiazinecarboxamide hydrochloride, L series (6.5 g) is thereby obtained in the form of a white powder, m.p. 183°–188° C. (melts forming a paste), the characteristics of which are identical to those of the product obtained in Example 5.

EXAMPLE 37

(2RS)-2-Methylbutylamine (2.95 cc) is added to a solution of 10-[(2RS)-1-diethylamino-2-propyl]-2-phenothiazinecarbonitrile (1.69 g) in absolute ethanol (25 cc). The mixture is brought to 180° C. for 20 hours; (2RS)-2-methylbutylamine (2.95 cc) is added and the mixture is brought to 200° C. for 20 hours. Air is then bubbled through for 30 minutes and the mixture is again brought to 200° C. for 16 hours and then diluted with ethyl acetate (150 cc), washed with distilled water (4×50 cc), dried over magnesium sulphate, filtered and concentrated to dryness under reduced pressure (30 mm Hg; 4 kPa) at 50° C. The residue obtained is purified by chromatography on a column (height: 16 cm; diameter:

2.8 cm) of silica gel (0.04-0.06 mm) with a slight excess pressure of nitrogen (40 kPa), eluting with 20:80 (by volume) mixtures (1.5 liter) of cyclohexane and ethyl acetate, collecting 60-cc fractions. Fractions 8 to 20 are combined and concentrated to dryness under reduced pressure (30 mm Hg; kPa) at 50° C. to give a product (0.30 g) which is purified again on a column of basic alumina (height: 6.5 cm; diameter: 13.8 cm), eluting with a 90:10 (by volume) mixture (1 liter) of cyclohexane and ethyl acetate, collecting 100-cc fractions. Fractions 3 to 9 are combined and concentrated to dryness under reduced pressure (30 mm Hg; 4 kPa) to give 10-[(2RS)-1-diethyl-amino-2-propyl]-N-[(2RS)-2-methylbutyl]-2-phenothiazinecarboxamide (0.25 g).

Fumaric acid (0.07 g) dissolved in 2-propanol (1 cc) under reflux is added to a solution of 10-[(2RS)-1-diethylamino-2-propyl]-N-[(2RS)-2-methylbutyl]-2-phenothiazinecarboxamide (0.25 g) in boiling 2-propanol (2.5 cc). Crystallization is primed by scratching, and the mixture is stirred for 2 hours at 25° C. and then left to stand for 12 hours at 0° C. The crystals are filtered off and dried under reduced pressure (5 mm Hg; 0.7 kPa) at 40° C. to give 10-[(2RS)]-1-diethylamino-2-propyl]-N-[(2RS)-2-methylbutyl]-2-phenothiazinecarboxamide fumarate (0.19 g), m.p. at 110° C.

Proton NMR (250 MHz, DMSO, δ in ppm, J in Hz):
0.9 (Mt, 12H, 2 —CH$_3$ of 2-methylbutyl and —N(CH$_2$CH$_3$)$_2$); 1.13 and 1.43 (2Mt, 1H each, —CH$_2$—CH$_3$); 1.63 (Mt, 1H, 2-methylbutyl CH—); 1.66 (D, J=7, 1H, —CH$_3$); 2.55 (masked Mt, 4H, —N(CH$_2$—CH$_3$)$_2$); 2.77 (DD, J=14 and 6, 1H, 1h of >N—CH$_2$—); 3.08 (DD, J=14 and 6.5, 1H of >NCH$_2$—); 3 to 3.3 (Mt, 2H, —CONH—CH$_2$—); 4.20 (Mt, J=7, 6.5 and 6, 1H, >N—CH<); 6.63 (S, 2H, fumarate —CH=CH—); 6.90 to 7.3 (Mt, 5H, aromatic); 7.42 (DD, J=8 and 1, 1H, —H at 3-position); 7.52 (D, J=1, 1H, —H at 1position); 8.43 (T, J=5.5, 1H, —CONH—).

Infrared spectrum (KBr), characteristic bands in cm$^{-1}$:
3300, 3050, 2960, 2920, 2870, 2640, 2480, 1900, 1700, 1630, 1590, 1550, 1460, 1410, 1380, 1300, 1225, 980, 875, 830, 750, 635.

10-[(2RS)-1-Diethylamino-2-propyl]-2-phenothiazinecarbonitrile may be prepared as described for the preparation of the starting material used in Example 2.

EXAMPLE 38

Distilled water (0.45 cc) is introduced into a solution of potassium tert-butylate (5.6 g) in tert-butanol (40 cc) and 10-[(2RS)-1-(1-pyrrolidinyl)-2-propyl]-2-phenothiazinecarbonitrile (3.7 g) is added with stirring, and the mixture is brought to reflux for 15 minutes. 1-Bromo-2-ethylbutane (7 cc) is then added and stirring is continued for 6 hours under reflux. After being cooled, the reaction mixture is concentrated to dryness under reduced pressure (30 mm Hg; 4kPa) at 40° C. The residue is taken up in ethyl acetate (250 cc), washed successively with distilled water (2 × 100 cc) and with aqueous sodium chloride solution (100 cc), dried over magnesium sulphate, filtered and concentrated to dryness under reduced pressure (30 mm Hg; 4 kPa) at 40° C. The residue (4.5 g) is purified by chromatography on a column (height: 25 cm; diameter: 4 cm) of silica gel (0.04-0.06 mm) with a slight excess pressure of nitrogen (40.5 kPa), eluting with a mixture (50:50 by volume) (1.5 liter) of ethyl acetate and cyclohexane and collecting 50-cc fractions. Fractions 13 to 25 are combined and concentrated to dryness under reduced pressure (30 mm Hg; 4 kPa) at 40° C. to give a yellow oil (2.5 g) which crystallizes. This product is taken up in isopropyl ether (100 cc) under reflux and the solution is cooled. The crystals formed are drained, washed with cold isopropyl ether (10 cc) and dried under reduced pressure (5 mm Hg; 0.67 kPa) at 40° C. to give N-(2-ethylbutyl)-10-[(2RS)-1-(1-pyrrolidinyl)-2-propyl]-2-phenothiazinecarboxamide (1.9 g) in the form of white crystals, m.p. 115° C.

Proton NMR (250 MHz, CDCl$_3$, δ in ppm and J in Hz):
0.96 (T, J=7, 6H, 2-ethylbutyl—CH$_3$); 1.42 (Mt, 4H, 2-ethylbutyl—CH$_2$—); 1.53 (Mt, 1H, 2-ethylbutyl->CH—); 1.7 (D, J=7, 3H, —CH$_3$); 1.82 (Mt, 4H, pyrrolidine-N—CH$_2$—); 2.66 (Mt, 4H, pyrrolidine >N—CH$_2$—); 2.99 {DD, J=12.5 and 6.5, 1H, 1H of >N—CH$_2$—); 3.18 (DD, J=12.5 and 6, 1H, 1H of N—CH$_2$—); 3.41 (Mt, 2H, —CONH—CH$_2$—); 4.31 (Mt, J=7, 6.5 and 6, 1H, >N—CH<); 6.20 (T, J=5.5, 1H, —CONH—); 6.90 to 7.20 (Mt, 5H, aromatic); 7.27 (DD, J=8 and 1H, H at 3-position); 7.65 (D, J=1, 1H, H at 1-position).

Infrared spectrum (KBr), characteristic bands in cm$^{-1}$:
3245, 2960, 2930, 2870, 2780, 1630, 1595, 1580, 465, 1545, 875, 835, 825, 750.

EXAMPLE 39

10-[(1-(1-Pyrrolidinyl)-2-propyl]-2-phenothiazinecarboxylic acid hydrochloride, L series (1 g) in methylene chloride (30 cc) is cooled to a temperature in the region of 5° C., and thionyl chloride (0.5 cc) is added with stirring. After 20 minutes, the temperature is brought to 20° C. and stirring is continued for 2 hours. The light yellow solution obtained is concentrated to dryness under reduced pressure (30 mm Hg; 4 kPa) at 30° C. The residual yellow product of meringue-like consistency is dissolved in methylene chloride (30 cc) and propylamine (0.5 cc) is introduced dropwise and with stirring. After 1 hour,s stirring at 20° C., the mixture is concentrated to dryness under reduced pressure (30 mm Hg; 4 kPa) at 40° C. and the residue is taken up with ethyl ether (100 cc). The solution obtained is washed successively with N sodium hydroxide (15 cc) and with saturated aqueous sodium chloride solution (15 cc), dried over magnesium sulphate, filtered and concentrated to dryness under reduced pressure (30 mm Hg; 4 kPa) at 40° C. The residual pale yellow oil (0.63 g) is dissolved in ethyl acetate (10 cc) and treated with a 3.3N solution (0.5 cc) of hydrochloric acid in isopropyl ether at a temperature in the region of 5° C. and with stirring. The precipitate formed is drained, washed with isopropyl ether (2 cc) and dried under reduced pressure (5 mm Hg; 0.7 kPa) at 40° C. N-Propyl-10-[1-(1-pyrrolidinyl)-2-propyl]-2-phenothiazinecarboxamide hydrochloride, L series (0.64 g) is thereby obtained in the form of a white solid, m.p. 190° C., the characteristics of which are identical to those of the product obtained in Example 5.

10-[1-Pyrrolidinyl)-2-propyl]-2-phenothiazinecarboxylic acid hydrochloride, L series may be obtained in the following manner:

10-[1-(1-Pyrrolidinyl)-2-propyl]-2-phenothiazinecarbonitrile hydrochloride, L series (5 g) is added to a solution of potassium hydroxide (1.75 g) in glycol (30 cc), and the mixture is stirred for 4 hours under reflux.

After being cooled, the yellow solution obtained is diluted with acetone (75 cc) and a 3N solution (5 cc) of hydrochloric acid in ethyl ether, filtered and diluted again with acetone (75 cc) and a 3N solution (5 cc) of hydrochloric acid in ethyl ether. After priming, the mixture is left to crystallize for 16 hours at a temperature in the region of 5° C. The solid obtained is drained, washed with ethyl ether (10 cc) and dried under reduced pressure (5 mm Hg; 0.7 kPa) at 40° C. 10-[1-(1-Pyrrolidinyl)-2-propyl]-2-phenothiazinecarboxylic acid hydrochloride, L series (2.9 g) is thereby obtained in the form of a pale yellow solid, m.p. 200-210° C. (melts forming a paste).

EXAMPLE 40

Thionyl chloride (0.75 cc) is introduced during 5 minutes and with stirring into a suspension of 10-[(2RS)-1-(1-pyrrolidinyl)-2-propyl]-2-phenothiazinecarboxylic acid hydrochloride (1.5 g) in methylene chloride (45 cc) while the temperature is maintained in the vicinity of 5° C. Stirring is continued for 180 minutes while heating to a temperature in the region of 20° C. and the yellow solution obtained is concentrated to dryness under reduced pressure (30 mm Hg; 4kPa) at 40° C. The residue is dissolved in methylene chloride (45 cc), and 2-methylpentylamine (0.97 g) and triethylamine (1.4 cc) are added. Stirring is maintained for 16 hours at 20° C. The reaction mixture is concentrated to dryness under reduced pressure (30 mm Hg; 4 kPa) at 40° C., taken up with ethyl acetate (100 cc), washed with N aqueous sodium hydroxide solution (100 cc), then with distilled water (2×50 cc) and with saturated sodium chloride solution (50 cc), dried over magnesium sulphate, filtered and concentrated to dryness under reduced pressure (30 mm Hg; 4 kPa) at 40° C. The oily yellow residue (1.27 g) is dissolved in isopropyl ether (50 cc) and a 0.5 N solution (6 cc) of hydrochloric acid in isopropyl ether is added. After 30 minutes, stirring at 5° C., the precipitate formed is filtered off, washed with isopropyl ether (3×10 cc) and dried under reduced pressure (5 mm Hg; 0.67 kPa) at 40° C. to give N-(2-methylpentyl)-10-[(2RS)-1-(1-pyrrolidinyl)-2-propyl]-2-phenothiazinecarboxamide hydrochloride (1 g) in the form of a beige solid, m.p. 138° C.

Proton NMR (250 MHz, DMSO-d$_6$, δ in ppm, J in Hz):

0.90 (Mt, 6H, 2-methylpentyl—CH$_3$); 1 to 1.5 (Mt, 2-methylpentyl>CH—CH$_2$—CH$_2$—); 1.78 (D, J=7, —CH3); 1.7 to 2 (Mt, 4H, pyrrolidine—CH$_2$—); 2.84, 3.08, 3.60 and 3.74 (4 Cx, 1H each respectively, pyrrolidine >N—CH$_2$—); 3.05 and 3.18 (2 Mt, 1H each respectively, —CONH—C—H$_2$—); 3.76 (limiting AB, 2H, >N—CH$_2$—); 4.78 (Mt, 1H, >N—CH<); 7 to 7.4 (Mt, 5H, aromatic); 7.53 (S, 1H, —H at 1-position); 7.55 (D, J=8, 1H, H at 3-position); 8.65 (T, J=5.5, 1H, —CONH—); 10.8 (Cx, 1H, NH+Cl⁻).

Infrared spectrum (KBr), characteristic bands in cm$^{-1}$:

3260, 2960, 2925, 2870, 2580, 2470, 1640, 1590, 1460, 1535, 865, 835, 750.

10-[(2RS)-1-(1-Pyrrolidinyl)-2-propyl]-2-phenothiazinecarboxylic acid hydrochloride may be prepared in the following manner:

By working as in Example 39, but staring with 10-[(2RS)-1-(1-pyrrolidinyl)-2-propyl]-2-phenothiazinecarbonitrile hydrochloride (20 g), crude 10-[(2RS)-1-(1-pyrrolidinyl)-2-propyl]-2-phenothiazinecarboxylic acid hydrochloride (16.1 g) is obtained, which is recrystallized in boiling 2-propanol (330 cc). After the mixture is cooled, the crystals are filtered off and dried under reduced pressure (5 mm Hg; 0.67 kPa) to give 10-[(2RS)-1-(1-pyrrolidinyl)-2-propyl]-2-phenothiazinecarboxylic acid hydrochloride (8.7 g) in the form of yellow crystals, m.p. 215-217° C.

EXAMPLE 41

Thionyl chloride (0.75 cc) is introduced during 5 minutes and with stirring into a suspension of 10-[(2RS)-1-(1-pyrrolidinyl)-2-propyl]-2-phenothiazinecarboxylic acid with hydrochloride (1.5 g) in methylene chloride (45 cc) while the temperature is maintained in the vicinity of 5° C. Stirring is continued for 4 hours while heating to a temperature in the region of 20° C., and the yellow solution obtained is concentrated to dryness under reduced pressure (30 mm Hg; 4 kPa) at 50° C. The residue is dissolved in methylene chloride (45 cc), and 2,3-dimethylbutylamine hydrochloride (1.3 g) and triethylamine (1.4 cc) are added. Stirring is maintained for sixteen hours at 20° C. The reaction mixture is concentrated to dryness under reduced pressure (30 mm Hg; 4 kPa) at 40° C., taken up with ethyl acetate (100 cc), washed with N aqueous sodium hydroxide solution (100 cc), then with distilled water (2×50 cc) and with saturated aqueous sodium chloride solution (50 cc), dried over magnesium sulphate, filtered and concentrated to dryness under reduced pressure (30 mm Hg; 4 kPa) at 40° C. The oily yellow residue is dissolved in hot isopropyl ether (20 cc). The crystals formed after cooling are drained, washed with cold isopropyl ether (2 cc) and dried under reduced pressure (5 mm Hg; 0.67 kPa) at 40° C. to give N-(2,3-dimethylbutyl)-10-[(2RS)-1-(1-pyrrolidinyl)-2-propyl]-2-phenothiazinecarboxamide (0.8 g) in the form of a greyish-yellow solid, m.p. 138° C.

Proton NMR (250 MHz, DMSO-d$_6$, δ in ppm, J in Hz):

0.75 to 0.95 (Mt, 9H, the 3 CH$_3$ of 2,3-dimethylbutyl); 1.59 (D, J=7, 3H, —CH$_3$); 1.55 to 1.75 (Mt, 2H, 2,3-dimethylbutyl CH—); 1.7 (Cx, 4H, pyrrolidine—CH$_2$—); 2.53 (Mt partially masked, pyrrolidine >N—CH$_2$—); 2.9 (DD, J=12.5 and 7.5, 1H, 1H of —NCH$_2$—); 3.02 (DD, J=12.5 and 6, 1H, 1H of >N—CH$_2$—); 3.06 and 3.26 (Mt, 1H each respectively, 2,3-dimethylbutyl-CONH—CH$_2$—); 4.21 (Mt, J =7.5, 7 and 6, 1H, >N—CH<); 6.9 to 7.3 (Mt, 5H, aromatic); 7.43 (DD, J=3 and 1, 1H, —H at 3-position); 7.54 (D, J =1, 1H, —H at 1-position); 8.4 (T , J=5.5, 1H, —CO—NH—).

Infrared spectrum (KBr), characteristic bands in cm$^{-1}$.

3300, 2960, 2870, 2800, 1630, 1590, 1580, 1490, 1465, 1545, 875, 825, 750.

The present invention also relates to the pharmaceutical compositions consisting of a product of general formula (I) in free form or in the form of an addition salt with a pharmaceutically acceptable acid, optionally in combination with any other pharmaceutically compatible product which can be inert or physiologically active. The compositions according to the invention may be used parenterally, orally, rectally or topically.

The sterile compositions for parenteral administration, which can be, in particular, used in the form of perfusions, are preferably solutions, aqueous or nonaqueous, suspensions or emulsions. As a solvent or vehicle, water, propylene glycol, a polyethylene glycol, vegetable oils, especially olive oil, injectable organic esters, e.g. ethyl oleate, or other suitable organic solvents may be used. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They can also be prepared in the form of sterile solid compositions which can be dissolved at the time of use in a sterile injectable medium.

The compositions for rectal administration are suppositories or rectal capsules which contain, apart from the active product, excipients such as cocoa butter, semi-synthetic glycerides or polyethylene glycols.

As solid compositions for oral administration, tablets, pills, powders or granules may be used. In these compositions, the active product according to the invention (optionally in combination with another pharmaceutically compatible product) is mixed with one or more inert diluents or adjuvants such as sucrose, lactose or starch. These compositions can also comprise substances other than diluents, e.g. a lubricant such as magnesium stearate.

As liquid compositions for oral administration, emulsions of a pharmaceutically acceptable nature, solutions, suspensions, syrups and elixirs containing inert diluents such as water or liquid paraffin may be used. These compositions can also comprise substances other than diluents, e.g. wetting, sweetening or flavouring products.

The compositions for topical administration can be e.g. creams, ointments or lotions.

In human therapy, the products according to the invention are especially useful in the treatment of pain of traumatic origin, postoperative, homotopic and menstrual pain, headaches, etc., as well as in diuretic treatments.

The dosages depend on the effect sought and the treatment period. For an adult, they are generally between 0.25 and 1.500 mg per day, taken in several doses at intervals.

Generally speaking, the doctor will determine the dosage which he considers most suitable in accordance with the age, weight and all other factors specific to the subject to be treated. The examples which follow, given without implied limitation, illustrate compositions according to the invention.

Example A

Tablets containing a 25-mg dose of active product (base) and having the following composition are prepared according to the usual technique:

| | |
|---|---|
| N-propyl-10-[1-(1-pyrrolidinyl)-2-propyl]-2-phenothiazinecarboxamide hydrochloride, L series | 27 mg |
| starch | 83 mg |
| silica | 30 mg |
| magnesium stearate | 3 mg |

EXAMPLE B

A solution for intravenous administration containing a dose of active product (base) of 25 mg/cc is prepared according to the usual technique:

| | |
|---|---|
| N-propyl-10-[1-(1-pyrrolidinyl)- | 2.70 g |

| | |
|---|---|
| 2-propyl]-2-phenothiazinecarboxamide hydrochloride, L series | |
| ascorbic acid | 0.100 g |
| neutral sodium sulphite | 0.050 g |
| sodium hydroxide, 1 N (q.s. pH 4) approximately | 0.08 cc |
| NaCl (q.s. isotonicity) approximately | 0.650 g |
| water for injections q.s. | 100 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Compounds of the formula:

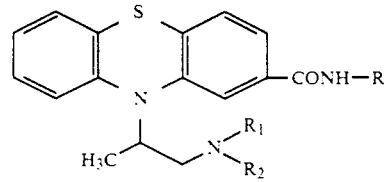

in which R is an alkyl radical containing 1 to 6 carbon atoms in a straight or branched chain and $R_1$ and $R_2$, which maybe identical or different, are linear or branched alkyl radicals containing 1 to 4 carbon atoms or form, together with the nitrogen atom to which they are attached, a heterocycle selected from the group consisting of pyrrolyl, piperidinyl, perhydroazepinyl, optical isomers of the asymmetric carbon and acid addition salt thereof.

2. Compounds according to claim 1, in wich R is an alkyl radical containing 2 to 6 carbon atoms in a straight or branched chain and the symbols $R_1$ and $R_2$, which may be identical or different, are linear or branched alkyl radicals containing 1 to 3 carbon atoms or form, together with the nitrogen atom to whic they are attached a heterocycle selected from the group consisting of pyrrolyl, piperidinyl, perhydroazepinyl, optical isomers of the asymmetric carbon and acid addition salt thereof.

3. Compounds according to claim 1, wherein R is an alkyl radical containing 3 to 6 carbon atoms in a straight or branched chain and the symbols $R_1$ and $R_2$, which may be identical or different, are linear or branched alkyl radicals containing 2 to 3 carbon atoms or form, together with the nitrogen atom to which they are attached, a heterocycle selected from the group consisting of pyrrolyl, piperidinyl, and perhydroazepinyl, in the form of a mixture of optical isomers of the asymmetric carbon thereof.

4. N-Propyl-10-(1-(1-pyrrolidinyl))-2-propyl-2-phenothiazinecarboxamide, or optical isomers of the asymmetric carbon thereof.

5. N-(3-Methylbutyl)-10-(1-(1-pyrrolidinyl))-2-propyl-2-phenothiazinecarboxamide or optical isomers of the asymmetric carbon thereof.

6. N-()2-Methylpropyl)-10-(1-(1-pyrrolidinyl)-2-propoyl-2-phenothiazinecarboxamide or optical isomers ofthe asymmetric crabon thereof.

7. N-Butyl-10-(1-(1-pyrrolidinyl)-2-propyl-2-phenothiazinecarboxamide or optical isomers of the asymmetric carbon thereof.

8. N-(3-Methylbutyl)-10-(1-piperidino-2-propyl)-2-phenothiazinecarboxamide or optical isomers of the asymmetric carbon thereof.

9. A method of obtaining analgesia in a human or animal subject comprising administering to the subject an analgesic effective amount of a phenothiazine compound as claimed in claim 1.

10. A method according to claim 9, wherein the compound is N-propyl-10-(1-pyrrolidinyl)-2-propyl)-2-penothiazinecarboxamide, or optical isomers of the asymmetric carbon thereof.

11. A method according to claim 9, wherein the compound is N-(3-methylbutyl)-10-(1-(1-pyrrolidinyl)-2-propyl-2-phenothiazinecarboxamide or optical isomers of the asymmetric carbon thereof.

12. A method according to claim 9, wherein the compound is N-(2-methylpropyl)-10(1-(1-pyrrolidinyl)-2-propyl-2phenothiazinecarboxamide or optical isomers of the asymmetric carbon thereof.

13. A method according to claim 9, wherein the compound is N-butyl-10(1-(1-pyrrolidinyl)-2-propyl-2-phenothiazinecarboxamide or optical isomers of the asymmetric carbon thereof.

14. A method according to claim 9, wherein the compound is N-(3-methylbutyl)-10(1-piperidino-2-propyl)-2-phenothiazinecarboxamide or optical isomers of the asymmetric carbon thereof.

15. A method of obtaining a diuretic effect in a human or animal subject comprising administering to the subject a diuretic effective amount of a phenothiazine compound as claimed in claim 1.

16. A method according to claim 15, wherein the compound is N-propyl-10(1-(1-pyrrolidinyl)-b 2-propyl-2-phenothiazinecarboxamide, or optical isomers of the asymmetric carbon thereof.

17. A method according to claim 15, wherein the compound is N-(3-methylbutyl)-10(1-(1-pyrrolidinyl)-2-propyl-2-phenothiazinecarboxamide or optical isomers of the asymmetric carbon thereof.

18. A method according to claim 15, wherein the compound is N-(2-methylpropyl)-10-(1-(1-pyrrolidinyl)-2-propyl-2-phenothiazinecarboxamide or optical isomers of the asymmetric carbon thereof.

19. A method according to claim 15, wherein the compound is N-butyl-10-2-propyl-2-phenothiazinecarboxamide or optical isomers of the asymmetric carbon thereof.

20. A method according to claim 15, wherein the compound is N-(3-methylbutyl)-10-(1-piperidino-2-propyl)-2-phenothiazinecarboxamide or optical isomers of the asymmetric carbon thereof.

* * * * *

UNITED STATES PATENT AND TRADEMARK OFFICE
CERTIFICATE OF CORRECTION

PATENT NO. : 5,049,669

DATED : September 17, 1991

INVENTOR(S) : Garret et al

It is certified that error appears in the above-identified patent and that said Letters Patent is hereby corrected as shown below:

Column 64, lines 1&2, change "propyl-22phenothiazine" to -- propyl)-2-phenothiazine --.

Column 64, line 1, change "N-()2-Methylpropyl" to --N-(2-Methylpropyl --.

Column 65, line 1, change "penothiazinecarboxamide" to -- phenothiazinecarboxamide --.

lines 13-18, change "propyl-2-phenothiazine to --propyl)-2-phenothiazine --.

Column 66, lines 2&3, change "pyrrolidinyl) -b 2-propyl" to --pyrrolidinyl)-2-propyl).

lines 16 to 19, change "propyl -2-phenothiazine" to -- propyl) -2-phenothiazine --.

Column 66, line 2, after "butyl-10" insert --(1-(1-pyrrolidinyl) --.

Signed and Sealed this

First Day of June, 1993

MICHAEL K. KIRK

*Attest:*

*Attesting Officer*   Acting Commissioner of Patents and Trademarks